US010696740B2

(12) United States Patent
Bansal

(10) Patent No.: US 10,696,740 B2
(45) Date of Patent: Jun. 30, 2020

(54) METHODS OF TREATING OCULAR DISEASES

(71) Applicant: NOVELMED THERAPEUTICS, INC., Cleveland, OH (US)

(72) Inventor: Rekha Bansal, Cleveland, OH (US)

(73) Assignee: NOVELMED THERAPEUTICS, INC., Cleveland, OH (US)

( * ) Notice: Subject to any disclaimer, the term of this patent is extended or adjusted under 35 U.S.C. 154(b) by 0 days.

(21) Appl. No.: 16/254,173

(22) Filed: Jan. 22, 2019

(65) Prior Publication Data

US 2019/0169279 A1    Jun. 6, 2019

Related U.S. Application Data

(63) Continuation of application No. 15/106,017, filed as application No. PCT/US2014/049938 on Aug. 6, 2014, now Pat. No. 10,183,989.

(60) Provisional application No. 61/920,541, filed on Dec. 24, 2013.

(51) Int. Cl.
| | |
|---|---|
| *A61K 39/39* | (2006.01) |
| *C07K 16/18* | (2006.01) |
| *A61K 39/395* | (2006.01) |
| *A61K 45/06* | (2006.01) |
| *C07K 16/22* | (2006.01) |
| *A61P 27/02* | (2006.01) |
| *A61K 39/00* | (2006.01) |

(52) U.S. Cl.
CPC .......... *C07K 16/18* (2013.01); *A61K 39/3955* (2013.01); *A61K 45/06* (2013.01); *A61P 27/02* (2018.01); *C07K 16/22* (2013.01); *A61K 2039/505* (2013.01); *C07K 2317/24* (2013.01); *C07K 2317/55* (2013.01); *C07K 2317/565* (2013.01); *C07K 2317/71* (2013.01); *C07K 2317/76* (2013.01)

(58) Field of Classification Search
CPC ............................ C07K 16/22; A61K 39/3955
See application file for complete search history.

(56) References Cited

U.S. PATENT DOCUMENTS

| | | |
|---|---|---|
| 2003/0171320 A1 | 9/2003 | Guyer |
| 2009/0081211 A1 | 3/2009 | Campagne |
| 2009/0214538 A1 | 8/2009 | Fung et al. |
| 2009/0269356 A1 | 10/2009 | Epstein et al. |
| 2010/0015139 A1 | 1/2010 | Bansal |
| 2013/0039925 A1 | 2/2013 | Bansal |

FOREIGN PATENT DOCUMENTS

| | | |
|---|---|---|
| JP | 2012-525829 A | 10/2012 |
| WO | 2011/112850 A1 | 9/2011 |
| WO | 2013/152020 A1 | 10/2013 |
| WO | 2013/152024 A1 | 10/2013 |

OTHER PUBLICATIONS

Katschke et al., "Structural and Functional Analysis of C3b-specific Antibody the Selectively Inhibits the Alternative Pathway of Complement", Journal of Biological Chemistry, 2009, vol. 284, No. 16, p. 10473 to 10479.
Office action for Japanese application No. 2016-540993, dated Apr. 24, 2018.
Supplemental European Search Report for Application No. 14874978. 1-1412/3086809, dated Jun. 27, 2017.
Australian Examination Report for Application No. 2014370404, dated Jun. 18, 2019.

*Primary Examiner* — Gyan Chandra
(74) *Attorney, Agent, or Firm* — Tarolli, Sundheim, Covell & Tummino LLP

(57) ABSTRACT

A method of treating a complement mediated ocular inflammation, hemorrhaging and fibrosis, and the pathological consequences thereof, in a subject in need thereof, the method comprising of administering to the subject a therapeutically effective amount of an antibody which inhibits the alternative complement pathway, wherein the antibody administered is effective for inhibiting complement mediated ocular inflammation, hemorrhaging and fibrosis, and the pathological consequences thereof.

17 Claims, 14 Drawing Sheets

Specification includes a Sequence Listing.

A: Hemorrhage in Control Eyes
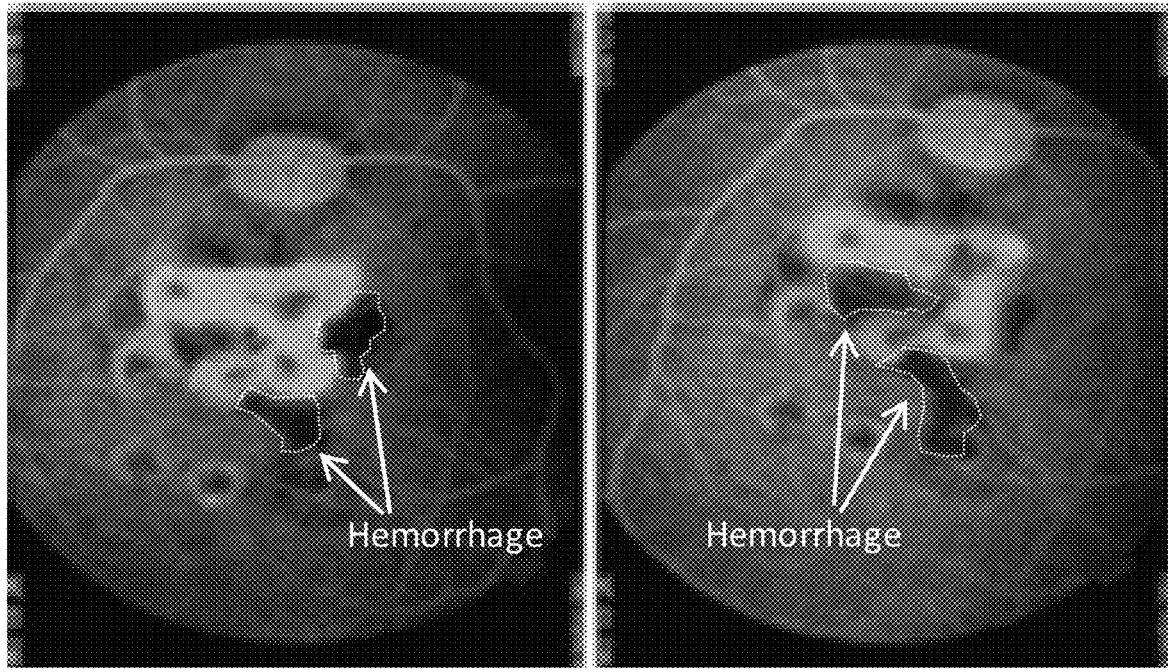
B: Treated Eyes
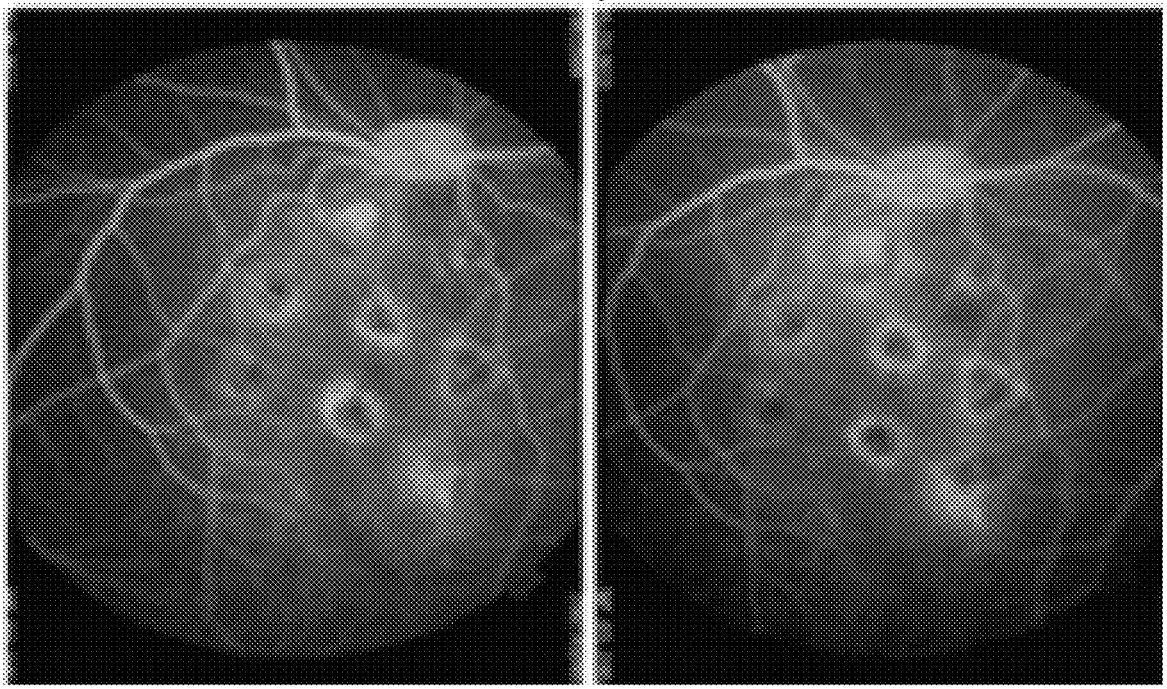
Figs. 10A-B

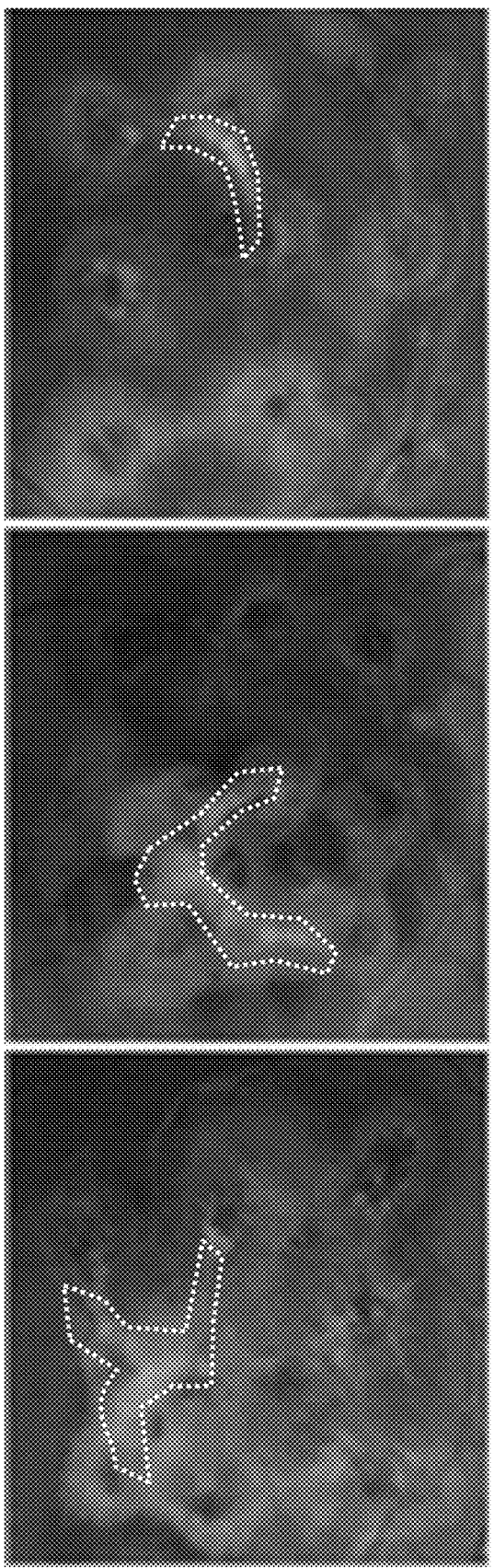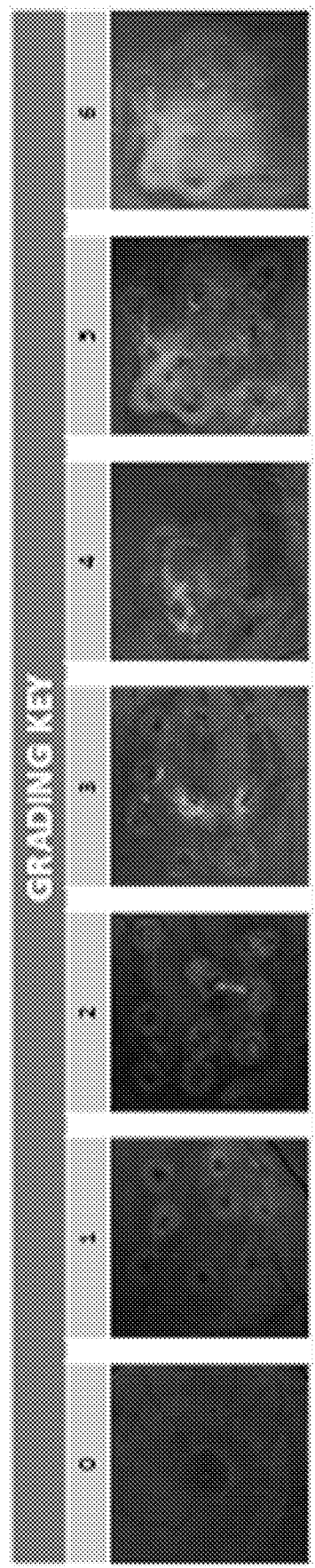
Figs. 13A-B

METHODS OF TREATING OCULAR DISEASES

RELATED APPLICATION

This application claims priority benefit of U.S. Provisional Patent Application Ser. No. 61/920,541, filed on Dec. 24, 2013, the content of which is incorporated herein by reference.

FIELD OF THE INVENTION

The present invention relates to the prevention and treatment of complement-mediated ophthalmic diseases that can be caused by or associated with complement activation and complement activation byproducts, and particularly relates to compositions and methods of using inhibitors of complement activation to treat and prevent fibrosis, hemorrhage, inflammation, neovascularization and choroidal neovascularization in ocular space.

BACKGROUND

The complement system is activated in ocular diseases. FIG. 1 provides a schematic diagram of the two primary pathways of the complement system; the classical pathway and the alternative pathway. The alternative pathway (AP) is activated by pathogens and by foreign or abnormal surfaces (such as drusen) and is capable of rapid self-amplification. Excessive and/or prolonged activation of the AP is believed to be the primary cause of many inflammatory and non-inflammatory pathologies and disorders. Age-related macular degeneration (AMD), diabetic retinopathy, uveitis, retinal fibrosis, hemorrhage, and inflammation in many ocular pathologies and disorders, are caused by AP activation and dysregulation.

The AP consists of complement Factors B, D, and P (Properdin). FIG. 2 provides a schematic diagram of the cytokines and growth factors which are produced as a result of complement system activation. Complement factors C3a and C5a activate immune system cells, and other types of cells, to produce TNF-alpha, VEGF, cytokines, growth factors, and other inflammatory mediators. Upon AP activation, C3b binds Properdin and Factor B, forming the complex PC3bB. Factor D then cleaves the Factor B within the complex. This cleavage of Factor B produces an active convertase which cleaves C3 into more C3b and C3a, thereby perpetuating the formation of additional C3 convertase. Additional molecules of C3b and Bb combine with PC3bBb to form an active C5 convertase which cleaves molecules of C5 into C5b and C5a. The C5b then associates with factors C6, C7, C8 and C9 to form the lytic macromolecule C5b-9 (also known as the Membrane Attack Complex, or "MAC"). MAC lyses cells by penetrating cell membranes. This is one of the known processes by which RPE cells, rods and cones, in the context of AMD and other ocular disorders, become damaged as a result of complement system activation.

SUMMARY

Embodiments described herein relate to compositions and methods of treating and/or preventing ocular pathologies mediated via fibrosis, vascular hemorrhage, inflammation, and cell death in a subject in need thereof. The method can include administering to the subject a therapeutically effective amount of an alternative pathway (AP) inhibitor to the subject to inhibit fibrosis, vascular hemorrhage, inflammation, and/or cell death in a subject.

In some embodiments, the method can include treating, preventing, and/or inhibiting choroidal neovascularization, retinal atrophy, retinal fibrosis, vascular hemorrhage, and inflammation associated with ocular disorders of a subject in need thereof by administering to the subject a therapeutically effective amount of an alternative pathway inhibitor antibody or antigen binding fragment thereof that selectively blocks the alternative pathway but has no effect on the lectin or the classical pathway. For example, the method can include selective inhibition of the alternative pathway by antibodies that bind properdin with high affinity (e.g., $K_D$ of 1 pM to 1000 pM) and block the association of properdin to C3b and C5b. Such antibodies can bind to at least one of the six TSRs selected from the group consisting of TSR0, TSR1, TSR4, TSR5, and TSR6. The use of an anti-properdin antibody to inhibit retinal fibrosis and hemorrhage is novel as no complement inhibitors have shown inhibition of retinal fibrosis and retinal hemorrhage.

In other embodiments, the method can include treating, preventing, and/or inhibiting VEGF formation, C5b-9 formation and cytokine formation associated with ocular disorders of a subject in need thereof by administering to the subject a therapeutically effective amount of an alternative pathway inhibitor antibody (i.e., anti-AP antibody) or antigen binding fragment thereof that selectively blocks the alternative pathway but has no effect on lectin or the classical pathway. In some embodiments, the anti-AP antibodies can include anti-properdin antibodies that bind properdin and block properdin interaction with C3b/C5b and inhibit inflammation, tissue injury, and neovascularization. The administration of the anti-AP antibodies can prevent the formation of C3a/C5a via the alternative pathway, prevent activation of inflammatory cells including retinal epithelial cells via C3a/C5a, release of endothelial growth factors that promote neovascularization (e.g., VEGF), prevent production of inflammatory mediators from activated cells (e.g., cytokines), and prevent production of C5b-9 responsible for tissue injury (e.g., MAC) and injury of retina epithelial cells, rods, and cones. Injured cells of the eye produce LDH which is marker of tissue death. The anti-AP antibodies can also prevent Lactate DeHydrogenase (LDH) formation and be used to inhibit ocular cell death Both C3a/C5a generated via the alternative pathway activate ocular cells including but not limited to RPE cells, rods and cones cells, and cause subsequent release of inflammatory mediators and VEGF growth factors that promote neovascularization. Inhibition of C3a/C5a can control VEGF formation and inflammatory mediators and therefore control of inflammation. Additional molecules known to be produced via the activation of the alternative pathway are; TNF-α, IL-1, IL-6, IL-8, IL-17, VEGF, and/or PDGF. Anti-AP antibodies are cable of controlling such activation in ocular disorders.

Formation of blood vessels is critical for tissue repair, which is mediated via VEGF formation in disease. Both C3a/C5a generated via the alternative pathway, activate ocular cells including but not limited to RPE cells, rods and cones cells and cause subsequent release of VEGF and PDGF growth factors that promote neovascularization. Inhibition of C3a/C5a is therefore expected to control VEGF formation that causes pathology and not the VEGF responsible for tissue repair. In some embodiments, the anti-AP antibodies described herein can be used in a prophylactic treatment for a subject undergoing an ophthalmologic procedure who has been identified as being at risk for developing a complement mediated ocular disorder post procedure. In some embodiments, the anti-AP antibodies can inhibit fibrosis, hemorrhage and inflammation associated with the ocular procedure. In still other embodiments, the anti-AP antibodies can prevent neovascularization following the ophthalmologic procedure without inhibiting tissue repair.

In another embodiment, a process for inhibiting fibrosis and hemorrhage with normal tissue repair in a subject undergoing an ocular surgical procedure (or other physical ocular trauma) can include administering to the subject an anti-AP antibody to promote wound healing. In one embodiment, the process for treating AP mediated ocular pathologies can occur during an ocular surgical procedure wherein the subject undergoing the procedure suffers from a condition characterized by retinal hemorrhage or inflammation, which may/may not lead to vision loss. This embodiment includes the step of administering an anti-AP antibody either immediate before, during or after the surgical procedure.

In other embodiments, an anti-AP antibody can be used to prevent fibrosis and hemorrhage secondary to a pathology of uveitis, including but not limited to; Iritis, Pars planitis, Choroiditis, Chorioretinitis, Anterior uveitis, Posterior uveitis, Scleritis, ocular neovascularization, atherosclerosis, retinal artery occlusion secondary to antiphospholipid syndrome, neovascular glaucoma, rubeosis iridis, Purtscher's retinopathy, Sorsby's fundus dystrophy, Doyne Honeycomb Retinal Dystrophy, Malattia Leventinese, Familial Dominant Drusen, North Carolina macular dystrophy, Juvenile Macular degeneration, Stargardt's disease, Vitelliform Macular Dystrophy, Adult-Onset Foveomacular Vitelliform Dystrophy (AOFVD), Sorsby's fundus dystrophy, and Best's Disease.

In other embodiments, one or more of the claimed anti-AP antibodies can be used to prevent inflammation, neovascularization, cellular atrophy, tissue degradation, release of LDH, fibrosis and/or hemorrhage secondary to a pathology of uveitis, including but not limited to; Iritis, Pars planitis, Choroiditis, Chorioretinitis, Anterior uveitis, Posterior uveitis, or Scleritis, ocular neovascularization, diabetic retinopathy or other inflammatory disorder of the eye associated with diabetes, prevent hypertensive retinopathy, prevent autoimmune uveitis or uveitis secondary to an autoimmune disorder, Behçet's Disease, Eales Disease, or other autoimmune inflammatory disease of the eye, atherosclerosis, retinal artery occlusion secondary to antiphospholipid syndrome, neovascular glaucoma, rubeosis iridis, Purtscher's retinopathy, AMD, Sorsby's fundus dystrophy, Doyne Honeycomb Retinal Dystrophy, Malattia Leventinese, Familial Dominant Drusen, North Carolina macular dystrophy, Juvenile Macular degeneration, Stargardt's disease, Vitelliform Macular Dystrophy, Adult-Onset Foveomacular Vitelliform Dystrophy (AOFVD), Sorsby's fundus dystrophy, or Best's Disease, vascular occlusion including, but not limited to; Central retinal vein occlusion (CRVO), occlusive peripheral arterial disease, ocular ischemic syndrome secondary to atherosclerosis, retinal artery occlusion secondary to antiphospholipid syndrome, neovascular glaucoma, rubeosis iridis, or Purtscher's retinopathy, retinopathy of prematurity or familial exudative vitreoretinopathy, ocular pathology occurring in the anterior segments of the eye, and Fuchs' corneal endothelial dystrophy.

In some embodiments, an anti-AP antibody is used to prevent fibrosis and/or hemorrhage secondary to a pathology characterized by vascular occlusion. Such pathologies associated with vascular occlusion can include: Central retinal vein occlusion (CRVO), occlusive peripheral arterial disease, ocular ischemic syndrome secondary to atherosclerosis, retinal artery occlusion secondary to antiphospholipid syndrome, neovascular glaucoma, rubeosis iridis, and Purtscher's retinopathy.

In one embodiment, the anti-AP antibody is used to prevent fibrosis and hemorrhage secondary to diabetic retinopathy. In another embodiment, an anti-P, anti-C3b, or anti-Bb antibody is used to treat any or all AP mediated pathologies associated with retinal fibrosis or hemorrhage in a diabetic patient, hypertensive retinopathy, an autoimmune disorder, autoimmune uveitis or uveitis, Behçet's Disease, Eales Disease, or other autoimmune disease of the eye.

In some embodiments, the anti-AP antibody is used to prevent fibrosis and/or hemorrhage secondary to retinopathy of prematurity or familial exudative vitreoretinopathy, ocular pathology occurring in the anterior segments of the eye, Fuchs' corneal endothelial dystrophy, repeated treatment with anti-VEGF agents for prevention of neovascularization.

In some embodiments, the anti-AP antibody used to treat ocular hemorrhage and/or fibrosis is one which binds to one of the group of complement factors which includes Ba, Bb, C3b, D, C5, C6, C7 or C8. In other embodiments of the invention, the anti-AP antibody used to treat ocular hemorrhage and/or fibrosis is one which also inhibits the classical or lectin pathway.

In some embodiments, the anti-AP antibody can be an anti-properdin or anti-P antibody. The anti-properdin antibodies can be capable of inhibiting neovascularization while also inhibiting ocular inflammation, ocular edema, retinal fibrosis and hemorrhage. The present invention provides a process for preventing or treating diseases and disorders which involve AP mediated neovascularization, ocular inflammation, ocular edema, ocular tissue atrophy, vascular permeability, fibrosis, hemorrhage and other inflammatory and autoimmune driven conditions and pathologies.

In another embodiment, one or more of the anti-P antibodies described herein can be used to treat Wet AMD. One or more of the anti-P antibodies described herein may be used to treat a subject who has previously been treated with an anti-VEGF agent. One or more of the claimed anti-P antibodies described herein may be used to treat a subject requiring treatment for neovascularization wherein anti-VEGF agents are counter indicated. In another embodiment, one or more of the anti-P antibodies can be used to prevent development of Dry AMD post treatment with an anti-VEGF agent.

Embodiments described herein also relate to a process of using an anti-P antibody for controlling and preventing ocular pathologies wherein at least one of the following are part of the disease process; inflammation, neovascularization, cellular atrophy, tissue degradation, release of LDH, fibrosis and/or hemorrhage In another embodiment, a process for treating AP mediated ocular pathologies associated with AP activation occurring during or after an ocular surgical procedure can include administering one or more anti-P antibody to the subject either immediately prior to, during or immediately following the ocular procedure.

Another embodiment relates to the use of these anti-AP antibodies for the preparation of a medicament or composition for the treatment of disorders associated with excessive or uncontrolled complement activation. They include complement activation during ocular disorders, particularly disorders where neovascularization, tissue injury, tissue destruction, geographic atrophy characterize the disease.

BRIEF DESCRIPTION OF THE DRAWINGS

FIGS. 10(A-B) illustrate: A. shows the visualization of retinal hemorrhage in images taken of rhesus monkey eyes, taken from the rhesus Wet-AMD/CNV model study. Hemorrhage is seen in these images as exceptionally dark, or black, regions. For this figure, a few, but not all, of these regions have been outlined with a dotted white line. The images are provided only as examples of the visualization of hemorrhage. B provides an example, for comparison to the control, of images taken of treated retinas.

FIGS. 13(A-B) illustrate a Visualization of Fibrosis—All of the images above were taken of rhesus monkey retinas in a rhesus model of CNV study. In FIG. 13A, the areas outlined in dotted white lines are a few examples of the appearance of fibrosis, in Week3 of the study (note that there is more fibrosis in the pictures than is outlined for purposes of these examples). Observers graded each image shown in FIG. 12 using the grading key provided as FIG. 13B above.

DETAILED DESCRIPTION

Definitions

Figure 1:
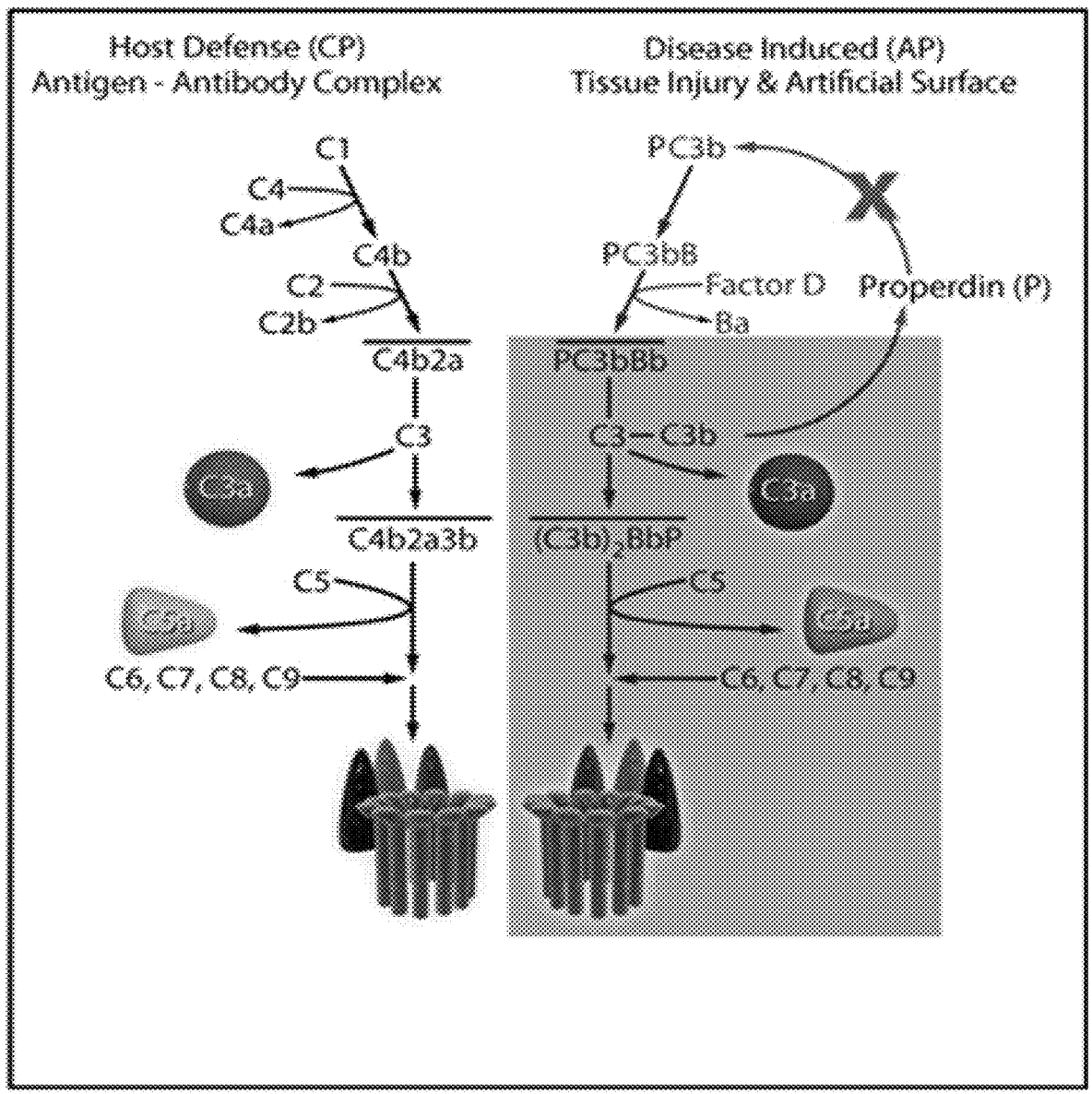
FIG. 1 is a schematic diagram of both the classical and alternative complement pathways.

Unless specifically defined herein, all terms used in this document have the same meaning as would be understood by those of ordinary skill in the art of the present invention. The following definitions are provided for clarity, and to define their intended meaning as used in the specification and claims to describe the present invention.

Complement Pathways

"CLASSICAL PATHWAY" refers to the complement system pathway which is triggered/activated by antigen-antibody complexes.

"ALTERNATIVE PATHWAY" (abbreviated as "AP" or "the AP") refers to the complement system pathway with is triggered/activated by an artificial or dead cell surface (or cell-surface like material) which is recognized as a foreign surface.

"ALTERNATIVE PATHWAY SPECIFIC PROTEIN" refers to Factor B, Factor Bb, Factor D, Properdin, and/or AP mediated C3b which is specifically produced by AP C3 convertase.

"ANTI-AP ANTIBODIES" refers to a group of antibodies which includes all antibodies targeted to AP specific proteins, and any antibody targeted to (bind to) AP mediated C5, C6, C7, C8, and C9. AP antibodies also include antibodies which bind to any protein or molecule which regulates AP mediated production of C3, C3b, P, B, D, C5, C6, C7, C8, C9, or S protein, such as DAF, MIRL.

"ANTI-P ANTIBODIES" are antibodies which were raised against human properdin or animal properdin. Anti-P antibodies include all antibodies which bind to human or animal properdin and which inhibit the AP.

"C3a DEPENDENT CELLULAR ACTIVATION" describes the activation of neutrophils, monocytes, platelets, T lymphocytes, endothelial cells, mast cells, platelets, retinal epithelial cells, rods, cones, and other cells which occurs when C3a produced by the AP binds to C3a cell receptors.

"C5a DEPENDENT CELLULAR ACTIVATION" describes the activation of neutrophils, monocytes, platelets, T lymphocytes, endothelial cells, mast cells, platelets, retinal epithelial cells, rods, cones, and other cells which occurs when C5a produced by the AP binds to C5a cell receptors.

"C5b-9/MAC MEDIATED/DEPENDENT TISSUE INJURY/CELL DAMAGE" describes the cellular damage caused by the formation of sC5b-9 and/or C5b-9 (also known as Membrane Attack Complex, or "MAC"). Such tissue injury occurs in ocular diseases where complement mediated MAC production and deposition are a part of the disease pathology.

"AP MEDIATED INFLAMMATION" refers to a multitude of physiologic processes, cell activations, and protein productions which are mediated by the AP and which cause and/or perpetuate inflammation. AP mediated inflammation can be measured by continued or increased formation, and/or release, of AP dependent C3a, C3b, C5a, C5b, C5b-9, and/or sC5b-9, and all the anticipated consequences thereof. C3a, C5a, C5b-9 activate cells to release inflammatory mediators including but not limited to; TNF-α, IL-1, PDGF, VEGF, neutrophil elastase, and other cytokines and inflammatory mediators.

"ANTIBODY," as used herein, contains two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains; CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hyper-variability, termed complementarity determining regions (CDRs), interspersed with regions that are more conserved, termed framework regions (FR). Each VH and VL is composed of three CDRs and four Frameworks arranged from amino-terminus to carboxyl-terminus in the following order: FR1, CDR1, FR2, CDR2, FR3, CDR3, FR4. The variable regions of the heavy and light chains contain a binding domain that interacts with an antigen. The term "antibody" encompasses whole antibodies and antibody fragments thereof, derived from any antibody-producing mammal (e.g., mouse, rat, rabbit, and primate including human). Exemplary antibodies include polyclonal, monoclonal and recombinant antibodies; multi-specific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

"ANTIGEN BINDING FRAGMENT" refers to a fragment of a whole antibody which binds to the same target as the whole antibody from which it was derived. Types of antibody fragments include nano bodies, diabodies, linear antibodies, single-chain antibody molecules and multispecific antibodies formed from antibody fragments. Examples of antibody fragments include Fab, Fab', F(ab)2, F(ab')2 and Fv fragments, or scFv fragments (and any PEGylated variations of any of the forgoing). Examples of antigen binding fragments include, but are not limited to:

"Fab" fragments (single chain variable regions with VH and VL);

"Monovalent Fragments" (antibody fragments consisting of the VL, VH, CL and CH1 domains);

"F(ab')2" fragments (bivalent fragments comprising two Fab fragments linked by a disulfide bridge at the hinge region);

"Fd" fragments (which consist of the VH and CH1 domains of an antibody);

"Fv" fragment (which consist of the VL and VH domains of a single arm of an antibody);

single domain antibody ("dAb"), which consist of a VH domain or a VL domain;

an isolated Complementarity Determining Region ("CDR," defined below).

"COMPLEMENTARITY DETERMINING REGIONS (CDRs)" are the key binding regions of the antibody. In a full-length antibody, there are typically three CDRs found within the variable regions of each of the two heavy and light chain variable regions.

"CHIMERIC ANTIBODY" is a recombinant protein that contains the variable domains and CDRs derived from an antibody from a non-human species of animal, while the remainder of the antibody molecule is derived from a human antibody.

"HUMANIZED ANTIBODY" is an antibody that consists of non-human CDRs and humanized framework regions. Humanized antibodies are typically recombinant proteins in which only the antibody complementarity-determining regions are of non-human origin.

A "FUNCTIONAL DERIVATIVE" of an antibody is any compound which is either taken from, or incorporates within itself, the functional region of the antibody. Functional derivatives of antibodies include, but are not limited to, antigen binding fragments (previously defined), CDRs, chimeric antibodies, monoclonal antibodies, recombinant antibodies, and single chain antibodies. CDRs (previously defined), as antigen binding fragments, can also be incorporated into single domain antibodies, maxi bodies, mini bodies, intrabodies, diabodies, triabodies, tetra bodies, v-NAR and bis-scFv. Antigen binding fragments of antibodies can be grafted into scaffolds based on polypeptides such as Fibronectin type III (Fn3). Antigen binding fragments can be incorporated into single chain molecules comprising a pair of tandem Fv segments (VH-CH1-VH-CH1) which, together with complementary light chain polypeptides, form a pair of antigen binding regions.

"Fc REGION" refers to the region of the antibody that induces effector functions (defined below).

"EFFECTOR FUNCTIONS" refer to those biological activities attributable to the native Fc region of an antibody, and vary among antibody isotypes. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. In order to minimize or eliminate side effects of a therapeutic antibody, it may be preferable to minimize or eliminate effector functions.

"REDUCED Fc EFFECTOR FUNCTION(S)" refers to the function(s) of an antibody wherein the antibody does not act against an antigen that recognizes the Fc region of the antibody. Examples of reduced Fc effector functions can include, but are not limited to, reduced Fc binding to the antigen, lack of Fc activation against an antigen, an Fc region that contains mutations to prevent normal Fc effector functions, or prevention of the activation of platelets and other cells that have Fc receptors.

"IDENTICAL," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. The percent identity between two amino acid sequences can also be determined using the algorithm of Meyers and Miller.

Treating Complement Mediated Ocular Inflammation, Hemorrhage and Fibrosis, and the Pathological Consequences Thereof Embodiments described herein relate to compositions and methods for treating a subject suffering from any ocular condition associated with retinal fibrosis, hemorrhage and/or ocular inflammation by administering to the afflicted subject an effective amount of an anti-AP antibody. The administered anti-AP antibody (e.g., anti-properdin antibody or anti-P antibody) may target any AP specific protein, and/or any antibody, which targets the PC3bB complex of the AP. Additionally, embodiments described herein include methods for treating complement mediated degenerative ocular disorders including (but not limited to) AMD and AMD-like conditions, by administering to the afflicted subject an effective amount of an anti-AP antibody.

Specific Mechanisms of AP-Mediated Ocular Pathologies

AMD & Drusen

In patients with AMD and other disorders involving deposition and accumulation of lipofuscin, drusen can build up between the Bruch's membrane and the retinal pigment epithelium (RPE) of the eye. This buildup of material causes a tear in the bruch's membrane resulting in the breakage of the blood-retinal barrier. Breakage of the blood-retinal barrier leads to choroidal neovascularization (CNV), subretinal hemorrhage, serous retinal (or retinal pigment epithelium) detachments, lipid exudates, and/or fibrovascular scar. All of these pathologies are part of one or more ocular diseases. Drusen deposits and damaged tissues are known to activate the alternative complement pathway that ultimately leads to inflammation, tissue injury, and final vision loss.

Drusen & Alternative Pathway

In the context of AMD, several inflammatory cytokines, activated microglial cells, macrophages and other inflammatory cells have been found associated with drusen. The presence of activated cells, components of activated complement pathway, and inflammatory mediators suggest activation of the alternative pathway onsite of pathology. Chronic inflammation, and the consequences thereof, can jeopardize the integrity of the retinal pigment epithelium that in turn causes photoreceptor atrophy and choroidal neovascularization (CNV). Recent findings have confirmed the role of immunologic processes in AMD pathogenesis, including the processes by which inflammatory cells and molecular mediators perpetuate inflammation in and around the Bruch's membrane. Dysregulation of complement activation results in an over production of anaphylatoxins, which activate a variety of ocular tissue cells. In the context of AMD, activated RPE cells release VEGF and recruit fibroblasts and macrophages to the site of injury, resulting in retinal fibrosis and inflammation. Chronic complement activation is the primary cause and driving force behind chronic ocular inflammation, which is the root cause of ocular disorders and pathologies.

Alternative Pathway & Inflammation

Chronic local inflammation and complement activation are inextricably involved in ocular pathologies. Our approach is to target specific molecular constituents in the complement pathway in such a way as to dampen or inhibit the eye's chronic inflammatory processes. The anti-AP antibodies described herein can be used in methods of treatment that inhibit the inflammatory processes, which cause inflammation, hemorrhage, fibrosis, and neovascularization in AMD and related ocular disorders and pathologies. The anti-AP antibodies described herein can be used to inhibit inflammation, hemorrhage, fibrosis, and neovascularization, which are associated with ocular surgery, or which are potential post-operative complications of ocular surgery.

Figure 2:
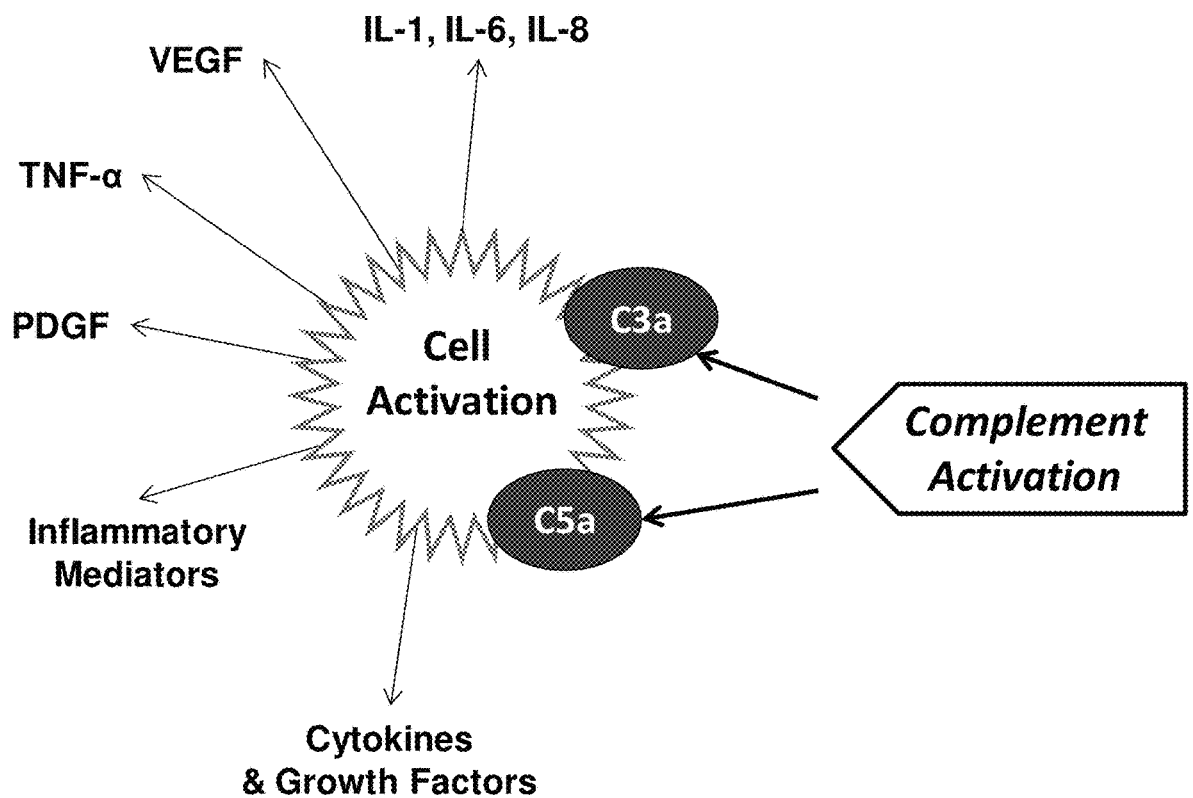
FIG. 2 is a schematic diagram of how C3a and C5a produced via the AP activate cells, which produce TNF-alpha, inflammatory mediators, growth factors, such as VEGF and PDGF, and inflammatory cytokines.

Activation of the AP of the innate immune system produces C5a and C3a, which are potent anaphylatoxins. Dysregulation of complement activation results in an over production of C5a and C3a. C5a and C3a activate retinal and immune system cells, and thereby perpetuate a cascade of complement system activity which results in chronic ocular inflammation. C5a decreases RPE cell viability and ability to suppress immune cell proliferation, resulting in over proliferation and recruitment of fibroblasts and macrophages. At the same time, C5a also increases VEGF secretion by RPE cells, which perpetuates CNV. Immune system cells bearing C3a receptors, such as monocytes, T-lymphocytes, mast cells, basophils, and microglial cells are also activated by C3a. Activated cells release inflammatory mediators such as TNF, IL-1, IL-6, IL8, VEGF, PDGF, FGF, and several other cytokines. (see FIG. 2) In order to inhibit all of these inflammatory mediators, the agents of the present invention target the AP upstream, at the point where properdin binds C3b.

Alternative Pathway & Vascular Endothelial Growth Factor (VEGF)

As previously discussed, C5a activates RPE cells to produce VEGF. The AP also activates other cells which can mediate production of VEGF. In pathological conditions where the AP is dysregulated, production of VEGF can be excessive. Thus, AP inhibition is expected to inhibit C3a and C5a production and thereby inhibit production of VEGF. Inhibition of VEGF is important in effectively inhibiting CNV and other ocular pathologies related to vascular dysfunction. By targeting the AP upstream of complement mediated VEGF production, the anti-AP antibodies described herein can provide a treatment method, which inhibits formation of VEGF without jeopardizing tissue repair.

VEGF & Neovascularization

Under normal circumstances, production of VEGF initiates new blood vessel growth and promotes healing of injured tissue. In some pathological conditions, excessive, chronic, or otherwise uncontrolled VEGF production causes an abnormal and/or excessive growth of blood vessels. It is well known within the art that uncontrolled production of VEGF plays a key role in choroidal neovascularization (CNV). When the presence of drusen or some other source of retinal injury occurs, the inflammatory processes cause a proliferation of VEGF production. In healthy tissues, this VEGF is released to promote normal new vessel growth at the site of injury. Under pathological conditions, the uncontrolled VEGF results in uncontrolled growth of abnormal vessels (also known as CNV). CNV exacerbates the injury and can directly cause loss of vision.

While VEGF is the primary cause of CNV, it promotes the formation of new healthy blood vessels. Normal formation of new vasculature is required for wound healing. Thus, an ideal treatment should only prevent the formation of pathological VEGF important for ocular pathologies. Unfortunately, anti-VEGF treatments completely deplete VEGF, while proven effective for preventing CNV, also prevent tissue repair. Similarly, any therapeutic, which completely inhibits all neovascularization will also inhibit tissue repair.

For this reason, agents, which directly neutralize VEGF are not indicated for patients undergoing ocular surgery. Lesions formed in the normal course of the ocular procedure, along with those which are inherently associated with the disease, require VEGF for normal tissue repair. Consequently, patients undergoing ocular surgery can't be treated with anti-VEGF agents.

Neovascularization & Wet AMD

Neovascular AMD, which is also referred to as "Wet AMD" or "Exudative AMD," is associated with an inadequate regulation of the complement system. Dysregulation of VEGF causes uncontrolled growth of abnormal vasculature. In advanced cases, neovascular AMD is associated with pigment epithelial detachment and subretinal hemorrhage. Currently available drugs, which neutralize VEGF can treat CNV. These therapies include anti-VEGF agents and antibodies (PCT/US12/20855), Genentech (EP070871431), and Xoma (PCT/US08/080531). Lucentis (an anti-VEGF antibody Fab) and Eyelea (VEGF receptor) are two anti-VEGF agents of the prior art. These VEGF-targeting agents are provided to Wet AMD patients for treatment and prevention of neovascularization. While these drugs are effective for preventing CNV, they do not prevent the underlying ocular inflammation, fibrosis, and vascular leakage including hemorrhage that perpetuates disease progression even in the absence of VEGF. Agents which target VEGF directly do not inhibit the AP or AP induced inflammation or tissue injury. Consequently, such agents do not prevent complement mediated inflammation, RPE destruction via MAC formation, or any other pathological manifestations of AP dysregulation. Moreover, due to their inhibitory effect on tissue repair, recent studies have shown that such agents can ultimately cause Geographic Atrophy and permanent loss of vision. Thus agents that prevent retinal fibrosis, vascular hemorrhage, and CNV are an unmet need. Such agents are needed to control further damage post VEGF treatment.

In two separate animal models of Wet AMD, it was found that the anti-AP antibodies described herein can prevent CNV, inflammation, fibrosis, and hemorrhage as well as wound healing. Laser induced CNV was created that is essentially a wound, which leads to inflammation, fibrosis, and hemorrhage. In the CNV model in rhesus, a anti-AP antibodies described herein (e.g., an anti-properdin antibody Fab) inhibited CNV. In the same study, CNV was more completely inhibited in those monkeys treated with Lucentis (an anti-VEGF antibody Fab). However, the Lucentis treated animals experienced more hemorrhaging and more fibrosis (scarring) than did the animals treated with the anti-AP antibodies.

Other embodiments described herein relate to a combination treatment for AMD, which utilizes the efficiency of an anti-VEGF treatment in the treatment of CNV, and which also utilizes an anti-AP antibody. Short-term use of an anti-VEGF agent, followed by (or concurrent with) use of an anti-AP antibody, can provide immediate effect on CNV while also addressing inflammation, tissue atrophy, returning CNV, hemorrhaging and hemorrhaging in post CNV patients further reducing vision loss.

Activation of the alternative pathway generates multiple growth factors such as VEGF and PDGF both of which have been involved in AMD pathology. Drugs which directly target either VEGF alone or both VEGF and PDGF have shown efficacy in Wet AMD. However, treatments which target both factors are more effective. Fovista is a combination therapy with anti-VEGF and anti-PDGF both of which neutralize the existing growth factors responsible for neovascularization. In some embodiments, the anti-AP antibodies can be used to prevent the formation of multiple growth factors responsible for neovascularization, fibrosis, and inflammation. There is currently no treatment for retinal fibrosis. The anti-AP antibodies described herein can block the production of both the VEGF and PDGF.

Alternative Pathway and Tissue Injury

Complement pathway activation leads to the formation of MAC (C5b-9). As previously described, and as presented schematically in FIG. 1 and FIG. 2, once the AP is activated it will lead to inflammatory cell activation and MAC formation. MAC-mediated RPE activation, is important for vision loss in AMD and other ocular pathologies. Fragments of destroyed RPEs have been found in drusen, along with complement system proteins, including MAC. Knockout studies, wherein study subjects are unable to form functional MAC via the AP, provide evidence of the role of the AP in tissue damage, demyelination, reduced inflammatory cell infiltrate, and improved functional recovery.

Tissue Injury & Geographic Atrophy

Geographic Atrophy (GA) is an advanced form of Dry AMD. In the course of AMD disease progression, as drusen enlarge and complement driven inflammation proliferates out of control, ocular tissues suffer from both physical and physiological damage. Drusen can put physical pressure and cause oxidative stress on these cells while complement driven MAC formation causes cell lysis and death. Further aggravating the situation, the release of inflammatory mediators causes vascular permeability, which causes edema, hemorrhaging and other vascular pathologies. The culmination and accumulation of these physical and physiological assaults on the RPE cells ultimately lead to irreversible loss of retinal epithelial tissue. The retinal pigment epithelium lies beneath the photoreceptor cells, and provides critical metabolic support for the light-sensing cells of the eye. Loss of RPE tissue results in loss of photoreceptor cells and loss of vision. Combination of these events lead to various ocular pathologies.

There is no currently available FDA approved treatment for many ocular pathologies. Lampalizumab is an anti-factor D antibody, which has shown positive data in phase II trial in GA patients. This drug is indicated only for GA and does not control CNV, retinal fibrosis, or hemorrhage. The anti-AP antibodies described herein can inhibit retinal fibrosis, vascular hemorrhage, and inflammation beyond what Lampalizumab can do despite being drugs of the same class. The anti-AP antibodies described herein prevent formation of the inactive complex of C3 convertase compared to Lampalizumab, which does not prevent the formation of the inactive C3 complex PC3bB. Thus, the invention acts at a step of the AP which is up-stream of Lampalizumab's mechanism of action.

Alternative Pathway & Retinal Fibrosis

Fibrosis is associated with old or chronic lesions within the eye. It has been shown that when subjects with Wet AMD are treated with Ranibizumab they ultimately develop fibrosis followed by unexpected vision loss that has been recently identified. CNV, tissue atrophy, and fibrosis cause degeneration of the macula. Bevacizumab treated eyes were evaluated for fibrosis, tissue atrophy, subretinal hemorrhage, extent of CNV, and pigment epithelial detachment (PED). Size and grading of CNV leakage on fluorescein angiography were also evaluated. In a retrospective study, central retinal PED, and subretinal fluid (SRF) thickness was evaluated using optical coherence tomography. Other factors predicting a large lesion were subfoveal and bilateral lesions and the presence of hemorrhage at baseline. A large and bilateral lesion and hemorrhage at baseline were correlated with subretinal fibrosis at follow-up.

Retinal fibrosis can also result from injury and trauma to the eye tissue. The injury or trauma can result from many sources. Moreover, chronic inflammation can also cause retinal fibrosis. It has been shown that at the site of the initial tissue damage, there is often infiltration of inflammatory cells which ultimately develops into scar tissue.

One potential mechanism of fibrosis is the production of cytokines, which activate and recruit fibroblasts. Activated fibroblasts produce more cytokines and other inflammatory mediators, and assist in the recruitment and activation of immune cells, such as macrophages, which play a role in fibrosis and inflammation. Fibroblasts also mediate production of VEGF. Thus, fibrotic scars, although necrotic in nature, can also be vascularized. Fibrosis is a complex process and anti-VEGF therapy cannot control fibrosis or vascular leakage. We present a surprising discovery that anti-AP antibodies described herein can prevent the formation and persistence of fibrotic scars untreated by an anti-VEGF treatment.

Alternative Pathway and Diabetic Retinopathy

Studies have demonstrated that complement mediated inflammatory cytokines play a key role in the progression of diabetic retinopathy. In particular, VEGF has been shown to play a critical role in the breakdown of the blood-retinal barrier and the resulting macular edema. Anti-VEGF (VEGF-targeting) agents have proven effective in treating and preventing progression of diabetic retinopathy. The administration of anti-AP antibodies described herein can prevent formation of inflammatory cytokines and inhibit formation of VEGF. Accordingly, the invention will be able to effectively treat diabetic retinopathy.

Alternative Pathway and Other Ocular Diseases

Dysregulation of the AP within the eye results in a myriad of ocular pathologies, of which AMD and Diabetic Retinopathy are only two. Dysregulation of the AP in other organs and tissues also causes another range of pathologies. The leading cause of blindness in the developed world results from several disorders that have pathologic ocular inflammation and neovascularization as the common pathway leading to vision loss. These disorders include exudative age related macular degeneration (AMD), diabetic retinopathy (DR), retinopathy of prematurity (ROP), retinal vein occlusions (RVO) and ocular tumors. Dysregulation of the AP within the eye results in a myriad of ocular pathologies. Dysregulation of the AP in other organs and tissues also causes another range of pathologies in the ocular space. In the context of the eye, dysregulation of the AP can be implicated in: a) AMD-like diseases, including congenital and familial drusen; b) autoimmune uveitis and uveitis secondary to autoimmune disorder, including macular edema; c) retinal ischemia and ocular pathologies associated with or caused by retinal ischemia, including hypertensive retinopathy and retinopathy of prematurity; and, d) inflammatory pathologies of the anterior segment of the eye.

Drusen and AMD-Like Diseases

Several congenital and familial disorders are characterized by the deposition of drusen and lipofuscin deposits. Such disorders include Sorsby's fundus dystrophy, Doyne Honeycomb Retinal Dystrophy, Malattia Leventinese, Familial Dominant Drusen, North Carolina macular dystrophy, Juvenile Macular degeneration, Stargardt's disease, Vitelliform Macular Dystrophy, Adult-Onset Foveomacular Vitelliform Dystrophy (AOFVD), Sorsby's fundus dystrophy, and Best's Disease. Disorders and pathologies characterized by excessive deposition of drusen result in macular degeneration and CNV in much the same way as does AMD. Drusen and lipofuscin deposits initiate an inflammatory response and put oxidative stress on ocular tissues. Inflammatory mediators and cytokines proliferate as a consequence of dysregulated AP activation. Production of VEGF causes neovascularization, edema and hemorrhaging. Formation of MAC causes tissue damage and atrophy. Recruitment of fibroblasts leads to fibrosis.

Anti-VEGF agents have proven effective against neovascularization associated with AOFVD and Malattia Leventinese (Honeycomb Retinal Dystrophy). In case reports, anti-VEGF agents have demonstrated an ability to treat neovascularization in association with the deposition of drusen. The invention inhibits formation of inflammatory cytokines and inhibits formation of VEGF. Accordingly, the invention will be able to effectively treat neovascularization associated with deposition of drusen.

Deposition of drusen is known to cause ocular inflammation and AP activation, the release of inflammatory cytokines, and associated inflammatory pathologies. The anti-AP antibodies described herein can inhibit the AP and thereby inhibit the release of inflammatory cytokines and associated inflammatory pathologies.

Autoimmune Uveitis, and Uveitis Secondary to Autoimmune Disorder

Autoimmune uveitis is the result of dysregulated inflammation in the eye. These conditions include, but are not limited to, Iritis, Pars planitis, Choroiditis, Chorioretinitis, Anterior uveitis, Posterior uveitis, and Scleritis. Several autoimmune disorders, including several, which primarily affect other organs of the body, which are not necessarily associated with AMD, sometimes have inflammation based ocular complications include PNH, polycystic kidney disease, rheumatoid arthritis, Lupus, and others.

For example, uveitis is a common symptom in patients suffering from Behçet's Disease, an autoimmune disorder affecting small vessel vasculature. Patients with Behcet's Disease benefit from treatment with Infliximab (trademarked as Remicade), which is a TNF-alpha inhibitor. The anti-AP antibodies described herein can prevent the formation of AP-mediated TNF-alpha and can provide a similar benefit to patients with Behcet's Disease who are suffering from uveitis.

Eales disease (also known as angiopathia retinae juvenilis, periphlebitis retinae, and/or primary perivasculitis of the retina) is an idiopathic autoimmune disorder characterized by retinal vasculature occlusion and ocular inflammation. Neovascularization and recurrent retinal and vitreal hemorrhaging are hallmarks of Eale's disease. Treatment with anti-VEGF agents is effective for treating neovascularization associated with an inflammatory response to oxidative stress resulting from vascular occlusion. Accordingly, the invention will provide a benefit by inhibiting production of VEGF. Additionally, the anti-AP antibodies described herein can provide a further benefit by inhibiting production of several other inflammatory cytokines and mediators, including TNF-alpha.

Retinal Ischemia (and Associated Ocular Pathologies)

In the case of vascular occlusion disorders, oxidative stress is caused by a lack of sufficient circulation to the retina. This oxidative stress causes alternative pathway activation, which results in uveitis, ocular edema and neovascularization. Vascular occlusion disorders, which cause inflammatory ocular pathologies include, but are not limited to Central retinal vein occlusion (CRVO), occlusive peripheral arterial disease, ocular ischemic syndrome secondary to atherosclerosis, retinal artery occlusion secondary to antiphospholipid syndrome, neovascular glaucoma, rubeosis iridis, and Purtscher's retinopathy. These are all conditions where vascular pathology and/or vascular occlusion has demonstrated a potential to cause CNV and/or ocular tissue degeneration due to oxidative stress on ocular tissues and the resulting inflammatory response. Treatment with anti-VEGF agents is effective for treating neovascularization associated with an inflammatory response to oxidative stress resulting from various vascular occlusion pathologies.

Hypertensive retinopathy is caused by oxidative stress, inflammation, and neovascularization of retinal tissue caused by the pathological effects of chronic hypertension on small blood vessels of the eye. Chronic hypertension is also known to cause retinal arterial macroaneurysm. Retinal arterial macroaneurysms can also be treated with anti-VEGF treatments. The anti-AP antibodies described herein can inhibit ocular inflammation and VEGF mediated neovascularization and can be expected to provide therapeutic benefit to patients with hypertensive retinopathy and/or retinal arterial macroaneurysms associated with chronic hypertension.

Oxidative stress can also be caused by premature retinal vasculature. Retinopathy of prematurity is a condition wherein a pre-mature infant is born before the vasculature of the retina has had time to fully develop. Similarly, familial exudative vitreoretinopathy is a disorder, not associated with pre-mature birth, wherein the vasculature of the retina has not completely matured. In both of these conditions, the lack of fully matured retinal vasculature causes oxidative stress of the retina, followed by inflammation and neovascularization similar to that see in association with AMD.

Inflammatory Pathologies of the Anterior Segment of the Eye

AP mediated inflammation has also been implicated in the pathogenesis of the anterior segments of the eye, such as anterior autoimmune uveitis. Neovascular glaucoma and corneal neovascularization are inflammatory pathologies of the anterior eye. Anti-VEGF agents have demonstrated an ability to treat neovascular glaucoma and corneal neovascularization in the anterior regions of the eye. Accordingly, the invention will provide a benefit by inhibiting production of VEGF. Additionally, the anti-AP antibodies described herein can provide a further benefit by inhibiting ocular inflammation, inhibiting MAC formation, and inhibiting production of other inflammatory cytokines and mediators.

Fuchs' corneal endothelial dystrophy (FCED) is a degenerative disease of the corneal endothelium which ultimately leads to conical edema and loss of vision. While the pathogenesis of FCED remains only partially understood, inflammation and edema is known to play a key role in disease progression. Moreover, recent studies support the role of complement system activation. The anti-AP antibodies described herein can treat FCED by inhibiting complement driven inflammation and edema in the cornea.

Limitations of Treatment in AMD—in Light of New Treatments Required

Anti-VEGF treatments only control neovascularization and have no effect on the underlying inflammatory processes which cause uveitis, edema, hemorrhage and fibrosis. Due to their indiscriminate inhibition of new vessel group, anti-VEGF are contraindicated for tissue repair, and especially in cases where a patient is undergoing surgical procedure. Healthy new vessel growth is required for tissue repair. Unfortunately, anti-VEGF agents inhibit all new vessel growth, and thereby inhibit tissue repair.

Controlling AP Mediated Inflammation, Fibrosis, and Retinal Hemorrhage

Two potent anaphylatoxins are produced as a result of AP activation, C3a and C5a. Complement activation leads to the formation of both C3a and C5a. Both anaphylatoxins activate inflammatory cells too release a variety of inflammatory mediators. TNF and IL-1 are two such inflammatory mediators, both of which have been shown to be potent regulators of inflammation. VEGF and PDGF are two angiogenic molecules, which are also released from ocular cells in response to inflammation and AP activation. The C3a molecule has a high affinity for C3a receptors (C3aR). C3aRs are present on neutrophils, monocytes, platelets, mast cells, T lymphocytes, retinal epithelial cells, and other cells. Upon activation, these cells produce inflammatory mediators, growth factors, peroxides and proteases that can cause and/or exacerbate disease pathology. Similar to C3a, C5a also causes the release of inflammatory mediators relevant to several ocular pathologies and related ocular diseases. C5a is known to activate a variety of ocular and non-ocular cells. For example, C5a is known to activate RPEs to produce/release VEGF, which has a well established role in CNV. Thus, inhibition of C3a and C5a production is essential for the treatment of any ocular pathology associated with inflammation, fibrosis, and retinal hemorrhage, wherein these inflammatory mediators have devastating consequences (such as CNV, tissue degeneration, and vision loss) for the affected ocular tissues and cells.

C5a production is concurrent with C5b production (as C5 is cleaved into C5a and C5b). C5b molecules insert into the lipid bilayer of a cell to initiate the formation of C5b-9 or sC5b-9 (MAC). C5b-9 is a complex that forms on the cell surface and causes tissue injury. Integration of C5b-9 into the cell membrane causes cell lysis, and death, resulting in tissue injury and degradation. In the context of AMD, MAC formation results in lysis of RPE cells and damage to the rods and cones of the eye. This tissue destruction, if left untreated, commonly leads to mild to severe vision loss and potentially blindness. The anti-AP antibodies described herein can prevent AP dependent cell lysis via MAC formation by inhibiting the formations of C3a, C3b, C5a, C5b, and C5b-9.

Anti-AP antibodies described herein, which prevent AP activity, can prevent C3a and C5b production, inflammation, VEGF production, and MAC formation. Thus, anti-AP antibodies, including anti-P antibodies, can be used to treat ocular pathologies associated with inflammation, fibrosis, retinal hemorrhage, CNV, and tissue degeneration.

Anti-AP Antibodies

The anti-AP antibodies can include any antibody or antigen binding fragment thereof that targets an AP specific protein or protein complex and inhibits alternative complement AP activation. In some embodiments, the anti-AP antibodies or fragments thereof can inhibit alternate complement pathway activation without inhibiting or affecting classical pathway complement activation. The anti-AP antibodies described herein can be used for the treatment of ocular Inflammation, Fibrosis, retinal hemorrhage, CNV, and tissue degeneration.

Anti-C3b Antibodies

In one embodiment, the anti-AP antibody described herein can be an anti-C3b antibody or antigen binding fragment thereof. C3b is a large protein and therefore multiple antibodies can be produced against various segments of this protein. There exist multiple sites where-on an antibody might bind and inhibit the protein's activity in any variety of ways. Depending on how and where an antibody binds to C3b, the effect of that antibody could range from inconsequential to complete inhibition.

The anti-C3b antibodies can include those that bind to C3b in such a way as to prevent the interaction of C3b with Factor B. The effect of these antibodies is necessarily isolated to the alternative pathway since no such interaction exists within the classical pathway. These antibodies prevent the formation of C3a/C3b, C5a/C5b, and C5b-9/sC5b-9 critical for pathological outcome causing disease initiation and progression. Inhibition of the formation of each of these molecules, by the alternative pathway, has significant physiological consequences. Inhibition of alternative pathway produced C3b (herein referred to as "aC3b") impacts extravascular hemolysis of erythrocytes. The C3b produced by the classical pathway is not inhibited by these antibodies and therefore is required for opsonization of foreign particles/bacteria that are coated with CP produced C3b (herein referred to as "cC3b"). The inhibition of C3a formation has direct effect on monocytes activation and production of TNF-$\alpha$ which is a validated marker of inflammation.

Anti-Properdin Antibodies

In another embodiment, the anti-AP antibody described herein can be an anti-properdin antibody or antigen binding fragment thereof. As is the case with C3b, properdin is a large protein with many potential sites where antibodies can bind. Different antibodies binding in different ways and/or on different sites of the Properdin protein, will inhibit either amplification loop of the classical pathway or alternative pathway. Properdin is known to be part of the amplification loop of the classical pathway. Thus, classical pathway activation can be dampened by the use of specific anti-properdin antibodies that inhibit the amplification loop (e.g., U.S. Pat. No. 6,333,034). Some antibodies can inhibit the classical pathway activation where interactions of properdin to C3b, within the classical pathway, become important for classical pathway amplification.

Properdin binds to itself and generates aggregates. Depending upon the configuration of the aggregate, antibodies binding properdin can bind mono, di-, tri- and tetramer, with each generating different responses. Thus antibody-to-properdin ratio can be 1:1, 1:2, 1:3, and 1:4. This means that an antibody can bind in any configuration.

Properdin is involved directly in the AP activation but indirectly in classical pathway activation via the amplification loop in vivo. Also, properdin binds both C3b and C5b. An antibody which disrupts properdin's interaction with C3b may or may not interrupt properdin's interaction with C5b (and vice versa). Antibodies that prevent one or both may be of distinguishable clinical significance.

Thus, some antibodies targeting properdin a) inhibit both the classical pathway and alternative pathway, or b) inhibit the alternative pathway alone.

In some embodiments, the anti-AP antibody can be an anti-properdin antibody that is directed to or specifically binds to domains on properdin that are involved in controlling properdin function. The anti-properdin antibodies or fragments thereof can inhibit alternate complement pathway activation without inhibiting or effecting classical complement activation as well as inhibit binding of properdin (oligomer/monomer) to C3b, inhibit binding of properdin to factor B, inhibit properdin binding to C3bB complex, inhibit factor D cleavage of factor B, reduce half life of the C3 convertase, prevent oligomerization of properdin monomers by blocking the N terminus of properdin, which associates with TSR6 to generate oligomers, inhibit the binding of properdin to C5 or C5b, reduce the formation of membrane attack complex C5b-9, reduce the formation of anaphylatoxins, for example C3a and/or C5a, reduce the formation of C3b, reduce the activation of neutrophils, monocytes and platelets, and/or reduce leukocyte aggregate formation.

The amino acid sequences of mammalian properdin are known. For example, the amino acid sequence of human properdin is disclosed in the GenBank database under Accession No. AAA36489. Human properdin is a 469 amino acid protein that includes a signal peptide (amino acids 1-28), and six, non-identical thrombo spondin type 1 repeats (TSR) of about 60 amino acids each, as follows: amino acids 80-134 (TSR1), amino acids 139-191 (TSR2), amino acids 196-255 (TSR3), amino acids 260-313 (TSR4), amino acids 318-377 (TSR5), and amino acids 382-462 (TSR6).

In some embodiments, the anti-properdin antibodies can bind to a specific epitope located on properdin to inhibit AP activation. In one example, the anti-properdin agent can bind to the N-terminal domain of properdin to inhibit the binding of properdin to C3b. In other embodiments, the anti-properdin antibodies can bind to the N-terminal segment spanning into the TSR1 of properdin.

The anti-properdin antibody can also inhibit the level of functional properdin in a mammalian host. Functional properdin means properdin molecules capable of activating the alternative pathway.

In another aspect, the anti-properdin antibody can bind properdin with high affinity, inhibit oligomerization of properdin, inhibit factor D mediated cleavage of factor B in a C3bB complex, not inhibit the classical complement pathway, prevent alternative complement pathway activation, inhibit C3a, C5a, and C5b-9 formation, Inhibit neutrophil, monocyte and platelet activation. Inhibit leukocyte platelet conjugate formation.

Anti-Ba Antibodies

In other embodiments, the anti-AP antibody described herein can be an anti-Ba antibody or antigen binding fragment thereof. The protein Ba (cleaved from Factor B) is a large protein with a molecular weight of approximately 33,000. Thus, like Properdin and C3b, any of a multitude of antibodies can be produced against various protein motifs of, and locations on, the protein. With this protein, as with the other proteins of the AP, the anti-Ba antibodies bind to the protein in such a way so as to inhibit the formation of C3a, C3b, C5a, C5b, and C5b-9.

Anti-Bb Antibodies

In still other embodiments, the anti-AP antibody described herein can be an anti-Bb antibody or antigen binding fragment thereof. The protein Bb (cleaved product of Factor B) is a large protein with a molecular weight of approximately 64,000. Anti-Bb antibodies bind Bb and factor B, but not Ba as the target antigen. In some embodiments, the anti-factor Bb antibody binds the Bb fragments, does not bind Ba fragment, does not inhibit the factor B binding to C3b, inhibits C3b production, inhibits C3a, C5a, and C5b-9 formation and inhibits lysis of rabbit erythrocytes. The anti-Bb antibodies can prevent the formation of C3a, C3b, C5a, C5b, and C5b-9 by the alternative pathway at a juncture not shared with the classical pathway. Inhibition of formation of each of these molecules has physiologic consequences. The anti-Bb antibody can also inhibit oligomerization of C3b. The molecular weight of native C3 is in the order of 190 kDa, upon cleavage by the convertase, C3 is converted into a C3a (10 kDa) and C3b (180 kDa). This C3b molecule has high affinity for properdin oligomers, as a result forms a complex containing 3 C3b molecules attached to a properdin trimer. Anti-Bb antibodies described herein can prevent formation of additional molecules of C3b and therefore result in a complex where C3b oligomer will not form. If C3b formation is completely prevented, properdin will float alone without any C3b attached. Properdin does not bind C3 or the isoforms of C3b.

Inhibition of C3b (aC3b) will impact extravascular hemolysis. Inhibition of C3a and C5a will impact cellular activation and subsequent release of inflammatory mediators. Inflammatory mediators, when over-produced, can cause any number of disease pathologies in humans. In so doing, these antibodies also prevent the formation of well known markers of inflammation, such as TNF-α and IL-1.

In some embodiments, the anti-Bb antibody can bind to the serine protease domain and particularly the catalytic triad of serine protease of the Bb region. The serine protease domain forms the third and the last domain of intact factor B. The serine protease domain carries the catalytic site, which is solely responsible for C3 cleavage. While the catalytic site is exposed in both intact factor B and the Bb fragment, it becomes active only after the Ba is cleaved off by factor D. In other embodiments, the anti-factor Bb antibody can bind the catalytic triad and prevent its activity by either locking the inactive conformation in place or by binding to the region where factor D cleaves the factor B.

Table 1 and Table 2 lists the amino acid sequences of the heavy and light chain variable domains or regions of anti-C3b, anti-P, anti-Ba, and anti-Bb antibodies that can be used as anti-AP antibodies in the methods described herein. The Tables identify the heavy chain and light chain CDR1s, CDR2s and CDR3s of the antibodies as well as the framework regions. Accordingly, aspects of the application described herein, relate to an isolated monoclonal antibody, or antigen binding portion thereof comprising: (a) a heavy chain variable region comprising CDR1, CDR2, and CDR3, of the respective antibodies; and (b) a light chain variable region comprising CDR1, CDR2, and CDR3 of the respective antibodies.

Table 3 lists examples of complete amino acid sequences of the heavy and light chains of anti-C3b, anti-P, and anti-Bb antibodies that can be used in the methods described herein. The heavy and light chains include the CDRs of the heavy and light chain variable regions listed in Tables 1 and 2.

TABLE 1

| | TARGET | SPECIES | SEQUENCE | FW1 | CDR1 | FW2 | CDR2 | FW3 | CDR3 | FW4 |
|---|---|---|---|---|---|---|---|---|---|---|
| L-1 | Bb | Rabbit | 1 | AVVLT QTASP VSGVV GGTVT INC | QASENI YSRLA | WYQQ KPGQP PRVLI Y | YASDLA S | GVPSRFG GSGSGTD YTLTISDL ECADAAT YYC | HSYY WNSA YSDNT | FGGG TEVV VEG |
| L-2 | P | Rabbit | 2 | AYDLT QTPAS VEAAV GGTVT INC | QASDNI YSLLA | WYQQ KPGQP PKLLIY | RASTLA S | GVPSRFK GSGSGTQ FTLTISGV ECADAAT YYC | QQHY DYNYL DVA | FGGG TEVV VKG |
| L-3 | P | Rabbit | 3 | AYDLT QTPAS VEAAV GGTVT INC | QASDNI YSLLA | WYQQ KPGQP PKLLIY | RASTLA S | GVPSRFK GSGSGTQ FTLTISGV ECADAAT YYC | QQHY DYNYL DVA | FGGG TEVV VKG |
| L-4 | P | Rabbit | 4 | AYDM TQTPF SVSAA VGGTV TINC | QASQNI YSNLA | WYQQ KPGQR PKLLIY | RASTLA S | GVPSRFSG SRSGTQFT LTISGVEC ADAATYY C | QQHW DYDYI DVA | FGGG TEVV VKG |
| L-5 | Bb | Rabbit | 5 | DVVM TQTPS SVEAA VGGTV TIKC | QASENI YSYLA | WYQQ KPGQP PKLLIY | KASYLA S | GVSSRFK GSGSGTEF TLTISDLE CADAATY C | LSTIAS ASNFD A | FGGG TEVV VKG |
| L-6 | Bb | Rabbit | 6 | DPVLT QTASS VSAPV GGTVT ISC | QSSQSV YRSNN VA | WYQQ KPGKP PKLLIY | EASSLAS | GVPSRFT GSGSGTQ FTLTISGV QCDDAAT YYC | AGGYS SSVDF FFA | FGGG TEVV VKG |
| L-7 | P | Mouse | 7 | DIVMT QSHKF MSTSV GDRVS ISC | KASQD VSDAV A | WFQQ KPGQS PKLLIY | SPSYRY T | GVPDRFT GSGSGTD FTFTISSV QAEDLAV YYC | QQHYS TPWT | FGGG TKLEI KR |
| L-8 | P | Humanized | 8 | DIQMT QSHKF MSTSV GDRVT ITC | KASQD VSDAV A | WFQQ KPGKS PKLLIY | SPSYRY T | GVPSRFT GSGSGTD FTFTISSV QAEDLAV YYC | QQHYS TPWT | FGQG TKLEI K |
| L-9 | P | Humanized | 9 | DIQMT QSHKF MSTSV GDRVS ISC | KASQD VSDAV A | WFQQ KPGKS PKLLIY | SPSYRY T | GVPSRFT GSGSGTD FTFTISSV QAEDLAV YYC | QQHYS TPWT | FGQG TKLEI K |

TABLE 1-continued

| | TARGET | SPECIES | SEQUENCE | FW1 | CDR1 | FW2 | CDR2 | FW3 | CDR3 | FW4 |
|---|---|---|---|---|---|---|---|---|---|---|
| L-10 | P | Humanized | 10 | DIQMT QSPSSL STSVG DRVTI TC | KASQD VSDAV A | WFQQ KPGKA PKLLIY | SPSYRY T | GVPSRFT GSGSGTD FTFTISSV QAEDLAV YYC | QQHYS TPWT | FGQG TKLEI K |
| L-11 | P | Humanized | 11 | DIQMT QSPSSL SASVG DRVTI TC | QASQDI SNYLN | WYQQ KPGKA PKLLIY | DASTLE T | GVPSRFSG SGSGTDFT FTISSLQP EDIATYY C | QNYD NLPLT | FGGG TKVEI KR |
| L-12 | P | Humanized | 12 | DIQMT QSPSSL SASVG DRVTI TC | RASQNI SSFLN | WYQQ KSGKA PKLLIF | ATSRLQ S | GVPSRISG SGSGTDFT LTISGLQP EDFATFY C | QQSYS IPLT | FGGG TKVDI KR |
| L-13 | P | Humanized | 13 | DIQMT QSPSSL SASVG DRVTI TC | RASQGI SNYLA | WYQQ KPGKV PKLLIY | AASTLQ S | GVPSRFSG SGSGTDFT LTISSLQP EDVATYY C | QKYDS APWT | FGQG TKVEI KR |
| L-14 | P | Humanized | 14 | DIQMT QSPSSL SASVG DRVTI TC | RASQDI SFFLN | WYLQ KPGQS PQLLIY | YTSRYH S | GVPSRFSG SGSGTEFT LTISSLQP DDFATYY C | QHGNT LPWT | FGQG |
| L-15 | P | Humanized | 15 | DIQMT QSPSSL SASVG DRVTI TC | RASQDI SFFLN | WYQQ KPGKA PKLLIY | YTSRYH S | GVPSRFSG SGSGTEFT LTISSLQS EDFAVYY C | QHGNT LPWT | FGQG |
| L-16 | P | Humanized | 16 | EIVMT QSPAT LSVSP GERAT LSC | RASQDI SFFLN | WYQQ KPGKA PKLLIY | YTSRYH S | GVPSRFSG SGSGTDFT FTISSLQP EDIATYY C | QHGNT LPWT | FGQG |
| L-17 | P | Humanized | 17 | EIVLT QSPAT LSLSP GERAT LSC | RASQDI SFFLN | WFQQ RPGQS PRRLIY | YTSRYH S | GIPPRFSG SGYGTDF TLTINNIE SEDAAYY FC | QHGNT LPWT | FGQG |
| L-18 | P | Humanized | 18 | EIVMT QSPAT LSVSP GERAT LSC | RASQDI SFFLN | WYQQ KPGKA PKLLIY | YTSRYH S | GVPSRFSG SGSGTDFT FTISSLQP EDIATYY C | QHGNT LPWT | FGQG |
| L-19 | P | Humanized | 19 | DIQMT QSPSSL SASVG DRVTI TC | RASQDI SFFLN | WYLQ KPGQS PQLLIY | YTSRYH S | GVPSRFSG SGSGTEFT LTISSLQP DDFATYY C | QHGNT LPWT | FGQG |
| L-20 | P | Humanized | 20 | DIQMT QSPSSL SASVG DRVTI TC | RASQDI SFFLN | WYQQ KPGKA PKLLIY | YTSRYH S | GVPSRFSG SGSGTEFT LTISSLQS EDFAVYY C | QHGNT LPWT | FGQG |
| L-21 | P | Humanized | 21 | DIQMT QSPSSL SASVG DRVTI TC | RASQDI SFFLN | WYQQ KPGKA PKLLIY | YTSRYH S | GVPSRFSG SGSGTEFT LTISSLQS EDFAVYY C | QHGNT LPWT | FGQG |
| L-22 | P | Humanized | 22 | DIQMT QSPSSL SASVG DRVTI TC | RASQDI SFFLN | WYQQ KPGKA PKLLIY | YTSRYH S | GVPSRFSG SGSGTEFT LTISSLQS EDFAVYY C | QHGNT LPWT | FGQG |

TABLE 1-continued

| | TARGET | SPECIES | SEQUENCE | FW1 | CDR1 | FW2 | CDR2 | FW3 | CDR3 | FW4 |
|---|---|---|---|---|---|---|---|---|---|---|
| L-23 | P | Humanized | 23 | DIQMTQSPSSLSASVGDRVTITC | RASQDISFFLN | WYQQKPGKAPKLLIY | YTSRYHS | GIPPRFSGSGYGTEFTFTISSLEAEDAATYYC | QHGNTLPWT | FGQG |
| L-24 | P | Humanized | 24 | EIVMTQSPATLSVSPGERATLSC | RASQDISFFLN | WYQQKPGKAPKLLIY | YTSRYHS | GVPSRFSGSGSGTDFTFTISSLQPEDIATYYC | QHGNTLPWT | FGQG |
| L-25 | P | Humanized | 25 | DIQMTQSPSSLSASVGDRVTITC | RASQDISFFLN | WYQQKPGKAPKLLIY | YTSRYHS | GVPSRFSGSGSGTEFTLTISSLQSEDFAVYYC | QHGNTLPWT | FGQG |
| L-26 | P | Mouse | 26 | DIQMTQTTSSLSASLGDRVTISC | RASQDISFFLN | WYQQKPDGTVKLLIY | YTSRYHS | GVPSRFSGSGSGTDFSLTINNLEQEDFATYFC | QHGNTLPWT | FGGGTKLEIKR |
| L-27 | P | Humanized | 27 | DIQMTQSPSSLSASVGDRVTITC | RASQDISFFLN | WYQQKPGKAPKLLIY | YTSRYHS | GVPSRFSGSGSGTEFTLTISSLQSEDFAVYYC | QHGNTLPWT | FGQG |
| L-28 | P | Humanized | 28 | DIQMTQSPSSLSASVGDRVTITC | RASQDISFFLN | WYLQKPGQSPQLLIY | YTSRYHS | GVPSRFSGSGSGTEFTLTISSLQPDDFATYYC | QHGNTLPWT | FGQG |
| L-29 | P | Humanized | 29 | EIVMTQSPATLSVSPGERATLSC | RASQDISFFLN | WYQQKPGKAPKLLIY | YTSRYHS | GVPSRFSGSGSGTDFTFTISSLQPEDIATYYC | QHGNTLPWT | FGQG |
| L-30 | P | Humanized | 30 | DIQMTQSPSSLSASVGDRVTITC | RASQDISFFLN | WYQQKPGKAPKLLIY | YTSRYHS | GIPPRFSGSGYGTEFTFTISSLEAEDAATYYC | QHGNTLPWT | FGQG |
| L-31 | P | Humanized | 31 | DIQMTQSPSSLSASLGDRVTITC | RASQDISFFLN | WYQQKPDGTVKLLIY | YTSRYHS | GVPSRFSGSGSGTDFTLTISSLQPEDFATYFC | QHGNTLPWT | FGQGTKLEIKR |
| L-32 | P | Humanized | 32 | DIQMTQSPSSLSASLGDRVTITC | RASQDISFFLN | WYQQKPDGTVKLLIY | YTSRYHS | GVPSRFSGSGSGTDFTLTISSLQPEDFATYFC | QHGNTLPWT | FGQGTKLEIKR |
| L-33 | P | Mouse | 33 | KEIHQAGKGIKMKSQTQVFVFLLLCVSGAHGSIVMTQTPKFLLVSAGDRITITC | KASQSVNNDVA | WYQQKPGQSPKLLIY | YASNRYT | GVPDRFTGSGYGTDFTFTITTVKAEDLAVYFC | QQDYSPLT | FGAGTKLELKRADAAPTVSACTKGEFAA |
| L-34 | P | Mouse | 34 | DIQMTQTTSSLSASLGDRVTISC | RASQDISFFLN | WYQQKPDGTVKLLIY | YTSRYHS | GVPSRFSGSGSGTDFSLTINNLEQEDFATYFC | QHGNTLPWT | FGGG |

TABLE 1-continued

| | TARGET | SPECIES | SEQUENCE | FW1 | CDR1 | FW2 | CDR2 | FW3 | CDR3 | FW4 |
|---|---|---|---|---|---|---|---|---|---|---|
| L-35 | Bb | Mouse | 35 | DVQITQSPSYLAASPGETITIN | RASKSISKYLA | WYQDKPGKTNKLLIY | SGSTLQS | GIPSRFSGSGSGTDFTLTISSLEPEDFAMYYC | QQHDEYPWT | FGGGTKLEIKR |
| L-36 | Bb | Humanized | 36 | DVQITQSPSTLSASPGDRITITC | RASKSISKYLA | WYQDKPGKTNKLLIY | SGSTLQS | GIPSRFSGSGSGTEFTLTISSLQPDDFAMYYC | QQHDEYPWT | FGQGTKLEIKR |
| L-37 | Bb | Humanized | 37 | DVQITQSPSYLSASPGDTITITC | RASKSISKYLA | WYQDKPGKTNKLLIY | SGSTLQS | GIPSRFSGSGSGTEFTLTISSLQPDDFAMYYC | QQHDEYPWT | FGQGTKLEIKR |
| L-38 | C3b | Mouse | 38 | QIVLTQSPAILSASPGEKVTMTC | SATSSITYIH | WYQQKSGTSPKRWIY | GVPTRFS | DTSRLAGSGSGTSYSLTISTMEAEDAATYYC | QQWSSNPPT | FGGGTKLEIKR |
| L-39 | C3b | Humanized | 39 | EIVLTQSPATLSASPGEKVTMTC | SATSSITYIH | WYQQKSGQSPKRWIY | DTSRLAS | GVPSRFSGSGTSYSLTISTMEAEDAATYYC | QQWSSNPPT | FGGGTKLEIK |
| L-40 | C3b | Humanized | 40 | EIVLTQSPATLSASPGEKVTMTC | SATSSITYIH | WYQQKSGTSPKRWIY | DTSRLAS | GVPARFSGSGSGTSYSLTISTMEAEDAATYYC | QQWSSNPPT | FGGGTKLEIK |
| L-41 | C3b | Humanized | 41 | EIVLTQSPATLSASPGEKVTMTC | SATSSITYIH | WYQQKPGQAPKRWIY | DTSRLAS | GVPARFSGSGSGTSYSLTISTMEAEDFATYYC | QQWSSNPPT | FGGGTKLEIK |
| L-42 | P | Humanized | 42 | DIQMTQSPSSLSASVGDRVTSTC | RASQDISNYLA | WYQQKPGKVPKLLIY | AASTLQS | GVPSRFSGSGSGTDFTLTISSLQPEDVATYYC | QKYNSAPWT | FGQGTKVEIKR |
| L-43 | P | Humanized | 43 | DIQMTQSPSSVSASVGDRVTITC | RASQGISSWLA | WYQQKPGKAPKLLIY | VASSLQS | GVPSRFSGSGSGTDFTLTISSLQPEDIATYYC | QQADSFPRT | FGQGTKVEIKR |

TABLE 2

| | TARGET | SPECIES | SEQUENCE | FW1 | CDR1 | FW2 | CDR2 | FW3 | CDR3 | FW4 |
|---|---|---|---|---|---|---|---|---|---|---|
| H-1 | Bb | Rabbit | 44 | QSLEESGGRLVTPGTPLTLTCTVS | GFDLSTYAMS | WVRQAPGKGLEWIG | AVSATTGNTYYATWAKG | RFTMSKASTTVDLKITSPTTEDTATYFCVR | YASSGVGTYFDL | WGQGTLVTVSS |
| H-2 | P | Rabbit | 45 | QSLEESGGGLVKPGASLTLTCTAS | GFSFSSGYWIF | WVRQAPGKGLELVG | GIYSGSSGTTYYANWAKG | RFTISKTSSTTVTLQMTSLTAADTATYFCAR | SVDGIDSYDAAFNL | WGPGTLVTVSS |
| H-3 | P | Rabbit | 46 | QSLEESGGGLVKP | GFSFSSGYWIF | WVRQAPGKGLE | GIYSGSSGTTYYA | RFTISKTSSTTV | SVDGIDSYD | WGPGTL |

TABLE 2-continued

| | TARGET | SPECIES | SEQUENCE | FW1 | CDR1 | FW2 | CDR2 | FW3 | CDR3 | FW4 |
|---|---|---|---|---|---|---|---|---|---|---|
| | | | | GASLTLT CTAS | | LVG | NWAKG | TLQMT SLTAAD TATYFC AR | AAFN L | VTV SS |
| H-4 | P | Rabbit | 47 | QSLEESG GDLAKP GASLTIT CTAS | GFSFSS SYWIF | WVRQA PGKGLE LIG | GIYSSSG RMYYAS WAKG | RFTISK TSSTTM TLQMT SLTAAD TATYFC AR | SADG SDSY DAYF TL | WGP GTL VTV SS |
| H-5 | Bb | Rabbit | 48 | QSLEESG GRLVTPG GSLTLTC TVS | GFSLSN YHLG | WVRRA PGKGLE WIG | VITYGG STYYAS WVKG | RFTISK TSTTVD LKMTS LTTEDT ATYFC AR | RDSG GYHL DL | WGQ GTL VTIS S |
| H-6 | Bb | Rabbit | 49 | QSVEESG GRLVTPG GSLTLTC TVS | GFSLSS NAIN | WVRQA PGEGLD WIG | TIHTNTK TYYATW ARG | RFTISR TSSTTV DLKVTS LTAAD TATYFC GR | ADL | WGQ GTL VTV SS |
| H-7 | P | Mouse | 50 | QVTLKES GPGILQP SQTLSLT CSFS | GFSLST SGMGV G | WIRQPS GKGLE WLA | HIWWD DVKSYN PALKS | RLTISK DTSSSQ VFLRIA SVDTA DTATY YCAR | IGDGY YSFD Y | WGQ GTT LTV SS |
| H-8 | P | Humanized | 51 | QVTLKES GPTILQPT QTLTLTC TFS | GFSLST SGMGV G | WIRQPS GKALE WIA | HIWWD DVKSYN PALKS | RLTITK DTSKSQ VVLRIA SVDPV DTATY YCAR | IGDGY YSFD Y | WGQ GTT LTV SS |
| H-9 | P | Humanized | 52 | QVTLKES GPTILQPT QTLTLTC TFS | GFSLST SGMGV G | WIRQPS GKGLE WIA | HIWWD DVKSYN PALKS | RLTITK DTSKSQ VVLRIA SVDTA DTATY YCAR | IGDGY YSFD Y | WGQ GTT LTV SS |
| H-10 | P | Humanized | 53 | QVTLKES GPTLVKP TQTLTLT CTFS | GFSLST SGMGV G | WIRQPP GKALE WIA | HIWWD DVKSYN PALKS | RLTITK DTSKN QVVLRI ASVDP VDTAT YYCAR | IGDGY YSFD Y | WGQ GTT LTV SS |
| H-11 | P | Humanized | 54 | QVQLVES GGGVVQ PGRSLRL SCAAS | GFTFSC YGMH | WVRQA PGKGLE WVA | VIWYDG SNKYYA DSVKG | RFTISR DNSKN TLYLQ MNSLR AEDTA VYYC | AGGA TAMD V | WGQ GTT VTV SS |
| H-12 | P | Humanized | 55 | QEQSGG GVVQPG RSLRLSC AAS | GFTFSN YGIH | WVRQA PGKGLE WVA | VIWYDG NNKYYA DSVKG | RFTISR DNSKN TLYLQ MNSLR AEDTA VYYCA R | GGYY DSRG YYTP YYYY GMDV | WGQ GTT VTV SS |
| H-13 | P | Humanized | 56 | QVQLQES GPGLVKP SETLSLT CTVS | GGSISIY YWS | WIRQPP GKGLE WIG | YIYYSGS TNYNPS LKS | RVTISV DTSKN QFSLKL SSVTAA DTAVY YCAV | WNYG DAFDI | WGQ GTM VTV SS |
| H-14 | P | Humanized | 57 | EVQLVQS GAEVKK | GYIFTN YPIH | WVRQA PGKGLE | FIDPGGG YDEPDE | RFTISR DNAKN | RGGG YYLD | WGQ G |

TABLE 2-continued

| TARGET | SPECIES | SEQUENCE | FW1 | CDR1 | FW2 | CDR2 | FW3 | CDR3 | FW4 |
|---|---|---|---|---|---|---|---|---|---|
| | | | PGATVKI SCKVS | | WVS | RFRD | SLYLQ MNSLR AEDTA VYYCA R | Y | |
| H-15 P | Humanized | 58 | EVQLVQS GAEVKK PGATVKI SCKVS | GYIFTN YPIH | WVRQA PGKGLE WVS | FIDPGGG YDEPDE RFRD | RFTISR DNAKN SLYLQ MNSLR AEDTA VYYCA R | RGGG YYLD Y | WGQ G |
| H-16 P | Humanized | 59 | EVQLVQS GAEVKK PGATVKI SCKVS | GYIFTN YPIH | WVRQA PGKGLE WVS | FIDPGGG YDEPDE RFRD | RFTISR DNAKN SLYLQ MNSLR AEDTA VYYCA R | RGGG YYLD Y | WGQ G |
| H-17 P | Humanized | 60 | EVQLVQS GAEVKK PGESLRIS CKGS | GYIFTN YPIH | WIRQPP GKGLE WIG | FIDPGGG YDEPDE RFRD | RFVFSL DTSVST AYLQIC SLKAED TAVYY CAR | RGGG YYLD Y | WGQ G |
| H-18 P | Humanized | 61 | EVQLVQS GAEVKK PGESLRIS CKGS | GYIFTN YPIH | WIRQPP GKGLE WIG | FIDPGGG YDEPDE RFRD | RFVFSL DTSVST AYLQIC SLKAED TAVYY CAR | RGGG YYLD Y | WGQ G |
| H-19 P | Humanized | 62 | EVQLVQS GAEVKK PGESLRIS CKGS | GYIFTN YPIH | WIRQPP GKGLE WIG | FIDPGGG YDEPDE RFRD | RFVFSL DTSVST AYLQIC SLKAED TAVYY CAR | RGGG YYLD Y | WGQ G |
| H-20 P | Humanized | 63 | EVQLVQS GAEVKK PGESLRIS CKGS | GYIFTN YPIH | WIRQPP GKGLE WIG | FIDPGGG YDEPDE RFRD | RFVFSL DTSVST AYLQIC SLKAED TAVYY CAR | RGGG YYLD Y | WGQ G |
| H-21 P | Humanized | 64 | EVQLVQS GAEVKK PGESLRIS CKGS | GYIFTN YPIH | WIRQSP SRGLE WLG | FIDPGGG YDEPDE RFRD | RVTISA DKSIST AYLQW SSLKAS DTAMY YCAR | RGGG YYLD Y | WGQ G |
| H-22 P | Humanized | 65 | EVQLVQS GAEVKK PGESLRIS CKGS | GYIFTN YPIH | WVRQA PGKGLE WVS | FIDPGGG YDEPDE RFRD | RLTISK DTSKN QVVLT MTNMD PVDTAT YYCAR | RGGG YYLD Y | WGQ G |
| H-23 P | Humanized | 66 | EVQLVQS GAEVKK PGESLRIS CKGS | GYIFTN YPIH | WVRQA PGKGLE WVS | FIDPGGG YDEPDE RFRD | RVTISV DTSKN QFSLKL SSVTAA DTAVY YCAR | RGGG YYLD Y | WGQ G |
| H-24 P | Humanized | 67 | EVQLVQS GAEVKK PGESLRIS CKGS | GYIFTN YPIH | WVRQA PGQGLE WMG | FIDPGGG YDEPDE RFRD | RFVFSL DTSVST AYLQIC SLKAED TAVYY CAR | RGGG YYLD Y | WGQ G |

TABLE 2-continued

| TARGET | SPECIES | SEQUENCE | FW1 | CDR1 | FW2 | CDR2 | FW3 | CDR3 | FW4 |
|---|---|---|---|---|---|---|---|---|---|
| H-25 P | Humanized | 68 | EVQLVQS GAEVKK PGESLRIS CKGS | GYIFTN YPIH | WVRQA TGQGL EWMG | FIDPGGG YDEPDE RFRD | RFTISR DDSKN TAYLQ MNSLK TEDTA VYYCT R | RGGG YYLD Y | WGQ G |
| H-26 P | Mouse | 69 | QVLLQQS APELARP GASVKM SCTAS | GYIFTN YPIH | WVKQR PGQGLE WIG | FIDPGGG YDEPDE RFRD | RATLTA DKSSST AYMQL SSLTSE DSAIYY CAR | RGGG YYLD Y | WGQ GTT LTV SS |
| H-27 P | Humanized | 70 | QVQLQES GPGLVKP SQTLSLT CTVS | GYIFTN YPIH | WVRQA PGKGLE WVS | FIDPGGG YDEPDE RFRD | RVTISV DTSKN QFSLKL SSVTAA DTAVY YCAR | RGGG YYLD Y | WGQ G |
| H-28 P | Humanized | 71 | QVQLQES GPGLVKP SQTLSLT CTVS | GYIFTN YPIH | WVRQA PGKGLE WVS | FIDPGGG YDEPDE RFRD | RVTISV DTSKN QFSLKL SSVTAA DTAVY YCAR | RGGG YYLD Y | WGQ G |
| H-29 P | Humanized | 72 | QVQLQES GPGLVKP SQTLSLT CTVS | GYIFTN YPIH | WVRQA PGKGLE WVS | FIDPGGG YDEPDE RFRD | RVTISV DTSKN QFSLKL SSVTAA DTAVY YCAR | RGGG YYLD Y | WGQ G |
| H-30 P | Humanized | 73 | QVQLQES GPGLVKP SQTLSLT CTVS | GYIFTN YPIH | WVRQA TGQGL EWMG | FIDPGGG YDEPDE RFRD | RVTITA DKSTST AYMEL SSLRSE DTAVY YCAR | RGGG YYLD Y | WGQ G |
| H-31 P | Humanized | 74 | QVQLVQ SAPEVAK PGTSVK MSCKAS | GYIFTN YPIH | WVKQA PGQGLE WIG | FIDPGGG YDEPDE RFRD | RATLTA DKSTST AYMEL SSLRSE DTAIYY CAR | RGGG YYLD Y | WGQ GTL VTV SS |
| H-32 P | Humanized | 75 | QVQLVQ SGPEVAK PGSSVKV SCKAS | GYIFTN YPIH | WVRQA PGQGLE WIG | FIDPGGG YDEPDE RFRD | RATITA DKSTST AYMEL SSLRSE DTAVY YCAR | RGGG YYLD Y | WGQ GTL VTV SS |
| H-33 P | Mouse | 76 | LNMERH WIFLFLL SVTAGV HSQVLLQ QSAPELA RPGASVK MSCTAS | GYIFTN YPIH | WVKQR PGQGLE WIGFID PGGGY DEPDER FRDRAT LTADKS SSTAY MQLSSL TSEDSA IYYCAR RGGGY YLDYW GQDTT LTVSAA STTPPS VKGEF | FIDPGGG YDEPDE RFRD | RATLTA DKSSST AYMQL SSLTSE DSAIYY CARRG GGYYL DYWGQ DTTLTV SAASTT PPSVKG EF | | |

TABLE 2-continued

| TARGET | SPECIES | SEQUENCE | FW1 | CDR1 | FW2 | CDR2 | FW3 | CDR3 | FW4 |
|---|---|---|---|---|---|---|---|---|---|
| H-34 P | Mouse | 77 | EVQLQQS VPELARP GASVKM SCTAS | GYIFTT YPIH | WVKQR PGQGLE WIG | FIDPGGG YDEPDD KFRD | RATLTADKSSTTAYMQL SSLTSEDSAVYYCAR | | |
| H-35 Bb | Mouse | 78 | QVQLQQ SGAELAK PGASVR MSCKAS | GYTFTN YWIH | WVKQR PGQGLE WIG | YINPNT GYNDYN QKFKD | KATLT ADKSSS TVYMQ LSSLTS EDSAV YYCAR | GGQL GLRR AMDY | WGQ GTS VTV SS |
| H-36 Bb | Humanized | 79 | QVQLVQ SGAEVK KPGASVK MSCKAS | GYTFTN YWIH | WVRQA PGQGLE WIG | YINPNT GYNDYN QKFKD | RATLTA DKSSST VYMQL SSLRSE DTAVY YCAR | GGQL GLRR AMDY | WGQ GTL VTV SS |
| H-37 Bb | Humanized | 80 | QVQLVQ SGAEVA KPGASVK MSCKAS | GYTFTN YWIH | WVKQR PGQGLE WIG | YINPNT GYNDYN QKFKD | KATLT ADKSSS TVYMQ LSSLTS EDTAV YYCAR | GGQL GLRR AMDY | WGQ GTL VTV SS |
| H-38 C3b | Mouse | 81 | QVQLQQ SGAEIVK PGASVK MSCKAS | GYTFTS YWIN | WVKQR PGQGLE WIG | DIYPVR GITNYSE KFKN | KAKMIP DTSSST VYMQL SSLTSE DSAVY YCSR | GNFG NFDA MDY | WGQ GTS VTV SS |
| H-39 C3b | Humanized | 82 | QVQLVQ SGAEIVK PGASVK MSCKAS | GYTFTS YWIN | WVKQA PGQGLE WIG | DIYPVR GITNYSE KFKN | KATMIP DTSTST VYMEL SSLRSE DTAVY YCSR | GNFG NFDA MDY | WGQ GTM VTV SS |
| H-40 C3b | Humanized | 83 | QVQLVQ SGAEIVK PGASVK MSCKAS | GYTFTS YWIN | WVKQR PGQGLE WIG | DIYPVR GITNYSE KFKN | KAKMIP DTSTST VYMQL SSLTSE DTAVY YCSR | GNFG NFDA MDY | WGQ GTM VTV SS |
| H-41 C3b | Humanized | 84 | QVQLVQ SGAEVK KPGASVK MSCKAS | GYTFTS YWIN | WVRQA PGQGLE WIG | DIYPVR GITNYSE KFKN | KATMIP DTSTST VYMEL SSLRSE SS | GNFG NFDA MDY | WGQ GTM VTV |
| H-42 P | Humanized | 85 | QVQLVQ SGAEVK KPGASVK VSVKVS | GYTLTE LSMH | WVRQA PGKGLE WMG | GFDPED GETIYA QMFQG | RVTMT EDTSTD TAYMD LSSLRS EDTAV YYCAT | GTYY DILTG PSYY YYGL GV | WGQ GTT VTV SS |
| H-43 P | Humanized | 86 | QVQLEQS GPGLVKP SQTLSLT CTVS | GDSISS GGHYW S | WIRQHP GKGLE WIG | YIYYSGS SYYNPS LKS | RFTISV DTSKN QFSLKL TSVTAA DTAVY YCAR | TGDY FDY | WGL GTL VTV SS |

TABLE 3

| Target | HEAVY | SEQUENCE | LIGHT | SEQUENCE |
|---|---|---|---|---|
| P | EVQLVQSGAEVKKPGESLRISCK GSGYIFTNYPIHWIRQSPSRGLEW LGFIDPGGGYDEPDERFRDRVTIS | 87 | DIQMTQSPSSLSASVGDRV TITCRASQDISFFLNWYQQ KPGKAPKLLIYYTSRYHSG | 88 |

TABLE 3-continued

| Target | HEAVY SEQUENCE | | LIGHT SEQUENCE | |
|---|---|---|---|---|
| | ADKSISTAYLQWSSLKASDTAMY YCARRGGYYLDYWGQGTLVTV SSASTKGPSVFPLAPSSKSTSGGT AALGCLVKDYFPEPVTVSWNSGA LTSGVHTFPAVLQSSGLYSLSSVV TVPSSSLGTQTYICNVNHKPSNTK VDKKVEPKSCDKTHTCPPCPAPE LLGGPSVFLFPPKPKDTLMISRTPE VTCVVVDVSHEDPEVKFNWYVD GVEVHNAKTKPREEQYASTYRV VSVLTVLHQDWLNGKEYKCKVS NKALPAPIEKTISKAKGQPREPQV YTLPPSRDELTKNQVSLTCLVKGF YPSDIAVEWESNGQPENNYKTTP PVLDSDGSFFLYSKLTVDKSRWQ QGNVFSCSVMHEALHNHYTQKS LSLSPGK | | VPSRFSGSGSGTEFTLTISS LQSEDFAVYYCQHGNTLP WTFGQGTKVEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | |
| P | QVQLQESGPGLVKPSQTLSLTCTV SGYIFTNYPIHWVRQATGQGLEW MGFIDPGGGYDEPDERFRDRVTIT ADKSTSTAYMELSSLRSEDTAVY YCARRGGYYLDYWGQGTLVTV SSASTKGPSVFPLAPSSKSTSGGT AALGCLVKDYFPEPVTVSWNSGA LTSGVHTFPAVLQSSGLYSLSSVV TVPSSSLGTQTYICNVNHKPSNTK VDKKVEPKSCDKTHTCPPCPAPE LLGGPSVFLFPPKPKDTLMISRTPE VTCVVVDVSHEDPEVKFNWYVD GVEVHNAKTKPREEQYASTYRV VSVLTVLHQDWLNGKEYKCKVS NKALPAPIEKTISKAKGQPREPQV YTLPPSRDELTKNQVSLTCLVKGF YPSDIAVEWESNGQPENNYKTTP PVLDSDGSFFLYSKLTVDKSRWQ QGNVFSCSVMHEALHNHYTQKS LSLSPGK | 89 | DIQMTQSPSSLSASVGDRV TITCRASQDISFFLNWYQQ KPGKAPKLLIYYTSRYHSG IPPRFSGSGYGTEFTFTISSL EAEDAATYYCQHGNTLP WTFGQGTKVEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | 90 |
| P | QVQLVQSAPEVAKPGTSVKMSCK ASGYIFTNYPIHWVKQAPGQGLE WIGFIDPGGGYDEPDERFRDRATL TADKSTSTAYMELSSLRSEDTAIY YCARRGGYYLDYWGQGTLVTV SSASTKGPSVFPLAPSSKSTSGGT AALGCLVKDYFPEPVTVSWNSGA LTSGVHTFPAVLQSSGLYSLSSVV TVPSSSLGTQTYICNVNHKPSNTK VDKRVEPKSCDKTHTCPPCPAPEL LGGPSVFLFPPKPKDTLMISRTPE VTCVVVDVSHEDPEVKFNWYVD GVEVHNAKTKPREEQYASTYRV VSVLTVLHQDWLNGKEYKCKVS NKALPAPIEKTISKAKGQPREPQV YTLPPSRDELTKNQVSLTCLVKGF YPSDIAVEWESNGQPENNYKTTP PVLDSDGSFFLYSKLTVDKSRWQ QGNVFSCSVMHEALHNHYTQKS LSLSPGK | 91 | DIQMTQSPSSLSASLGDRV TITCRASQDISFFLNWYQQ KPDGTVKLLIYYTSRYHSG VPSRFSGSGSGTDFTLTISS LQPEDFATYFCQHGNTLP WTFGQGTKLEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | 92 |
| P | QVQLVQSGPEVAKPGSSVKVSCK ASGYIFTNYPIHWVRQAPGQGLE WIGFIDPGGGYDEPDERFRDRATI TADKSTSTAYMELSSLRSEDTAV YYCARRGGYYLDYWGQGTLVT VSSASTKGPSVFPLAPSSKSTSGG TAALGCLVKDYFPEPVTVSWNSG ALTSGVHTFPAVLQSSGLYSLSSV VTVPSSSLGTQTYICNVNHKPSNT KVDKKVEPKSCDKTHTCPPCPAP ELLGGPSVFLFPPKPKDTLMISRTP EVTCVVVDVSHEDPEVKFNWYV DGVEVHNAKTKPREEQYASTYR VVSVLTVLHQDWLNGKEYKCKV SNKALPAPIEKTISKAKGQPREPQ VYTLPPSRDELTKNQVSLTCLVK GFYPSDIAVEWESNGQPENNYKT TPPVLDSDGSFFLYSKLTVDKSR | 93 | DIQMTQSPSSLSASLGDRV TITCRASQDISFFLNWYQQ KPDGTVKLLIYYTSRYHSG VPSRFSGSGSGTDFTLTISS LQPEDFATYFCQHGNTLP WTFGQGTKLEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | 94 |

TABLE 3-continued

| Target | HEAVY SEQUENCE | | LIGHT SEQUENCE | |
|---|---|---|---|---|
| | WQQGNVFSCSVMHEALHNHYTQKSLSLSPGK | | | |
| P | EVQLVQSGAEVKKPGASVKMSCKASGYIFTNYPIHWVRQAPGQGLEWIGFIDPGGYDEPDERFRDRATLTADKSSSTAYMQLSSLTSEDSAIYYCARRGGGYYLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 95 | DIQMTQSPSSLSASLGDRVTITCRASQDISFFLNWYQQKPGKAPKLLIYYTSRYHSGVPSRFSGSGSGTDFTLTISSLQPEDFATYFCQHGNTLPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 96 |
| P | QVQLVQSGAEVKKPGSSVKVSCKASGYIFTNYPIHWVRQAPGKGLEWIGFIDPGGYDEPDERFRDRVTITADESTSTAYMELSSLRSEDTAVYYCARRGGGYYLDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 97 | DIQMTQSTSSLSASLGDRVTITCRASQDISFFLNWYQQKPGKAPKLLIYYTSRYHSGVPSRFSGSGSGTDFTLTISNLQPEDFATYFCQHGNTLPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 98 |
| P | QVTLKESGPTILQPTQTLTLTCTFSGFSLSTSGMGVGWIRQPSGKALEWIAHIWWDDVKSYNPALKSRLTITKDTSKSQVVLRIASVDPVDTATYYCARIGDGYYSFDYWGQGTTLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 99 | DIQMTQSHKFMSTSVGDRVTITCKASQDVSDAVAWFQQKPGKSPKLLIYSPSYRYTGVPSRFTGSGSGTDFTFTISSVQAEDLAVYYCQQHYSTPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 100 |
| P | QVTLKESGPTLVKPTQTLTLTCTFSGFSLSTSGMGVGWIRQPPGKALEWIAHIWWDDVKSYNPALKSRLTITKDTSKNQVVLRIASVDPVDTATYYCARIGDGYYSFDYWGQGTTLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYV | 101 | DIQMTQSPSSLSTSVGDRVTITCKASQDVSDAVAWFQQKPGKAPKLLIYSPSYRTGVPSRFTGSGSGTDFTFTISSVQAEDLAVYYCQQHYSTPWTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 102 |

TABLE 3-continued

| Target | HEAVY SEQUENCE | | LIGHT SEQUENCE | |
|---|---|---|---|---|
| | DGVEVHNAKTKPREEQYASTYR VVSVLTVLHQDWLNGKEYKCKV SNKALPAPIEKTISKAKGQPREPQ VYTLPPSRDELTKNQVSLTCLVK GFYPSDIAVEWESNGQPENNYKT TPPVLDSDGSFFLYSKLTVDKSR WQQGNVFSCSVMHEALHNHYTQ KSLSLSPGK | | | |
| P | QSLEESGGGLVKPGASLTLTCTAS GFSFSSGYWIFWVRQAPGKGLEL VGGIYSGSSGTTYYANWAKGRFT ISKTSSTTVTLQMTSLTAADTATY FCARSVDGIDSYDAAFNLWGPGT LVTVSSASTKGPSVFPLAPSSKSTS GGTAALGCLVKDYFPEPVTVSWN SGALTSGVHTFPAVLQSSGLYSLS SVVTVPSSSLGTQTYICNVNHKPS NTKVDKKVEPKSCDKTH | 103 | AYDLTQTPASVEAAVGGT VTINCQASDNIYSLLAWY QQKPGQPPKLLIYRASTLA SGVPSRFKGSGSGTQFTLTI SGVECADAATYYCQQHY DYNYLDVAFGGGTEVVV KGTVAAPSVFIFPPSDEQL KSGTASVVCLLNNFYPRE AKVQWKVDNALQSGNSQ ESVTEQDSKDSTYSLSSTL TLSKADYEKHKVYACEVT HQGLSSPVTKSFNRGEC | 104 |
| P | QVQLVQSAPEVAKPGTSVKMSCK ASGYIFTNYPIHWVKQAPGQGLE WIGFIDPGGGYDEPDERFRDRATL TADKSTSTAYMELSSLRSEDTAIY YCARRGGGYYLDYWGQGTLVTV SSASTKGPSVFPLAPSSKSTSGGT AALGCLVKDYFPEPVTVSWNSGA LTSGVHTFPAVLQSSGLYSLSSVV TVPSSSLGTQTYICNVNHKPSNTK VDKKVEPKSCDKTHTCPPCPAPE LLGGPSVFLFPPKPKDTLMISRTPE VTCVVVDVSHEDPEVKFNWYVD GVEVHNAKTKPREEQYNSTYRV VSVLTVLHQDWLNGKEYKCKVS NKALPAPIEKTISKAKGQPREPQV YTLPPSRDELTKNQVSLTCLVKGF YPSDIAVEWESNGQPENNYKTTP PVLDSDGSFFLYSKLTVDKSRWQ QGNVFSCSVMHEALHNHYTQKS LSLSPGK | 105 | DIQMTQSPSSLSASLGDRV TITCRASQDISFFLNWYQQ KPDGTVKLLIYYTSRYHSG VPSRFSGSGSGTDFTLTISS LQPEDFATYFCQHGNTLP WTFGQGTKLEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | 106 |
| P | QVQLVQSAPEVAKPGTSVKMSCK ASGYIFTNYPIHWVKQAPGQGLE WIGFIDPGGGYDEPDERFRDRATL TADKSTSTAYMELSSLRSEDTAIY YCARRGGGYYLDYWGQGTLVTV SSASTKGPSVFPLAPSSKSTSGGT AALGCLVKDYFPEPVTVSWNSGA LTSGVHTFPAVLQSSGLYSLSSVV TVPSSSLGTQTYICNVNHKPSNTK VDKKVEPKSCDKTH | 107 | DIQMTQSPSSLSASLGDRV TITCRASQDISFFLNWYQQ KPDGTVKLLIYYTSRYHSG VPSRFSGSGSGTDFTLTISS LQPEDFATYFCQHGNTLP WTFGQGTKLEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | 108 |
| P | QVQLVQSAPEVAKPGTSVKMSCK ASGYIFTNYPIHWVKQAPGQGLE WIGFIDPGGGYDEPDERFRDRATL TADKSTSTAYMELSSLRSEDTAIY YCARRGGGYYLDYWGQGTLVTV SSASTKGPSVFPLAPSSKSTSGGT AALGCLVKDYFPEPVTVSWNSGA LTSGVHTFPAVLQSSGLYSLSSVV TVPSSSLGTQTYICNVNHKPSNTK VGGGGSGGGGSGGGGSPSCPAPE FLGGPSVFLFPPKPKDTLMISRTPE VTCVVVDVSQEDPEVQFNWYVD GVEVHNAKTKPREEQFNSTYRVV SVLTVLHQDWLNGKEYKCKVSN KGLPSSIEKTISKAKGQPREPQVY TLPPSQEEMTKNQVSLTCLVKGF YPSDIAVEWESNGQPENNYKTTP PVLDSDGSFFLYSRLTVDKSRWQ EGNVFSCSVMHEALHNHYTQKSL SLSLGK | 109 | DIQMTQSPSSLSASLGDRV TITCRASQDISFFLNWYQQ KPDGTVKLLIYYTSRYHSG VPSRFSGSGSGTDFTLTISS LQPEDFATYFCQHGNTLP WTFGQGTKLEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGECGGGGSGGGG SGGGGSPSCPAPEFLGGPS VFLFPPKPKDTLMISRTPE VTCVVVDVSQEDPEVQFN WYVDGVEVHNAKTKPRE EQFNSTYRVVSVLTVLHQ DWLNGKEYKCKVSNKGL PSSIEKTISKAKGQPREPQV YTLPPSQEEMTKNQVSLTC LVKGFYPSDIAVEWESNG QPENNYKTTPPVLDSDGSF | 110 |

| Target | HEAVY SEQUENCE | | LIGHT SEQUENCE | |
|---|---|---|---|---|
| | | | FLYSRLTVDKSRWQEGNV FSCSVMHEALHNHYTQKS LSLSLGK | |
| P | EVQLVQSGAEVKKPGASVKMSC KASGYIFTNYPIHWVRQAPGQGL EWIGFIDPGGGYDEPDERFRDRAT LTADKSSSTAYMQLSSLTSEDSAI YYCARRGGGYYLDYWGQGTLVT VSSASTKGPSVFPLAPSSKSTSGG TAALGCLVKDYFPEPVTVSWNSG ALTSGVHTFPAVLQSSGLYSLSSV VTVPSSSLGTQTYICNVNHKPSNT KVGGGGSGGGGSGGGGSPPCPAP ELLGGPSVFLFPPKPKDTLMISRTP EVTCVVVDVSHEDPEVKFNWYV DGVEVHNAKTKPREEQYASTYR VVSVLTVLHQDWLNGKEYKCKV SNKALPAPIEKTISKAKGQPREPQ VYTLPPSRDELTKNQVSLTCLVK GFYPSDIAVEWESNGQPENNYKT TPPVLDSDGSFFLYSKLTVDKSR WQQGNVFSCSVMHEALHNHYTQ KSLSLSPGK | 111 | DIQMTQSPSSLSASLGDRV TITCRASQDISFFLNWYQQ KPGKAPKLLIYYTSRYHSG VPSRFSGSGSGTDFTLTISS LQPEDFATYFCQHGNTLP WTFGGGTKVEIKRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGECGGGGSGGGG SGGGGSPPCPAPELLGGPS VFLFPPKPKDTLMISRTPE VTCVVVDVSHEDPEVKFN WYVDGVEVHNAKTKPRE EQYASTYRVVSVLTVLHQ DWLNGKEYKCKVSNKAL PAPIEKTISKAKGQPREPQ VYTLPPSRDELTKNQVSLT CLVKGFYPSDIAVEWESN GQPENNYKTTPPVLDSDG SFFLYSKLTVDKSRWQG NVFSCSVMHEALHNHYTQ KSLSLSPGK | 112 |
| P | QVTLKESGPTLVKPTQTLTLTCTF SGFSLSTSGMGVGWIRQPPGKAL EWIAHIWWDDVKSYNPALKSRLT ITKDTSKNQVVLRIASVDPVDTAT YYCARIGDGYYSFDYWGQGTTLT VSSASTKGPSVFPLAPSSKSTSGG TAALGCLVKDYFPEPVTVSWNSG ALTSGVHTFPAVLQSSGLYSLSSV VTVPSSSLGTQTYICNVNHKPSNT KVGGGGSGGGGSGGGGSPPCPAP ELLGGPSVFLFPPKPKDTLMISRTP EVTCVVVDVSHEDPEVKFNWYV DGVEVHNAKTKPREEQYASTYR VVSVLTVLHQDWLNGKEYKCKV SNKALPAPIEKTISKAKGQPREPQ VYTLPPSRDELTKNQVSLTCLVK GFYPSDIAVEWESNGQPENNYKT TPPVLDSDGSFFLYSKLTVDKSR WQQGNVFSCSVMHEALHNHYTQ KSLSLSPGK | 113 | DIQMTQSPSSLSTSVGDRV TITCKASQDVSDAVAWFQ QKPGKAPKLLIYSPSYRYT GVPSRFTGSGSGTDFTFTIS SVQAEDLAVYYCQQHYST PWTFGQGTKLEIKRTVAA PSVFIFPPSDEQLKSGTASV VCLLNNFYPREAKVQWK VDNALQSGNSQESVTEQD SKDSTYSLSSTLTLSKADY EKHKVYACEVTHQGLSSP VTKSFNRGECGGGGSGGG GSGGGGSPPCPAPELLGGP SVFLFPPKPKDTLMISRTPE VTCVVVDVSHEDPEVKFN WYVDGVEVHNAKTKPRE EQYASTYRVVSVLTVLHQ DWLNGKEYKCKVSNKAL PAPIEKTISKAKGQPREPQ VYTLPPSRDELTKNQVSLT CLVKGFYPSDIAVEWESN GQPENNYKTTPPVLDSDG SFFLYSKLTVDKSRWQQG NVFSCSVMHEALHNHYTQ KSLSLSPGK | 114 |
| C3B | qvqlqqsgaeivkpgasvkmsckasgytftsywi nwvkqrpgqglewigdiypvrgitnysekfknka kmipdtssstvymqlssltsedsavyycsrgnfgn fdamdywgqgtsvtvssASTKGPSVFPL APSSKSTSGGTAALGCLVKDYFPE PVTVSWNSGALTSGVHTFPAVLQ SSGLYSLSSVVTVPSSSLGTQTYIC NVNHKPSNTKVDKKVEPKSCDKT HTCPPCPAPELLGGPSVFLFPPKPK DTLMISRTPEVTCVVVDVSHEDPE VKFNWYVDGVEVHNAKTKPREE QYASTYRVVSVLTVLHQDWLNG KEYKCKVSNKALPAPIEKTISKAK GQPREPQVYTLPPSRDELTKNQVS LTCLVKGFYPSDIAVEWESNGQP ENNYKTTPPVLDSDGSFFLYSKLT VDKSRWQQGNVFSCSVMHEALH NHYTQKSLSLSPGK | 115 | qivltqspailsaspgekvtmtcsatssit yihwyqqksgtspkrwiydtsrlasgv ptrfsgsgsgtsysltistmeaedaatyyc qqwssnpptfgggtkleikRTVAAP SVFIFPPSDEQLKSGTASVV CLLNNFYPREAKVQWKV DNALQSGNSQESVTEQDS KDSTYSLSSTLTLSKADYE KHKVYACEVTHQGLSSPV TKSFNRGEC | 116 |
| C3b | QVQLvQSGAEVKKPGASVKMSC KASGYTFTSYWINWVRQAPGQG LEWIGDIYPVRGITNYSEKFKNKA | | EIVLTQSPATLSASPGEKV TMTCSATSSITYIHWYQQK pGQAPKRWIYDTSRLASG | 117 / 118 |

TABLE 3-continued

| Target | HEAVY SEQUENCE | | LIGHT SEQUENCE | |
|---|---|---|---|---|
| | TMIPDTSTSTVYMELSSLRSEDTA<br>VYYCSRGNFGNFDAMDYWGQGT<br>mVTVSSASTKGPSVFPLAPSSKST<br>SGGTAALGCLVKDYFPEPVTVSW<br>NSGALTSGVHTFPAVLQSSGLYSL<br>SSVVTVPSSSLGTQTYICNVNHKP<br>SNTKVDKKVEPKSCDKTHTCPPC<br>PAPELLGGPSVFLFPPKPKDTLMIS<br>RTPEVTCVVVDVSHEDPEVKFNW<br>YVDGVEVHNAKTKPREEQYAST<br>YRVVSVLTVLHQDWLNGKEYKC<br>KVSNKALPAPIEKTISKAKGQPRE<br>PQVYTLPPSRDELTKNQVSLTCLV<br>KGFYPSDIAVEWESNGQPENNYK<br>TTPPVLDSDGSFFLYSKLTVDKSR<br>WQQGNVFSCSVMHEALHNHYTQ<br>KSLSLSPGK | | VPARFSGSGSGTSYSLTIST<br>MEpEDFATYYCQQWSSNP<br>PTFGGGTKLEIKRTVAAPS<br>VFIFPPSDEQLKSGTASVV<br>CLLNNFYPREAKVQWKV<br>DNALQSGNSQESVTEQDS<br>KDSTYSLSSTLTLSKADYE<br>KHKVYACEVTHQGLSSPV<br>TKSFNRGEC | |
| C3b | QVQLVQSGAEVAKPGASVKMSC<br>KASGYTFTNYWIHWVKQRPGQG<br>LEWIGYINPNTGYNDYNQKFKDK<br>ATLTADKSSSTVYMQLSSLTSEDT<br>AVYYCARGGQLGLRRAMDYWG<br>QGTLVTVSSASTKGPSVFPLAPSS<br>KSTSGGTAALGCLVKDYFPEPVT<br>VSWNSGALTSGVHTFPAVLQSSG<br>LYSLSSVVTVPSSSLGTQTYICNV<br>NHKPSNTKVDKKVEPKSCDKTHT<br>CPPCPAPELLGGPSVFLFPPKPKDT<br>LMISRTPEVTCVVVDVSHEDPEV<br>KFNWYVDGVEVHNAKTKPREEQ<br>YASTYRVVSVLTVLHQDWLNGK<br>EYKCKVSNKALPAPIEKTISKAKG<br>QPREPQVYTLPPSRDELTKNQVSL<br>TCLVKGFYPSDIAVEWESNGQPE<br>NNYKTTPPVLDSDGSFFLYSKLTV<br>DKSRWQQGNVFSCSVMHEALHN<br>HYTQKSLSLSPGK | 119 | DVQITQSPSYLSASPGDTIT<br>ITCRASKSISKYLAWYQDK<br>PGKTNKLLIYSGSTLQSGIP<br>SRFSGSGSGTEFTLTISSLQ<br>PDDFAMYYCQQHDEYPW<br>TFGQGTKLEIKRTVAAPSV<br>FIFPPSDEQLKSGTASVVCL<br>LNNFYPREAKVQWKVDN<br>ALQSGNSQESVTEQDSKD<br>STYSLSSTLTLSKADYEKH<br>KVYACEVTHQGLSSPVTK<br>SFNRGEC | 120 |

In some embodiments, an anti-AP antibody described herein can comprise heavy and light chain variable regions comprising amino acid sequences that are substantially homologous or identical to the CDRs of the heavy chain and light chain variable regions of the amino acid sequences of the antibodies described herein, and wherein the antibodies retain the desired functional properties. For example, the invention provides an isolated monoclonal antibody, or antigen binding portion thereof, comprising the CDRs of a heavy chain variable region and a light chain variable region, wherein: (a) the heavy chain variable region comprises at least one, two, or three CDRs at least 80%, 85%, 90%, 95%, 99%, or 100% homologous or identical to the CDRs of a heavy chain variable region listed in Table 2 for a respective antibody; (b) the light chain variable region comprises at least one, two, or three CDRs that is at least 80%, 85%, 90%, 95%, 99%, or 100% homologous or identical to the amino acid sequence of a light chain variable region listed in Table 1 for the respective antibody; and (c) the antibody specifically binds to respective protein, C3b, P, Ba, or Bb.

In various aspects, the antibody can be, for example, a human antibody, a humanized antibody or a chimeric antibody. In other aspects, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding the amino acid sequences, followed by testing of the encoded altered antibody for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an anti-AP antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for retained function (i.e., the functions set forth in (c) through (j) above) using the functional assays described herein.

An anti-AP antibody described herein can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Thus, such antibodies contain the $V_H$ and $V_L$ CDR sequences described in the Tables yet may contain different framework sequences from these antibodies.

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

In general, therapeutic antibodies, once selected, can be manipulated, altered and engineered in a variety of ways for various different reasons. For example, the inactive (non-binding) parts of an selected antibody may be changed and manipulated in countless ways which do not at all change the defining functions of the antibody. In fact, the functional (protein binging part) of the antibody might be entirely severed from the rest of the antibody. These alterations may have utility for making the antibody easier or less costly to produce. Or, such alterations may make the antibody more chemically stable in human subjects. These manipulations and derivations of the selected antibodies are not new or separate inventions. Accordingly, any such manipulations, alternations and derivations of the selected genus of antibodies which utilize the same defining characteristics of the genus itself are within the scope of the invention.

The invention includes compounds which constitute the functional (target protein binding) components of any one or several of the selected genus of antibodies, as well as the therapeutic use of such compounds. These compounds include, but are not limited to, whole antibodies of the selected genus, antigen-binding fragments of antibodies of the selected genus, and chimeric or humanized manifestations of any antibody or antibody fragment derived from the selected genus of antibodies. Such derivations of the inventions may include, but are not limited to, truncated, linear, single-chained, an IgG fragment, a F(ab) fragment, a F(ab') fragment, a F(ab)2 fragment, a F(ab')2 fragment, an Fv fragment or an scFv fragment which may be manifested from any antibody of the selected genus.

The invention includes the result of any member of the antibody genus having its Fc region mutated at the 297 position to generate an aglycosylated antibody. The invention includes the results of any antibody of the selected genus being engineered to elicit reduced Fc-mediated effector functions. Methods of engineering may include, without limitation, amino acid mutations, amino acid additions or deletions, glycan modification or removal, pegylation, and/or truncation.

In some embodiments, the anti-AP antibody or antigen binding fragment thereof that specifically binds to properdin and inhibits alternative complement pathway activation. The anti-AP antibody comprises a heavy chain having at least one, two, or three CDR(s) having at least 80%, at least 90%, or 100% sequence identity to the CDRs of the heavy chain variable domains of SEQ ID NOs: 44, 46-48, 51-78 or 86, or (ii) competitively inhibits binding of an isolated anti-properdin antibody or antigen binding fragment thereof, a heavy chain variable region having at least one, two, three CDR(s) having at least 80%, at least 90%, or 100% sequence identity to the CDRs of the heavy chain variable domains of SEQ ID NOs: 44, 46-48, 51-78 or 86, to properdin.

In some embodiments, the anti-properdin antibody or antigen binding fragment thereof that specifically binds to properdin and inhibits alternative complement pathway activation comprises a light chain having at least one, two, or three CDR(s) having at least 80%, at least 90%, or 100% sequence identity to the CDRs of the light chain variable domains of SEQ ID NOs: 2, 3, 4, 7-33, 41, 42, or 43, or (ii) competitively inhibits binding of an isolated anti-properdin antibody or antigen binding fragment thereof, a heavy chain variable region having at least one, two, three CDR(s) having at least 80%, at least 90%, or 100% sequence identity to the CDRs of the light chain variable domains of SEQ ID NOs: 2, 3, 4, 7-33, 41, 42, or 43, to properdin.

In other embodiments, the anti-properdin antibody or antigen binding fragment thereof that specifically binds to properdin and inhibits alternative complement pathway activation comprises a heavy chain including three CDRs of heavy chain variable domains selected from the group consisting of SEQ ID NOs: 44, 46-48, 51-78 and 86, or (ii) competitively inhibits binding of an isolated anti-properdin antibody or antigen binding fragment thereof, which comprises a heavy chain including three CDRs of heavy chain variable domains selected from the group consisting of SEQ ID NOs: SEQ ID NOs: 44, 46-48, 51-78 and 86, to properdin.

In other embodiments, the anti-properdin antibody or antigen binding fragment thereof that specifically binds to properdin and inhibits alternative complement pathway activation comprises a light chain including three CDRs of light chain variable domains selected from the group consisting of SEQ ID NOs: 2, 3, 4, 7-33, 41, 42, and 43, or (ii) competitively inhibits binding of an isolated anti-properdin antibody or antigen binding fragment thereof, which comprises a light chain including three CDRs of light chain variable domains selected from the group consisting of SEQ ID NOs: 2, 3, 4, 7-33, 41, 42, and 43, to properdin.

It will be appreciated that any anti-AP antibody or antigen binding fragment thereof can be used to treat ocular hemorrhage and/or fibrosis. These anti-AP antibodies can include anti-AP disclosed in, for example, patent application numbers US2012/501,165 (Bansal), PCT/US2012/675,220 (Bansal), PCT/US2013/034,982 (Bansal), PCT/2011/026, 841 (Bansal), PCT/US2013/583,879 (Bansal), US2013/646, 286 (Bansal), U.S. Ser. No. 09/138,723 (Bansal, Gliatech), PCT/US2012/044974 (Song), PCT/US2008/007270 (Song), U.S. Ser. No. 14/183,213 (Holers, et al.), U.S. Ser. No. 11/057,047 (Holers, et al.), U.S. Ser. No. 13/482,328 (Fung, et al., Genentech), U.S. Ser. No. 13/135,907 (Campagne, Genentech), PCT/US2008/065771 (Champagne, Genentech), PCT/EP2003/007487 (Tedesco), PCT/IB2012/057394 (Brannetti, Novartis), PCT/EP2009/060052 (Diefenbach-Streiber, Novartis), U.S. Ser. No. 13/716,526 (Johnson et al., Novartis), PCT/EP2010/056129 (Etemad-Gilbertson, et al., Novartis), PCT/US2006/043103 (Fung et al.), PCT/US2003/027808 (Wang, Alexion), U.S. Ser. No. 11/050,543 (Bell), and issued U.S. Pat. No. 8,435,512 (Bansal).

Treatment Methods

The methods of the present invention can generally involve the steps of: administering to a mammalian subject in need thereof an effective amount or therapeutically effective amount of an anti-AP antibody to treat retinal fibrosis, hemorrhage and/or ocular inflammation.

An "effective amount" or "therapeutically effective amount" of a subject antibody is an amount that is effective to reduce the production and/or level of a polypeptide generated following activation of the alternative complement pathway by at least about 20%, at least about 30%, at least about 40%, at least about 50%, at least about 60%, at least about 70%, at least about 80%, at least about 90%, or more.

The anti-properdin antibody can be administered to an individual in a formulation with a pharmaceutically acceptable excipient(s). A wide variety of pharmaceutically acceptable excipients as known in the art and need not be discussed in detail herein.

In the methods described herein, a subject antibody can be administered to the host using any convenient means capable of resulting in the desired therapeutic effect. Thus, the antibody can be incorporated into a variety of formulations for therapeutic administration. In one example, a subject antibody can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols.

As such, administration of a subject antibody can be achieved in various administrations, including oral, buccal, rectal, parenteral, intraperitoneal, intradermal, subcutaneous, intramuscular, transdermal, intranasal, pulmonary, intratracheal, etc administrations. For treatment of ocular diseases, currently, the preferred method of administration is via intravitreal (IVT) injection directly into the eye. This does not exclude potential administration via alternative mechanisms which are not currently available, but which may become available in the future. If required, the anti-AP antibody may also be given systemically via subcutaneous injection or intravenous injection. Administration of the anti-AP antibodies described herein, and/or any functional derivations thereof, may be by any method known in the art. Administration can be acute or chronic (e.g., daily, weekly, monthly, etc.) or in combination with other agents.

In pharmaceutical dosage forms, the anti-AP antibodies can be administered independently or in appropriate association, as well as in combination, with other pharmaceutically active compounds. The following methods and excipients are merely exemplary and are in no way limiting.

Unit dosage forms for injection or intravenous administration can comprise the anti-AP antibodies in a composition as a solution in sterile water, normal saline or another pharmaceutically acceptable carrier.

An anti-AP antibody can be administered to an individual with a certain frequency and for a period of time so as to achieve the desired therapeutic effect. For example, an anti-AP antibody can be administered, for example, once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), or substantially continuously, or continuously, over a period of time ranging from about one day to about one week, from about two weeks to about four weeks, from about one month to about two months, from about two months to about four months, from about four months to about six months, or longer.

Combination Therapy

The anti-AP antibody can, in some embodiments, be administered in an effective amount in combination therapy with a second therapeutic agent.

Disease Conditions

In some embodiments, the anti-AP antibodies described herein can be used in a prophylactic treatment for a subject undergoing an ophthalmologic procedure who has been identified as being at risk for developing a complement mediated ocular disorder post procedure. In some embodiments, the anti-AP antibodies can inhibit fibrosis, hemorrhage and inflammation associated with the ocular procedure. In still other embodiments, the anti-AP antibodies can prevent neovascularization following the ophthalmologic procedure without inhibiting tissue repair.

In another embodiment, the invention provides a process for inhibiting fibrosis and hemorrhage with normal tissue repair, in a subject undergoing an ocular surgical procedure (or other physical ocular trauma), wherein an anti-AP antibody described herein is administered in order to promote wound healing. In one embodiment of the invention, the invention provides a process for treating AP mediated ocular pathologies occurring during an ocular surgical procedure wherein the subject undergoing the procedure suffers from condition characterized by retinal hemorrhage or inflammation which may/may not lead to vision loss. This embodiment includes the step of administering a qualifying anti-P antibody either immediate before, during or after the surgical procedure.

In other embodiments, an anti-AP antibody can be used to prevent fibrosis and hemorrhage secondary to a pathology of uveitis, including but not limited to; Iritis, Pars planitis, Choroiditis, Chorioretinitis, Anterior uveitis, Posterior uveitis, Scleritis, ocular neovascularization, atherosclerosis, retinal artery occlusion secondary to antiphospholipid syndrome, neovascular glaucoma, rubeosis iridis, Purtscher's retinopathy, Sorsby's fundus dystrophy, Doyne Honeycomb Retinal Dystrophy, Malattia Leventinese, Familial Dominant Drusen, North Carolina macular dystrophy, Juvenile Macular degeneration, Stargardt's disease, Vitelliform Macular Dystrophy, Adult-Onset Foveomacular Vitelliform Dystrophy (AOFVD), Sorsby's fundus dystrophy, and Best's Disease.

In other embodiments, one or more of the claimed anti-AP antibodies can be used to prevent inflammation, neovascularization, cellular atrophy, tissue degradation, release of LDH, fibrosis and/or hemorrhage secondary to a pathology of uveitis, including but not limited to; Iritis, Pars planitis, Choroiditis, Chorioretinitis, Anterior uveitis, Posterior uveitis, or Scleritis, ocular neovascularization, diabetic retinopathy or other inflammatory disorder of the eye associated with diabetes, prevent hypertensive retinopathy, prevent autoimmune uveitis or uveitis secondary to an autoimmune disorder, Behçet's Disease, Eales Disease, or other autoimmune inflammtory disease of the eye, atherosclerosis, retinal artery occlusion secondary to antiphospholipid syndrome, neovascular glaucoma, rubeosis iridis, Purtscher's retinopathy, AMD, Sorsby's fundus dystrophy, Doyne Honeycomb Retinal Dystrophy, Malattia Leventinese, Familial Dominant Drusen, North Carolina macular dystrophy, Juvenile Macular degeneration, Stargardt's disease, Vitelliform Macular Dystrophy, Adult-Onset Foveomacular Vitelliform Dystrophy (AOFVD), Sorsby's fundus dystrophy, or Best's Disease, vascular occlusion including, but not limited to; Central retinal vein occlusion (CRVO), occlusive peripheral arterial disease, ocular ischemic syndrome secondary to atherosclerosis, retinal artery occlusion secondary to antiphospholipid syndrome, neovascular glaucoma, rubeosis iridis, or Purtscher's retinopathy, retinopathy of prematurity or familial exudative vitreoretinopathy, ocular pathology occurring in the anterior segments of the eye, and Fuchs' corneal endothelial dystrophy.

In some embodiments, an anti-AP antibody is used to prevent fibrosis and/or hemorrhage secondary to a pathology characterized by vascular occlusion. Such pathologies associated with vascular occlusion can include: Central retinal vein occlusion (CRVO), occlusive peripheral arterial disease, ocular ischemic syndrome secondary to atherosclerosis, retinal artery occlusion secondary to antiphospholipid syndrome, neovascular glaucoma, rubeosis iridis, and Purtscher's retinopathy.

In one embodiment, the anti-AP antibody is used to prevent fibrosis and hemorrhage secondary to diabetic retinopathy. In another embodiment, an anti-P, anti-C3b, or anti-Bb antibody is used to treat any or all AP mediated pathologies associated with retinal fibrosis or hemorrhage in a diabetic patient, hypertensive retinopathy, an autoimmune disorder, autoimmune uveitis or uveitis, Behçet's Disease, Eales Disease, or other autoimmune disease of the eye.

In some embodiments, the anti-AP antibody is used to prevent fibrosis and/or hemorrhage secondary to retinopathy of prematurity or familial exudative vitreoretinopathy, ocular pathology occurring in the anterior segments of the eye, Fuchs' corneal endothelial dystrophy, repeated treatment with anti-VEGF agents for prevention of neovascularization.

In some embodiments, the anti-AP antibody used to treat ocular hemorrhage and/or fibrosis is one which binds to one of the group of complement factors which includes Ba, Bb, C3b, D, C5, C6, C7 or C8. In other embodiments of the invention, the anti-AP antibody used to treat ocular hemorrhage and/or fibrosis is one which also inhibits the classical or lectin pathway.

In one example, an elderly patient being treated with an anti-VEGF agent for prevention of CNV, arrives at a hospital for ocular surgery. The patient can be required to discontinue the anti-VEGF treatment prior to undergoing the surgical procedure because anti-VEGF agents jeopardize post-surgical healing and recovery. The surgery causes inflammation and hemorrhage immediately, due to trauma caused by the surgery. Without the anti-VEGF treatment, the uncontrolled inflammation results in the patient developing postoperative CNV. To prevent CNV in the absence of an anti-VEGF agent, the surgeon could administer to the patient an anti-P antibody of this invention. This anti-P agent inhibits progression of inflammation, and thereby inhibits formation of VEGF responsible for neovascularization. Post-operative wound healing occurs without development of neovascularization, fibrosis, vascular leakage or edema.

In another example, a patient arrives at a healthcare center seeking treatment for CNV or fibrovascular PED and as per instructions the ocular specialist gives the patient an injection of Ranibizumab. The patient undergoes RPE tear occurring less than a minute after intravitreal injection of Ranibizumab for a fibrovascular PED. Such cases do not use Ranibizumab as the drug is not indicated for tear. However, the drug of the present invention does not block tissue repair and therefore would be indicated for such a patient without having the fear of not healing lesions.

In yet another example, patient suffering from ocular defects in one or both eyes visits the hospital for ocular surgery for correction of pathologies associated with birth defects, lens changes, cataracts, or glaucoma. The patient may be undergoing ocular surgery for cosmetic reasons or for natural lens replacement. As a result of surgery, or due to spontaneous or congenital causes, the patient develops neovascularization. Under such conditions, Ranibizumab cannot be administered as it is contraindicated for ocular surgery. Anti-P antibodies of this invention can be used to prevent CNV and the tissue repair will proceed normally. Thus anti-P antibodies can be used in ocular conditions where neovascularization and surgery are both part of the disease process.

In still another example, a patient who received monthly or bi-monthly injections of Lucentis to prevent CNV will have continuous lesions as Lucentis prevents tissue repair. The ultimate result is formation of scar and fibrosis and loss of vision. Anti-AP antibodies of the current invention prevent the formation of new VEGF and therefore would control CNV, while also preventing hemorrhage and fibrosis that threaten vision. Administration of an anti-AP antibody of the current invention could be used to prevent vision loss in patients who have undergone repeated treatments of an anti-VEGF agent.

In yet another example, an elderly patient presents with vision loss after 2 years of monthly Ranibizumab therapy. An ophthalmic specialist attributes the patient's vision loss to lesion characteristics commonly associated with suppressed CNV, such as pigmentary abnormalities, atrophic scar, and the absence of leakage. Future VA improvements in patients receiving Ranibizumab therapy may require preservation of photoreceptor and RPE function rather than strategies that target CNV. Administration of an anti-AP antibody of the invention would inhibit production of MAC, along with other inflammatory cytokines and mediators which jeopardize RPE cell viability. Preservation of the RPE cells by the anti-AP agent would preserve vision when the anti-VEGF agent is no longer able to prevent vision loss.

In another example, a patient having been treated with an anti-VEGF agent for tumor growth suppression presents with ongoing lesions and hemorrhaging due to lack of healing at the site of tumor regression. Anti-VEGF agents are well known to be effective for tumor regression. Anti-VEGF agents inhibit vascular growth to the tumor, and thereby inhibit tumor growth. However, anti-VEGF agents also inhibit post tumor recession healing and healthy tissue regrowth. An ophthalmic specialist could administer an anti-AP agent of the invention in order to preserve the tumor suppression accomplished by the anti-VEGF agent, while also providing treatment for wound healing and healthy tissue regrowth. The invention of this application could be used to promote tumor regression by inhibiting VEGF produced by the AP, without jeopardizing the VEGF needed for healthy tissue regrowth and healing.

In another example, an older patient suffering from ocular defects in one or both eyes visits the hospital for ocular surgery. Surgery of the eye causes immediate inflammation and hemorrhage as a result of trauma. Inflammatory cytokines and mediators begin to proliferate immediately during and after surgery. In the days and weeks following surgery, inflammation continues, resulting in the release of growth factors and activation of immune system cells. Post operative complications of ocular surgery include fibrosis, neovascularization, vascular leakage and edema. To improve surgical outcome, the surgeon can administer an anti-P antibody of the present invention immediately prior to surgery. Administration of the anti-P antibody prior to surgery immediately reduces inflammation and hemorrhaging during surgery and inhibits the release of growth factors and activation of immune system cells following surgery. Post-operative wound healing occurs without development of neovascularization, fibrosis, vascular leakage or edema.

In another example, an older patient suffering from non-proliferative diabetic retinopathy in one or both eyes visits the hospital for ocular surgery. Inflammatory cytokines and mediators begin to proliferate immediately during and after surgery. In the days and weeks following surgery, inflammation continues, resulting in the release of growth factors and activation of immune system cells Inflammation and the release of growth factors cause the patient's diseased blood vessels to grow abnormally, resulting in neovascularization. The onset of neovascularization advances the patients non-proliferative diabetic retinopathy into proliferative diabetic retinopathy, which jeopardizes the patient's vision. To improve surgical outcome and to prevent post-surgical advancement of the patient's disease condition, the surgeon can administer an anti-P antibody of the present invention immediately prior to surgery. Administration of the anti-P antibody prior to surgery immediately reduces inflammation and hemorrhaging during surgery and inhibits the release of growth factors and activation of immune system cells following surgery. Post-operative wound healing occurs without development of neovascularization, fibrosis, vascular leakage or edema.

In another, example an older patient suffering from proliferative diabetic retinopathy in one or both eyes visits the hospital for ocular surgery. In patients with proliferative diabetic retinopathy, there is neovascularization of the blood vessels supplying the retina. The standard treatment for proliferative diabetic retinopathy includes administration of an anti-VEGF agent. Anti-VEGF agents are counter-indicated for ocular surgery. The patient will be required to discontinue use of the anti-VEGF agent in order to undergo ocular surgery. Without the anti-VEGF agent, the inflammation caused by the ocular surgery causes release of inflammatory mediators, cytokines and growth factors which can cause neovascularization in the patient with proliferative diabetic retinopathy. To improve surgical outcome and to prevent post-surgical advancement of the patient's disease condition, the surgeon can administer an anti-P antibody of the present invention immediately prior to surgery. Administration of the anti-P antibody prior to surgery immediately reduces inflammation and hemorrhaging during surgery and inhibits the release of growth factors and activation of immune system cells following surgery. Post-operative wound healing occurs without development of neovascularization, fibrosis, vascular leakage or edema.

In yet another example, a patient who has been diagnosed with a disorder associated with occlusive retinal vasculitis, such as Bechet's or Eales' disease, visits the hospital for ocular surgery. Occlusive retinal vasculitis is an inflammatory condition in which chronic inflammation can lead to retinal neovascularization. Ocular surgery causes trauma-induced inflammation which causes the immediate release of inflammatory cytokines and mediators which begin to proliferate immediately during surgery. In the days and weeks following surgery, inflammation continues, resulting in the release of growth factors and activation of immune system cells. To improve surgical outcome and to prevent post-surgical advancement of the patient's disease condition, the surgeon can administer an anti-P antibody of the present invention immediately prior to surgery. Administration of the anti-P antibody prior to surgery immediately reduces inflammation and hemorrhaging during surgery and inhibits the release of growth factors and activation of immune system cells following surgery. Post-operative wound healing occurs without development of neovascularization, fibrosis, vascular leakage or edema.

In yet another example, an adult patient, who has previously been exposed to Histoplasma capsulatum, visits the hospital for an ocular surgery unrelated to OHS. The patient is experiencing some ocular inflammation prior to surgery, but has not yet developed "histo spots" or any other noticeable signs of ocular histoplasmosis syndrome (OHS). Ocular surgery causes trauma, inflammation and hemorrhage which make the patient more vulnerable to infection. In the weeks following surgery, the patient begins show the early signs of OHS. To improve surgical outcome, and to reduce inflammation and hemorrhage immediately following surgery, the surgeon can administer an anti-P antibody of the present invention immediately prior to surgery. Administration of the anti-P antibody does not jeopardize the patient's ability to fight infection. Post-operative wound healing occurs without development of neovascularization, fibrosis, vascular leakage or edema.

In another example, an adult patient who has been previously diagnosed with Ocular Histoplasmosis Syndrome (OHS) visits the hospital for an ocular surgery. Chronic inflammation caused by exposure to the pathogen causes some patients with OHS to develop ocular edema, neovascularization, and fibrosis. Ocular surgery causes trauma, inflammation and hemorrhage which render the patient more vulnerable to infection. To improve surgical outcome and to prevent post-surgical advancement of the patient's disease condition, the surgeon can administer an anti-P antibody of the present invention immediately prior to surgery without jeopardizing the patient's ability to fight infection. Post-operative wound healing occurs without development of neovascularization, fibrosis, vascular leakage or edema.

In yet another example, a patient who has been diagnosed with a congenital disorder associated with excessive deposition of drusen visits the hospital for ocular surgery. In patients with familial drusen, large deposits of drusen can cause ocular inflammation and a break in the blood-eye barrier, which can lead to neovascularization and vision loss. Ocular surgery causes inflammation and hemorrhage which can stress the retinal epithelial layer which is already under stress from the drusen deposits. The inflammation caused by the ocular surgery immediately causes further release of inflammatory mediators and cytokines. In the days and weeks following surgery, continued inflammation causes the release of growth factors, MAC production, and activation of immune system cells which can cause retinal cell death, breakage of the blood-retinal barrier and neovascularization. To improve surgical outcome and to prevent post-surgical advancement of the patient's disease condition, the surgeon can administer an anti-P antibody of the present invention immediately prior to surgery. Administration of the anti-P antibody prior to surgery reduces inflammation and the release of cytokines and growth factors immediately following surgery. Post-operative wound healing occurs without development of neovascularization, fibrosis, vascular leakage or edema.

In still another example, an adult patient, who has a history of developing excessive fibrotic tissue and scarring following surgical procedures, visits the hospital for ocular surgery. Ocular surgery causes immediate trauma and inflammation. In the days and weeks following surgery, inflammation causes the release of growth factors and activation of cells involved in scar formation and fibrosis. Without a prophylactic treatment for ocular fibrosis, the patient develops excessive scar tissue at the surgical site. To improve surgical outcome and to inhibit post-surgical fibrosis and scarring, the surgeon can administer an anti-P antibody of the present invention immediately prior to surgery. Administration of the anti-P antibody prior to surgery reduces inflammation and inhibits post-surgical release of growth factors and cell activations involved in fibrosis. Post-operative wound healing occurs without development of neovascularization, fibrosis, vascular leakage or edema.

In another example, an adult patient, who has a history of Von Willebrand Disease (VWD), visits the hospital for ocular surgery. Ocular surgery causes immediate trauma, inflammation and hemorrhage. Due to the patient's disorder, bleeding at the surgical site is excessive and prolonged. Without a prophylactic treatment for ocular hemolysis, the patient struggles to recover from surgery due to unresolved hemolysis. To improve surgical outcome, the surgeon can administer an anti-P antibody of the present invention immediately prior to surgery. Administration of the anti-P antibody prior to surgery reduces inflammation and hemolysis. The reduction in hemolysis improves healing at the surgical site. Post-operative wound healing occurs without development of neovascularization, fibrosis, vascular leakage or edema.

EXAMPLES

It is to be understood that this invention is not limited to the particular embodiments described herein, as such may, of course, vary. It is also to be understood that the terminology used herein is for describing particular embodiments only, and is not intended to be limiting, since the scope of the present invention will be limited only by the appended claims.

Figure 3:
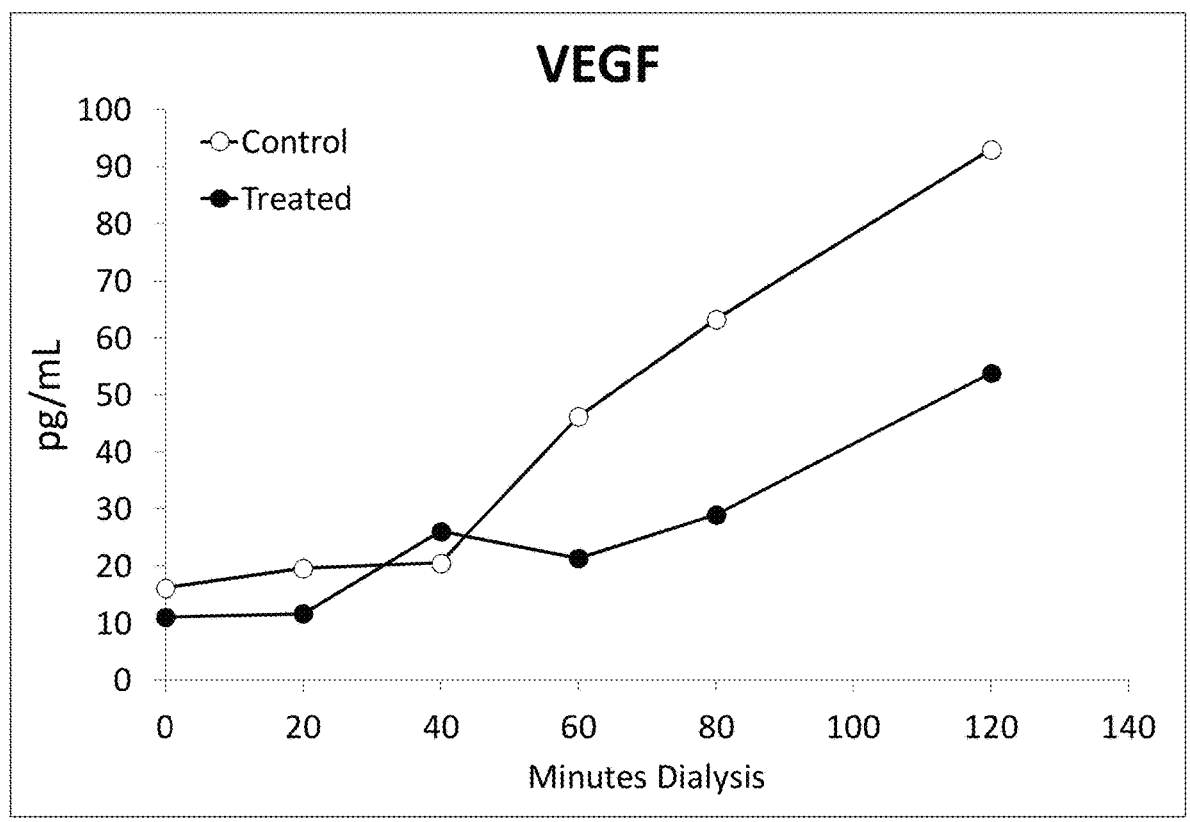
FIG. 3 presents data from an experiment in which an anti-AP antibody was added to human blood during an extracorporeal model of dialysis, wherein complement activation is known to occur. After incubation at 37° C., the levels of VEGF were measured using conventional methods. The data from this experiment demonstrate that the anti-AP antibody was able to inhibit production of VEGF in human blood.
Figure 4:
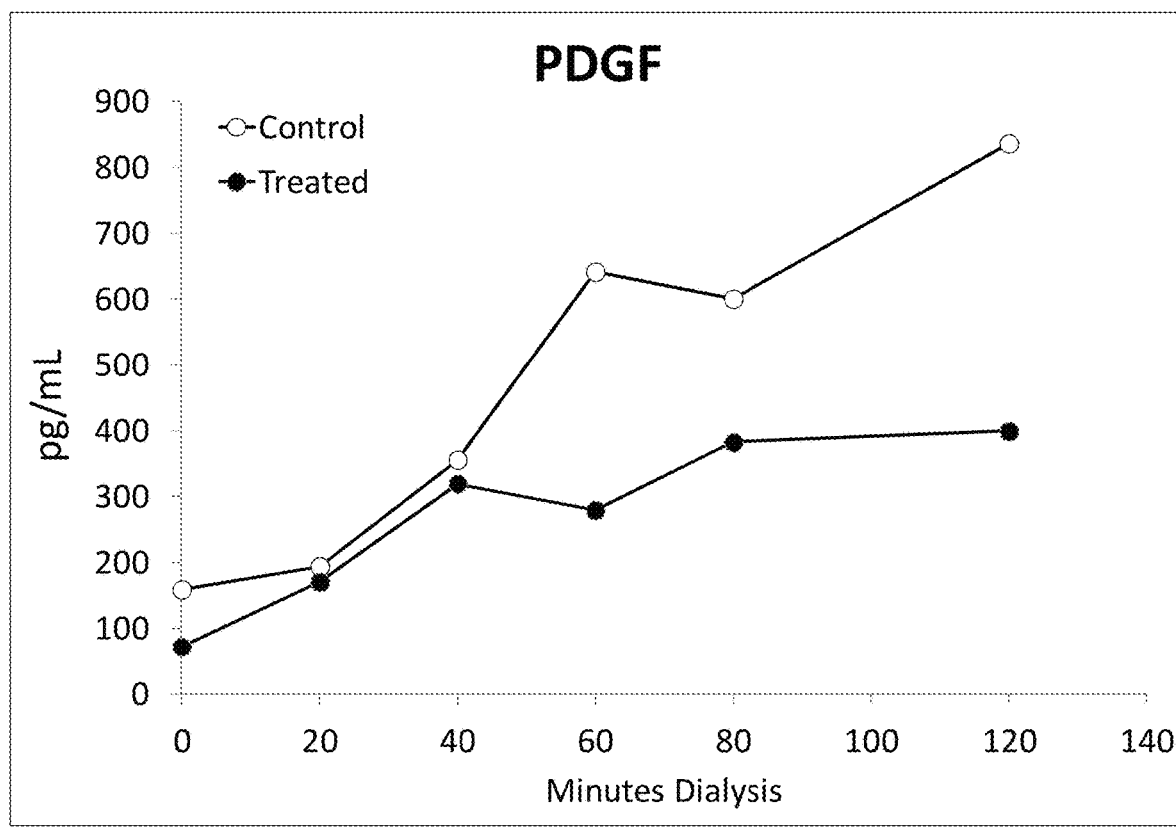
FIG. 4 presents data from an experiment in which an anti-AP antibody was added to human blood during an extracorporeal model of dialysis, wherein complement activation is known to occur. After incubation at 37° C., the levels of PDGF were measured using conventional methods. The data from this experiment demonstrate that the anti-AP antibody was able to inhibit production of PDGF in human blood.
Figure 5:
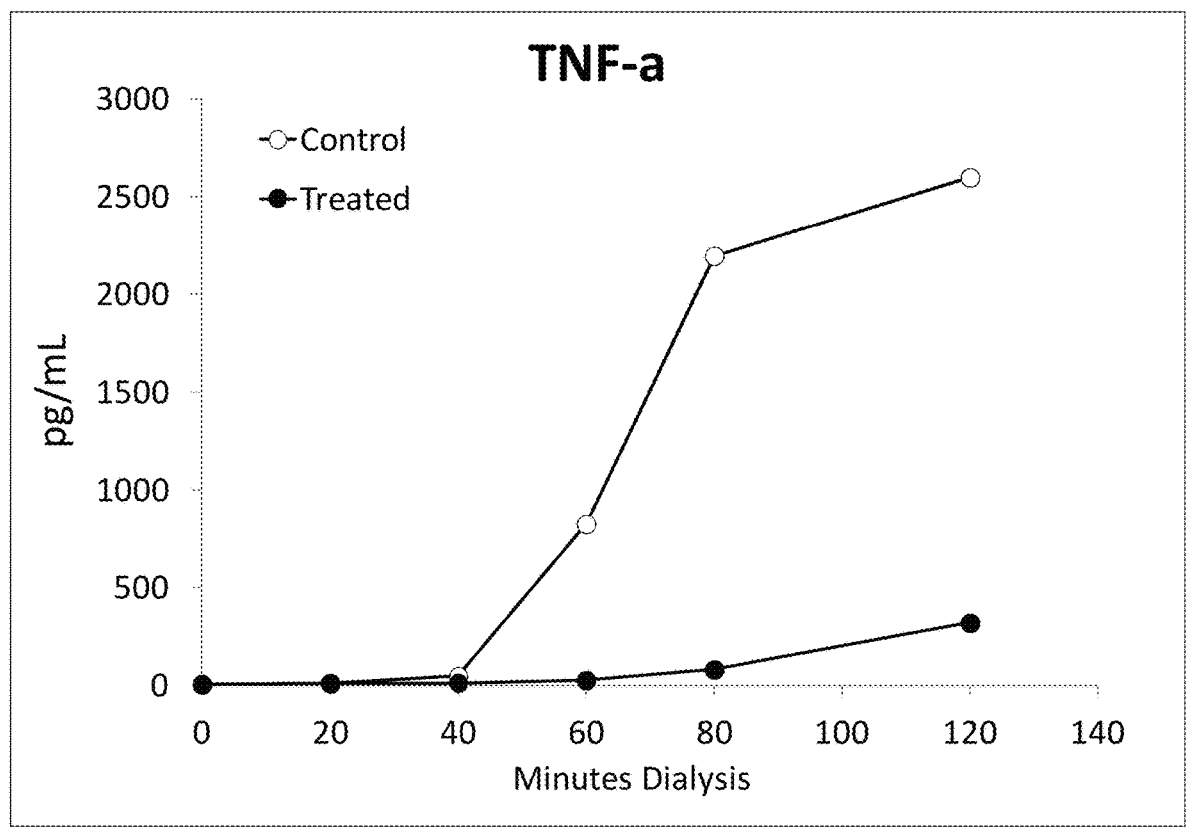
FIG. 5 presents data from an experiment in which an anti-AP antibody was added to human blood during an extracorporeal model of dialysis, wherein complement activation is known to occur. After incubation at 37° C., the levels of TNF-alpha were measured using conventional methods. The data from this experiment demonstrate that the anti-AP antibody was able to inhibit production of TNF-alpha in human blood.
Figure 6:
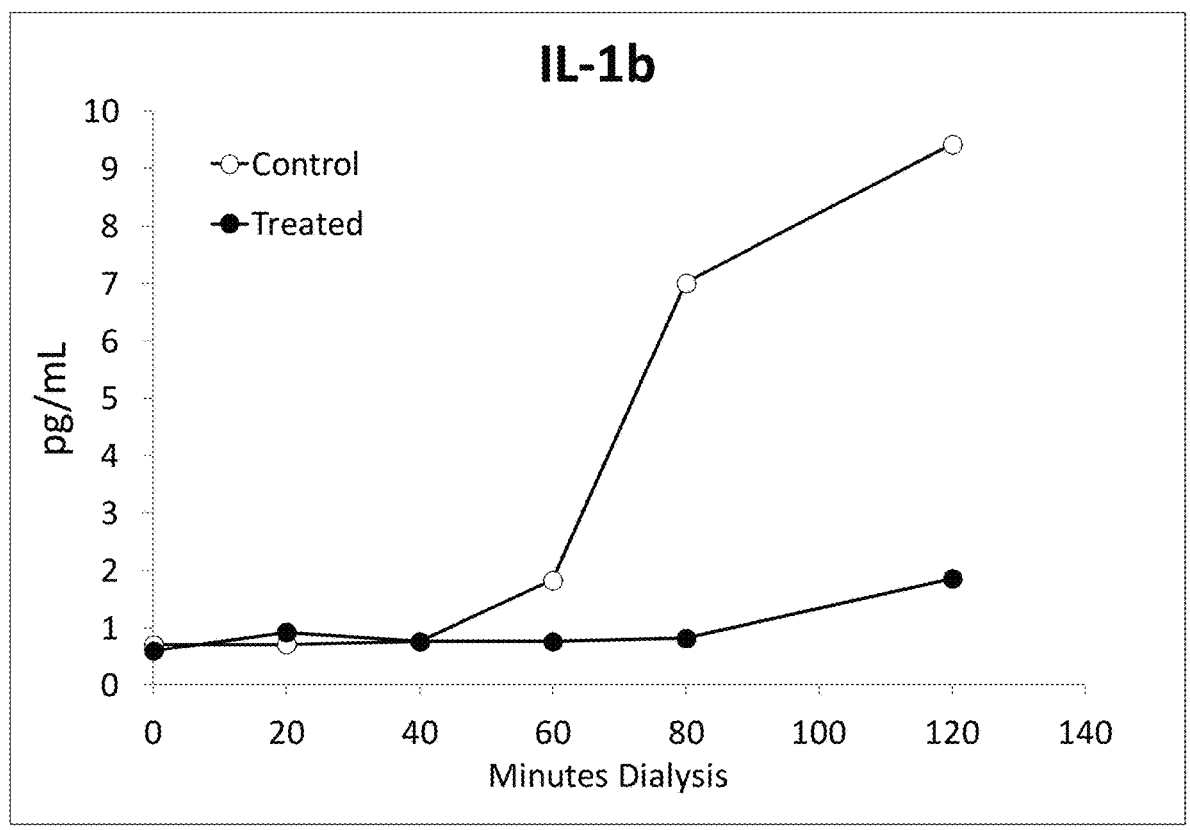
FIG. 6 presents data from an experiment in which an anti-AP antibody was added to human blood during an extracorporeal model of dialysis, wherein complement activation is known to occur. After incubation at 37° C., the levels of IL-1b were measured using conventional methods. The data from this experiment demonstrate that the anti-AP antibody was able to inhibit production of IL-1b in human blood

Example 1: Alternative Pathway Inhibiting Antibodies of the Invention Inhibit Production of VEGF, PDGF, TNF-a, and IL-1b An anti-AP antibody as described in Example 3 was added to human blood during an extracorporeal model of dialysis, wherein complement activation is known to occur. After incubation at 37° C., the levels of VEGF, PDGF, TNF-alpha, and IL-1b were measured using conventional methods. The data from these experiments demonstrate that the anti-AP antibody was able to inhibit production of VEGF, PDGF, TNF-alpha, and IL-1b in human blood wherein complement activation would otherwise occur. Graphical representations of the data from these experiments are presented in FIG. 3 (VEGF), FIG. 4 (PDGF), FIG. 5 (TNF-alpha), and FIG. 6 (IL-1b).

Example 2: Anti-AP Antibodies Inhibit AP and LDH Ex Vivo

Figure 7:
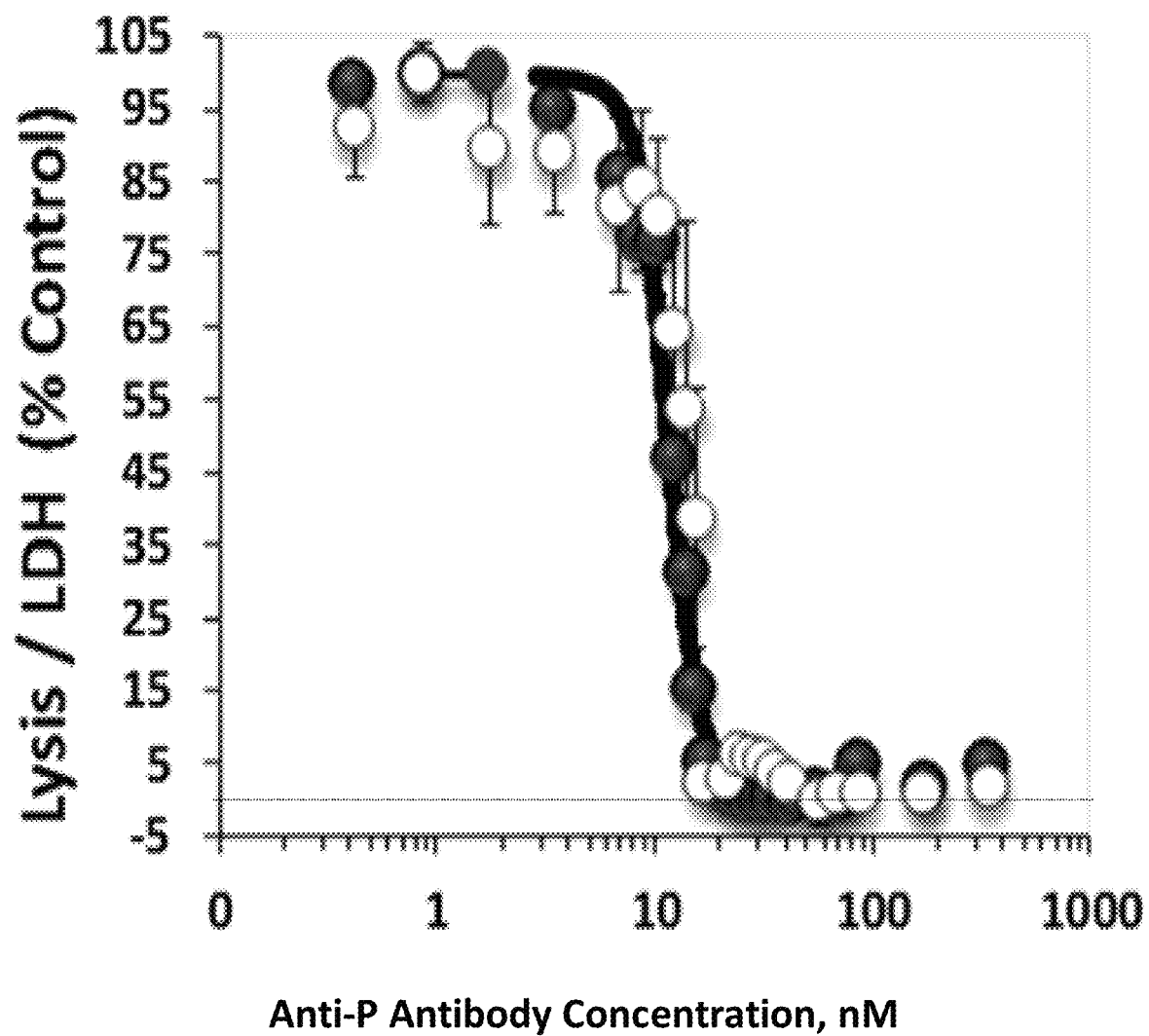
FIG. 7 illustrates Ex Vivo Inhibition of Cell Lysis—This graph is a representation of data collected from studies evaluating anti-P antibodies for their effect on MAC formation, cell lysis, and release of LDH (relative to control).

To test the activity of the antibody for AP inhibition, rabbit erythrocytes were incubated in 10% normal human serum in buffer that allows only AP activation to occur. (/Mg$^{2+}$/EGTA). These rRBCs activate the AP, Lysis of the cells results in a gradual decrease in light scattered by cells. When an AP specific antibody of the present invention was incubated with rRBCs at 37° C. in 10% NHS, the lysis was prevented y this antibody. This implies that the AP specific antibody of the present invention blocks AP. Plasma was evaluated by LDH to demonstrate that the AP specific antibody prevents LDH formation. Both lysis and LDH are critical parameters in ocular disease, the former demonstrates cell injury and the latter demonstrates cell death as dead cells release LDH. As shown in FIG. 7, both cell injury/lysis and LDH overlap.

Example 3: Anti-P Antibody Fab Inhibits CNV in Rhesus Model of Wet AMD

A humanized anti-properdin antibody used for this study is the Fab fragment of one of the full-length antibodies having the light chain variable domain 3CDRs of SEQ ID NO: 12 and the heavy chain variable domain 3CDRs of SEQ ID NO: 55. The material used for the study was evaluated at a concentration of 25.5 mg/mL. We used the Fab of the anti-P antibody instead of the IgG because the study involved a comparison with an anti-VEGF antibody in fab form Lucentis® (Genentech). The concentration of Lucentis in the vial is 10 mg/ml and the volume is 300 ul/vial. Concentration of the anti-P antibody was 25 mg/ml in phosphate buffered saline. The test article, reference article and control article were each administered via a single intravitreal injection performed in naive female rhesus monkeys which were 2.9-3.9 years old at the time of study assignment. Subjects weighed 3.0-4.8 kg on Day −1 (n=9).

Lucentis was administered at a dose of 500 ug/eye (the therapeutic dose for use in humans), while 1.25 mg/eye was used for the anti-P antibody (the highest concentration allowable based on our current formulation). Following administration of the injection, a laser was used to create nine spots of tissue injury on the retina of each eye of each animal. These lasered spots are known in the art to induce CNV in other animal models. Following the laser induction, a period of two weeks was allowed for healing and CNV formation. Following the two week post-op period, FA images were taken at the end of Week2, Week3 and Week4. Color images were taken at the end of Week2, Week3 and Week4. FA images were evaluated with the aid of the ImageJ program.

Figure 8:
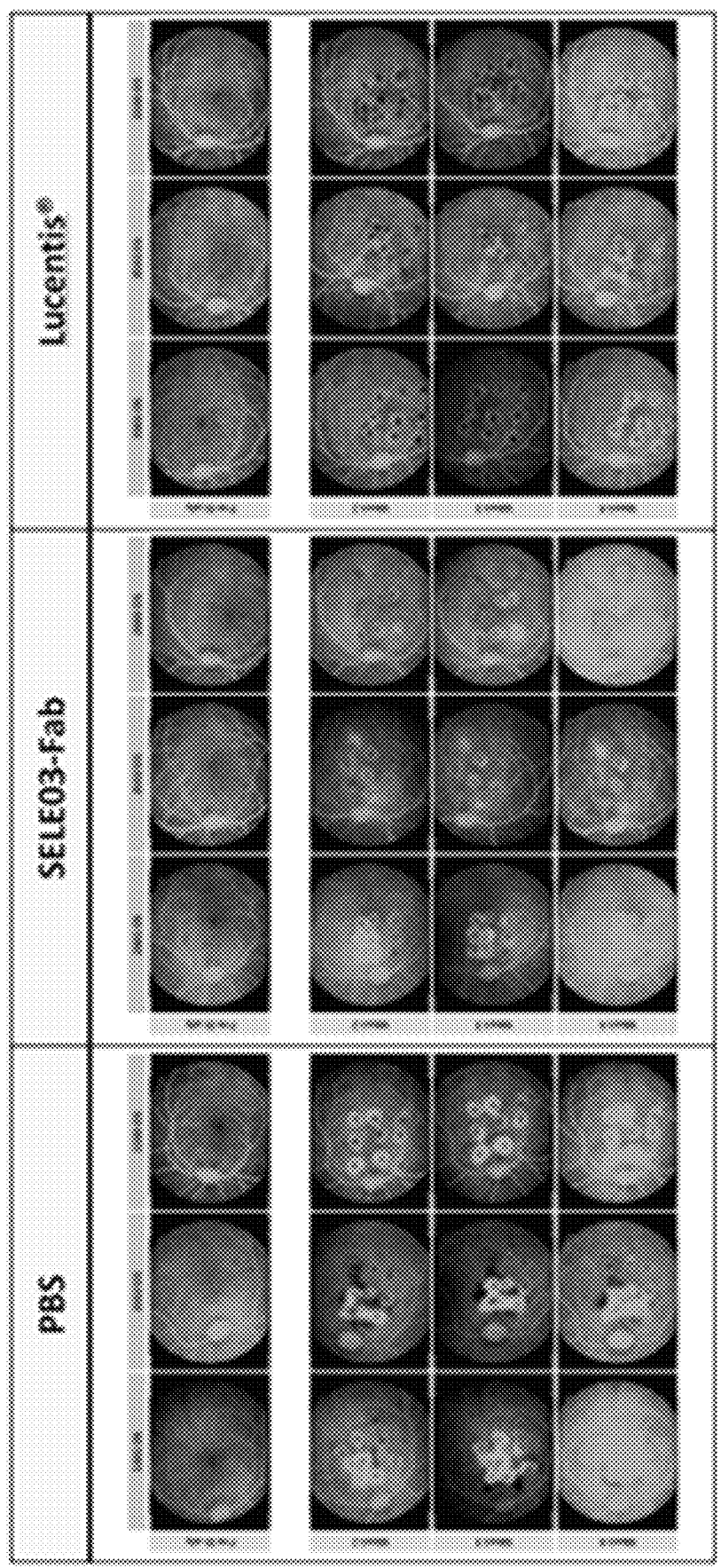
FIG. 8 illustrates images taken of rhesus monkey retinas taken from a rhesus model of CNV, wherein the reference drug was an anti-VEGF agent and the test drug was one of the invention's anti-P antibodies.
Figure 9:
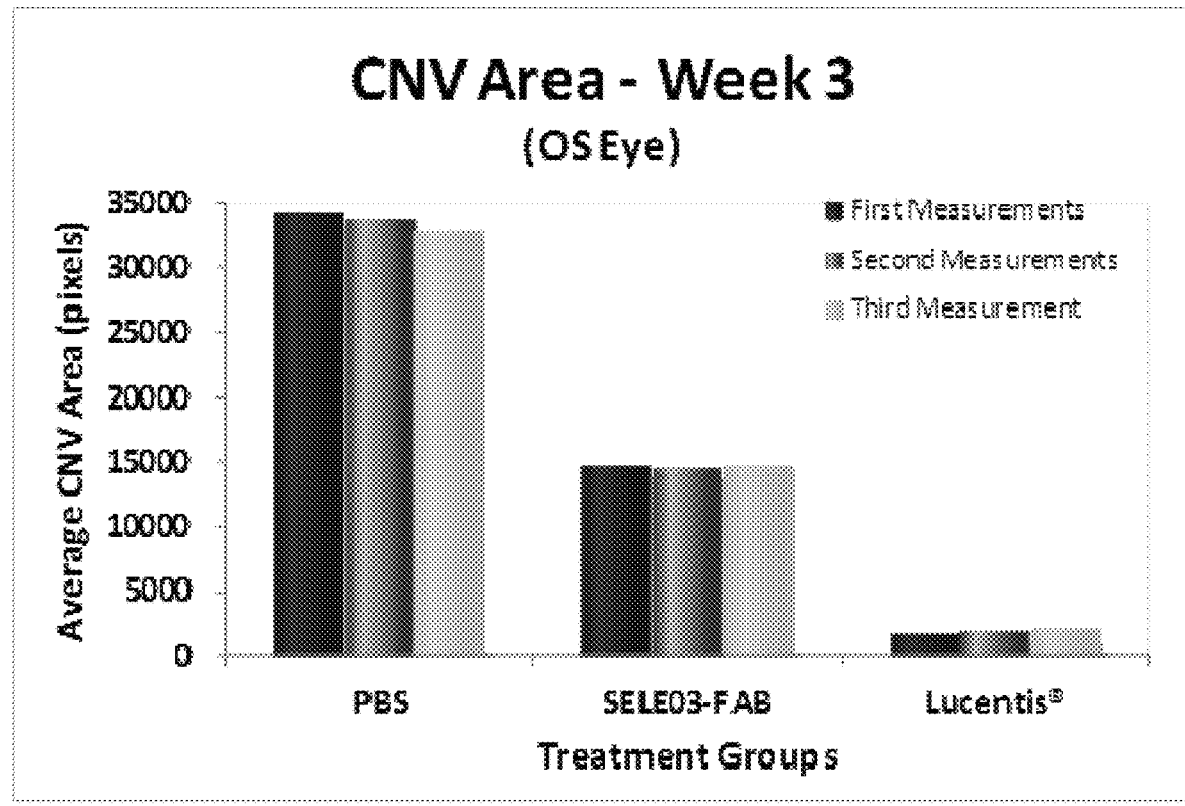
FIG. 9 illustrates a graphical representation of the data collected from quantification of CNV areas observed in week 3 of rhesus monkey model of Wet AMD and CNV— the methods used to quantify the extent of CNV in each study group is described in the specification of this application.

CNV appearing on FA images was quantified using an ImageJ program which is known and accepted within the art. FIG. 8 displays the images taken at Week2, Week3, and Week4. Due to overexposure of Week4 images, meaningful FA data analysis was only possible for images taken at the end of Week2 and Week3. The results of the ImageJ analysis are presented in FIG. 9 (corresponding to Week2). As the results of this study demonstrate, the anti-P antibody was effective in inhibiting CNV. As expected, the anti-VEGF inhibitor was more effective at preventing vascular growth in the weeks following laser induction. As previously discussed in this application, anti-VEGF agents inhibit all new vessel growth. The purpose of this invention is to offer a treatment for CNV which inhibits excessive growth of new vessels without inhibiting new vessel growth which will be required for wound healing.

Example 4: Anti-P Antibody Fab Inhibits Hemolysis in Rhesus Model of Wet AMD

Figure 11:
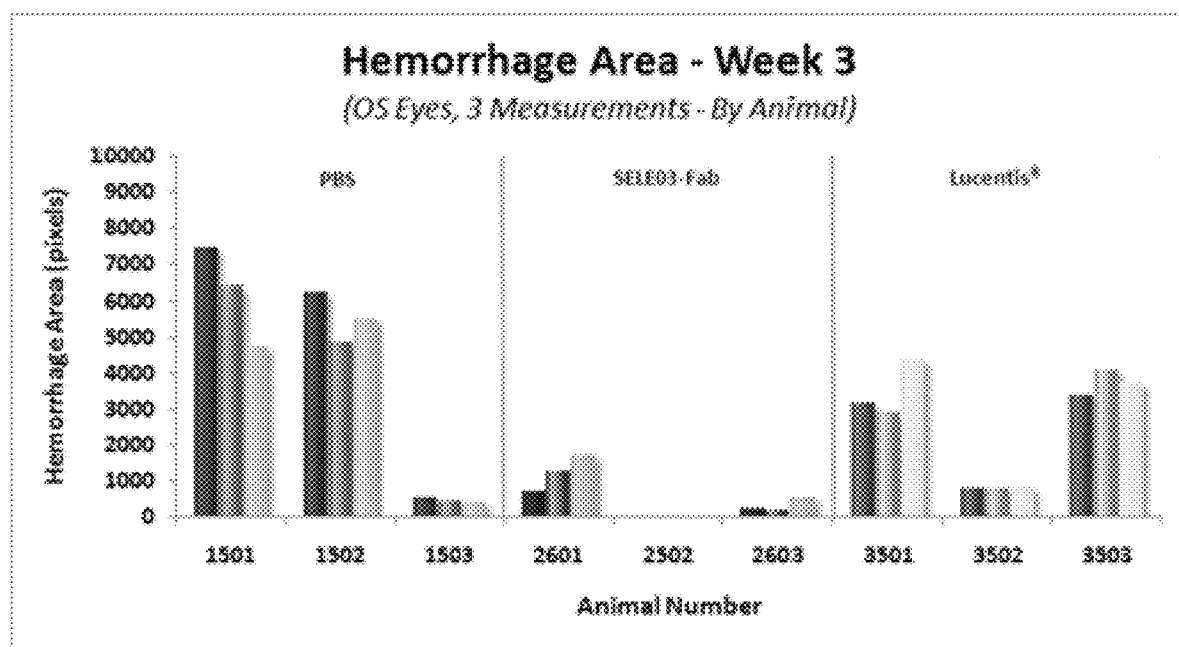
FIG. 11 illustrates the quantification of Hemorrhage observed in week 3 of rhesus monkey model of Wet AMD and CNV—the methods used to quantify the extent of hemorrhaging in each study group is described in the specification of this application.

Hemorrhage quantification was conducted using the FA images which were originally taken for evaluation of the CNV study described in Example 3 above. The black areas around the CNV and laser spots were identified by as hemorrhage (see FIG. 10). The black regions were present mostly around the areas of CNV and underneath the CNV. Black spots were also noted in the centers of the circular tissue injuries created by the laser-induction of CNV. These regions were quantified using the ImageJ, using methods similar to those used for quantification of CNV, as discussed in Example 3. The results of the quantitative evaluation for hemorrhage after Week 3 are presented in FIG. 11.

Figure 12:
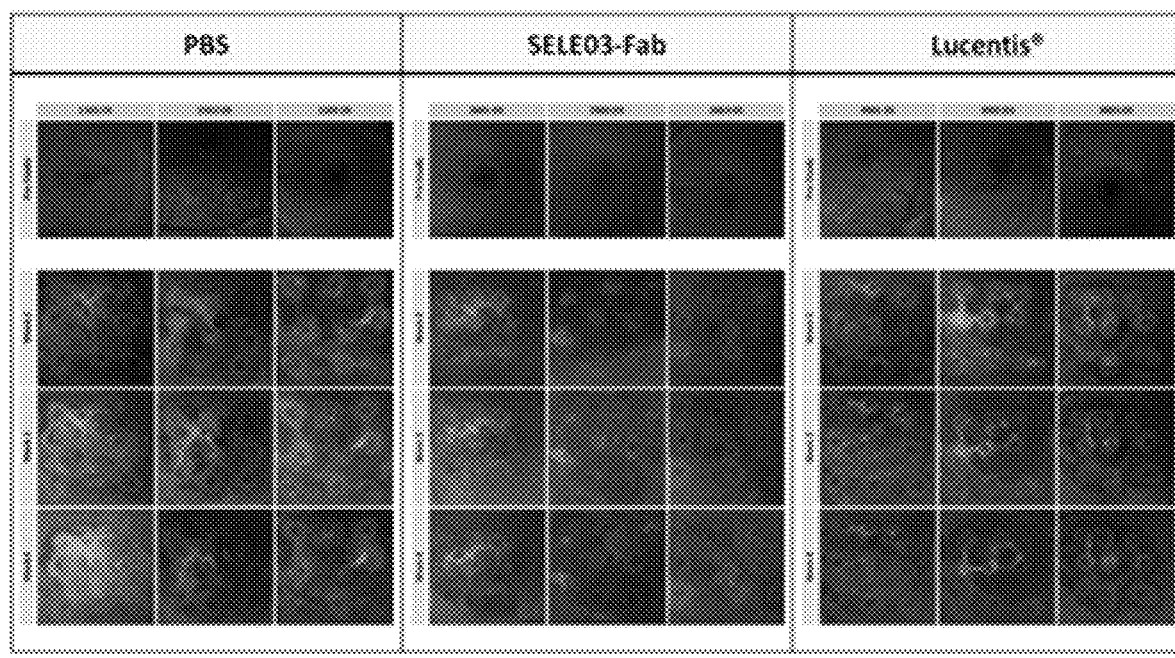
FIG. 12 illustrates Images of Study Subject Eyes—These images are from a rhesus monkey model of Wet AMD. The images, originally in color, have been converted to grayscale for this application.
Figure 14:
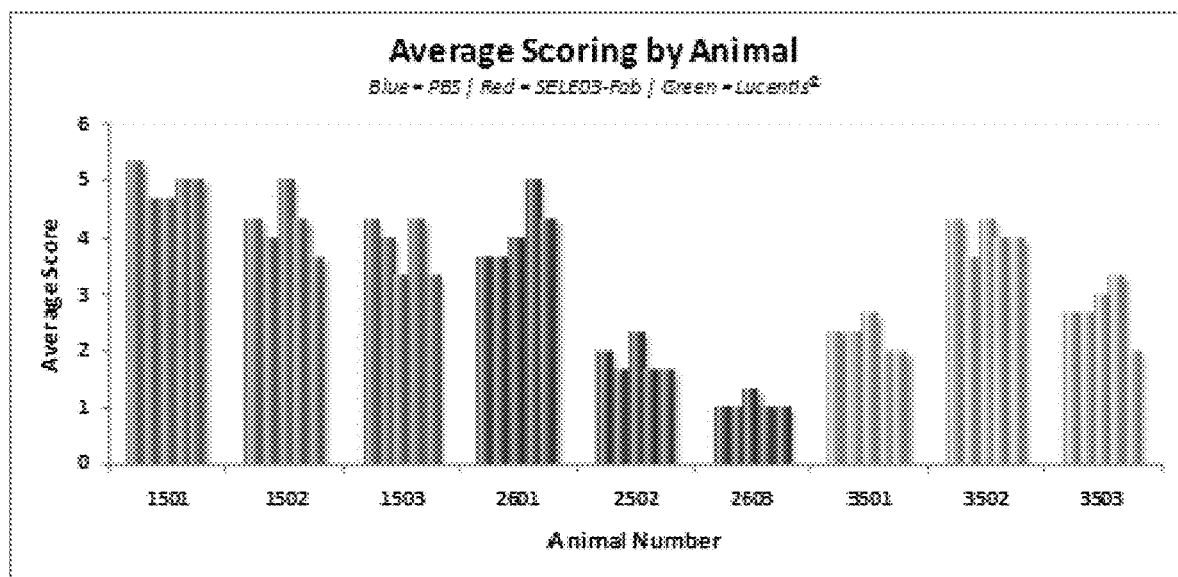
FIG. 14 illustrates quantification of Fibrosis—The above graph presents the results of the observer grades for extent of fibrosis in each subject animal from the rhesus monkey CNV study. As can be seen from the data provided above, the anti-P antibody substantially reduced fibrosis in 2 out of the 3 animals treated.

Example 5: Anti-P Antibody Fab Inhibits Retinal Fibrosis in Rhesus Model of Wet AMD FIG. 12 shows the color images (converted to grayscale for purposes of this application) taken from the rhesus monkey study described in examples 3 through 4 above were used to evaluate the study subjects for development of retinal fibrosis following treatment and induction of CNV. Retinal fibrosis appears in the color images as lightly colored "stringy" or obscurely patterned areas surrounding and extending from the laser spots. Using a scale from 0 to 6, with zero being no appearance of fibrosis and 6 being the appearance of the most extensive fibrosis, multiple observers scored the full color images for visualization of fibrosis on each image. Observers were blinded to the identification of the images as being from the test, reference or control group. Examples of visualized fibrosis and the grading key provided to the observers are provided in FIG. 13. FIG. 14 provides a graphical representation of the quantitative results of the observers' evaluation for fibrosis. As can be seen from the data, the anti-P antibody substantially reduced fibrosis in 2 out of the 3 animals treated. While some improvement in fibrosis was also seen in 2 out of 3 animals in the Lucentis treated group, the improvement in fibrosis seen in the anti-P antibody treated animals was significantly greater than was seen in the Lucentis treated group.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

The invention claimed is:

1. A method of treating ocular pathologies associated with fibrosis and hemorrhage within and around the macula of a subject in need thereof, the method comprising: administering to the subject a therapeutically effective amount of an anti-Bb antibody or antigen binding fragment thereof that binds to a component of alternative pathway and inhibits alternative pathway activation, wherein the anti-Bb antibody or antigen binding fragment thereof includes a light chain variable domain including 3CDRs of SEQ ID NO: 36 and a heavy chain variable domain including 3CDRs of SEQ ID NO: 79.

2. The method of claim 1, wherein the antibody or antigen binding fragment thereof inhibits alternative complement pathway activation without inhibiting classical pathway activation.

3. The method of claim 1, wherein the antibody or antigen binding fragment thereof selectively inhibits C3a, C5a, C3b, C5b, and C5b-9 produced by the alternative pathway, without inhibiting any of the classical pathway's ability to produce C3a, C5a, C3b, C5b, and C5b-9.

4. The method of claim 1, wherein the antibody or antigen binding fragment thereof selectively inhibits formation of PC3bBb produced by the alternative pathway.

5. The method of claim 1, wherein the antibody or antigen binding fragment thereof neutralizes the component of the alternative pathway function.

6. The method of claim 1, wherein the therapeutically effective amount of antibody or antigen binding fragment thereof is an amount effective for comprehensive treatment of macular degeneration, geographic atrophy and retinal fibrosis.

7. The method of claim 1, wherein the subject has dry age-related macular degeneration and the therapeutically effective amount of antibody or antigen binding fragment thereof is an amount of antibody effective to treat the dry age-related macular degeneration.

8. The method of claim 1, wherein the subject has wet age-related macular degeneration and the therapeutically effective amount of antibody or antigen binding fragment thereof is an amount of anti-properdin antibody effective to treat the wet age-related macular degeneration.

9. The method of claim 1, wherein the subject has geographic atrophy and the therapeutically effective amount of antibody or antigen binding fragment thereof is an amount of antibody or antigen binding fragment thereof effective to treat the geographic atrophy.

10. The method of claim 1, wherein the subject has geographic atrophy post onset of wet age-related macular degeneration and the therapeutically effective amount of antibody or antigen binding fragment thereof is an amount of antibody or antigen binding fragment thereof effective to treat the geographic atrophy.

11. The method of claim 1, wherein the subject has geographic atrophy post onset of dry age-related macular degeneration and the therapeutically effective amount of antibody or antigen binding fragment thereof is an amount of antibody or antigen binding fragment thereof effective to treat the geographic atrophy.

12. The method of claim 1, wherein the subject has early-stage age-related macular degeneration or excessive drusen pre-age-related macular degeneration and the therapeutically effective amount of antibody or antigen binding fragment thereof is an amount of antibody or antigen binding fragment thereof effective to inhibit onset of age-related macular degeneration.

13. A method of treating ocular disorders in a subject in need thereof, comprising administering to the subject undergoing anti-VEGF, anti-PDGF treatment a therapeutically effective amount of an anti-Bb antibody or antigen binding fragment thereof that binds to a component of alternative pathway and inhibits alternative pathway activation, wherein the anti-Bb antibody or antigen binding fragment thereof includes a light chain variable domain including 3CDRs of SEQ ID NO: 36 and a heavy chain variable domain including 3CDRs of SEQ ID NO: 79.

14. The method of claim 13, wherein the antibody or antigen binding fragment thereof has a reduced effector function.

15. The method of claim 13, wherein the antibody is a hybrid of two antibody isoforms.

16. The method of claim 13, wherein the antibody or antigen binding fragment thereof binds to a component of alternative pathway C3 convertase and inhibits alternative pathway activation.

17. The method of claim 13, wherein the antibody or antigen binding fragment thereof selectively inhibits C3a, C5a, C3b, C5b, and C5b-9 produced by the alternative pathway but not the classical pathway.

* * * * *

SEQUENCE LISTING

```
<160> NUMBER OF SEQ ID NOS: 120

<210> SEQ ID NO 1
<211> LENGTH: 112
<212> TYPE: PRT
<213> ORGANISM: Oryctolagus cuniculus

<400> SEQUENCE: 1

Ala Val Val Leu Thr Gln Thr Ala Ser Pro Val Ser Gly Val Val Gly
1               5                   10                  15

Gly Thr Val Thr Ile Asn Cys Gln Ala Ser Glu Asn Ile Tyr Ser Arg
            20                  25                  30

Leu Ala Trp Tyr Gln Gln Lys Pro Gly Gln Pro Arg Val Leu Ile
        35                  40                  45

Tyr Tyr Ala Ser Asp Leu Ala Ser Gly Val Pro Ser Arg Phe Gly Gly
    50                  55                  60

Ser Gly Ser Gly Thr Asp Tyr Thr Leu Thr Ile Ser Asp Leu Glu Cys
65                  70                  75                  80

Ala Asp Ala Ala Thr Tyr Tyr Cys His Ser Tyr Tyr Trp Asn Ser Ala
                85                  90                  95
```

```
Tyr Ser Asp Asn Thr Phe Gly Gly Thr Glu Val Val Glu Gly
            100                 105                 110

<210> SEQ ID NO 2
<211> LENGTH: 111
<212> TYPE: PRT
<213> ORGANISM: Oryctolagus cuniculus

<400> SEQUENCE: 2

Ala Tyr Asp Leu Thr Gln Thr Pro Ala Ser Val Glu Ala Ala Val Gly
 1               5                  10                  15

Gly Thr Val Thr Ile Asn Cys Gln Ala Ser Asp Asn Ile Tyr Ser Leu
            20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln His Tyr Asp Tyr Asn Tyr
                85                  90                  95

Leu Asp Val Ala Phe Gly Gly Gly Thr Glu Val Val Val Lys Gly
            100                 105                 110

<210> SEQ ID NO 3
<211> LENGTH: 111
<212> TYPE: PRT
<213> ORGANISM: Oryctolagus cuniculus

<400> SEQUENCE: 3

Ala Tyr Asp Leu Thr Gln Thr Pro Ala Ser Val Glu Ala Ala Val Gly
 1               5                  10                  15

Gly Thr Val Thr Ile Asn Cys Gln Ala Ser Asp Asn Ile Tyr Ser Leu
            20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln His Tyr Asp Tyr Asn Tyr
                85                  90                  95

Leu Asp Val Ala Phe Gly Gly Gly Thr Glu Val Val Val Lys Gly
            100                 105                 110

<210> SEQ ID NO 4
<211> LENGTH: 111
<212> TYPE: PRT
<213> ORGANISM: Oryctolagus cuniculus

<400> SEQUENCE: 4

Ala Tyr Asp Met Thr Gln Thr Pro Phe Ser Val Ser Ala Ala Val Gly
 1               5                  10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Arg Pro Lys Leu Leu Ile
            35                  40                  45
```

```
Tyr Arg Ala Ser Thr Leu Ala Ser Gly Val Pro Ser Arg Phe Ser Gly
    50                  55                  60

Ser Arg Ser Gly Thr Gln Phe Thr Leu Thr Ile Ser Gly Val Glu Cys
65                  70                  75                  80

Ala Asp Ala Ala Thr Tyr Tyr Cys Gln Gln His Trp Asp Tyr Asp Tyr
                85                  90                  95

Ile Asp Val Ala Phe Gly Gly Gly Thr Glu Val Val Val Lys Gly
            100                 105                 110
```

<210> SEQ ID NO 5
<211> LENGTH: 111
<212> TYPE: PRT
<213> ORGANISM: Oryctolagus cuniculus

<400> SEQUENCE: 5

```
Asp Val Val Met Thr Gln Thr Pro Ser Ser Val Glu Ala Ala Val Gly
1               5                   10                  15

Gly Thr Val Thr Ile Lys Cys Gln Ala Ser Glu Asn Ile Tyr Ser Tyr
            20                  25                  30

Leu Ala Trp Tyr Gln Gln Lys Pro Gly Gln Pro Pro Lys Leu Leu Ile
        35                  40                  45

Tyr Lys Ala Ser Tyr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Leu Ser Thr Ile Ala Ser Ala Ser
                85                  90                  95

Asn Phe Asp Ala Phe Gly Gly Gly Thr Glu Val Val Val Lys Gly
            100                 105                 110
```

<210> SEQ ID NO 6
<211> LENGTH: 114
<212> TYPE: PRT
<213> ORGANISM: Oryctolagus cuniculus

<400> SEQUENCE: 6

```
Asp Pro Val Leu Thr Gln Thr Ala Ser Ser Val Ser Ala Pro Val Gly
1               5                   10                  15

Gly Thr Val Thr Ile Ser Cys Gln Ser Ser Gln Ser Val Tyr Arg Ser
            20                  25                  30

Asn Asn Val Ala Trp Tyr Gln Gln Lys Pro Gly Lys Pro Pro Lys Leu
        35                  40                  45

Leu Ile Tyr Glu Ala Ser Ser Leu Ala Ser Gly Val Pro Ser Arg Phe
    50                  55                  60

Thr Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Gly Tyr Ser Ser
                85                  90                  95

Ser Val Asp Phe Phe Ala Phe Gly Gly Gly Thr Glu Val Val Val
            100                 105                 110

Lys Gly
```

<210> SEQ ID NO 7
<211> LENGTH: 108
<212> TYPE: PRT
<213> ORGANISM: Mus musculus

<400> SEQUENCE: 7

```
Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Ser Asp Ala
            20                  25                  30

Val Ala Trp Phe Gln Gln Lys Pro Gly Gln Ser Pro Lys Leu Leu Ile
        35                  40                  45

Tyr Ser Pro Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys Arg
            100                 105
```

<210> SEQ ID NO 8
<211> LENGTH: 107
<212> TYPE: PRT
<213> ORGANISM: Homo sapiens

<400> SEQUENCE: 8

```
Asp Ile Gln Met Thr Gln Ser His Lys Phe Met Ser Thr Ser Val Gly
1               5                   10                  15

Asp Arg Val Thr Ile Thr Cys Lys Ala Ser Gln Asp Val Ser Asp Ala
            20                  25                  30

Val Ala Trp Phe Gln Gln Lys Pro Gly Lys Ser Pro Lys Leu Leu Ile
        35                  40                  45

Tyr Ser Pro Ser Tyr Arg Tyr Thr Gly Val Pro Ser Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gln Gly Thr Lys Leu Glu Ile Lys
            100                 105
```

<210> SEQ ID NO 9
<211> LENGTH: 107
<212> TYPE: PRT
<213> ORGANISM: Homo sapiens

<400> SEQUENCE: 9

```
Asp Ile Gln Met Thr Gln Ser His Lys Phe Met Ser Thr Ser Val Gly
1               5                   10                  15

Asp Arg Val Ser Ile Ser Cys Lys Ala Ser Gln Asp Val Ser Asp Ala
            20                  25                  30

Val Ala Trp Phe Gln Gln Lys Pro Gly Lys Ser Pro Lys Leu Leu Ile
        35                  40                  45

Tyr Ser Pro Ser Tyr Arg Tyr Thr Gly Val Pro Ser Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gln Gly Thr Lys Leu Glu Ile Lys
            100                 105
```

<210> SEQ ID NO 10
<211> LENGTH: 107
<212> TYPE: PRT
<213> ORGANISM: Homo sapiens

<400> SEQUENCE: 10

```
Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gln Gly Thr Lys Leu Glu Ile Lys
            100                 105
```

<210> SEQ ID NO 11
<211> LENGTH: 108
<212> TYPE: PRT
<213> ORGANISM: Homo sapiens

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Asn Tyr Asp Asn Leu Pro Leu
                85                  90                  95

Thr Phe Gly Gly Gly Thr Lys Val Glu Ile Lys Arg
            100                 105
```

<210> SEQ ID NO 12
<211> LENGTH: 108
<212> TYPE: PRT
<213> ORGANISM: Homo sapiens

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Ser Phe
            20                  25                  30

Leu Asn Trp Tyr Gln Gln Lys Ser Gly Lys Ala Pro Lys Leu Leu Ile
        35                  40                  45

Phe Ala Thr Ser Arg Leu Gln Ser Gly Val Pro Ser Arg Ile Ser Gly
    50                  55                  60
```

Ser Gly Ser Gly Thr Asp Phe Thr Leu Thr Ile Ser Gly Leu Gln Pro
65                  70                  75                  80

Glu Asp Phe Ala Thr Phe Tyr Cys Gln Gln Ser Tyr Ser Ile Pro Leu
                85                  90                  95

Thr Phe Gly Gly Gly Thr Lys Val Asp Ile Lys Arg
            100                 105

<210> SEQ ID NO 13
<211> LENGTH: 108
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Trp
                85                  90                  95

Thr Phe Gly Gln Gly Thr Lys Val Glu Ile Lys Arg
            100                 105

<210> SEQ ID NO 14
<211> LENGTH: 101
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Leu Gln Lys Pro Gly Gln Ser Pro Gln Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Asn Thr Leu Pro Trp
                85                  90                  95

Thr Phe Gly Gln Gly
            100

<210> SEQ ID NO 15
<211> LENGTH: 101
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe

```
                20                  25                  30
Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 16
<211> LENGTH: 101
<212> TYPE: PRT
<213> ORGANISM: Homo sapiens

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Gly Asn Thr Leu Pro Trp
                85                  90                  95

Thr Phe Gly Gln Gly
            100

<210> SEQ ID NO 17
<211> LENGTH: 101
<212> TYPE: PRT
<213> ORGANISM: Homo sapiens

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Phe Phe
            20                  25                  30

Leu Asn Trp Phe Gln Gln Arg Pro Gly Gln Ser Pro Arg Arg Leu Ile
            35                  40                  45

Tyr Tyr Thr Ser Arg Tyr His Ser Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln His Gly Asn Thr Leu Pro Trp
                85                  90                  95

Thr Phe Gly Gln Gly
            100

<210> SEQ ID NO 18
<211> LENGTH: 101
<212> TYPE: PRT
```

<213> ORGANISM: Homo sapiens

<400> SEQUENCE: 18

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Gly Asn Thr Leu Pro Trp
                85                  90                  95

Thr Phe Gly Gln Gly
            100

<210> SEQ ID NO 19
<211> LENGTH: 101
<212> TYPE: PRT
<213> ORGANISM: Homo sapiens

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Leu Gln Lys Pro Gly Gln Ser Pro Gln Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Asn Thr Leu Pro Trp
                85                  90                  95

Thr Phe Gly Gln Gly
            100

<210> SEQ ID NO 20
<211> LENGTH: 101
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 21
<211> LENGTH: 101
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 22
<211> LENGTH: 101
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 23
<211> LENGTH: 101
<212> TYPE: PRT
<213> ORGANISM: Homo sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

-continued

Tyr Tyr Thr Ser Arg Tyr His Ser Gly Ile Pro Pro Arg Phe Ser Gly
    50                  55                  60

Ser Gly Tyr Gly Thr Glu Phe Thr Phe Thr Ile Ser Ser Leu Glu Ala
65                  70                  75                  80

Glu Asp Ala Ala Thr Tyr Tyr Cys Gln His Gly Asn Thr Leu Pro Trp
                85                  90                  95

Thr Phe Gly Gln Gly
            100

<210> SEQ ID NO 24
<211> LENGTH: 101
<212> TYPE: PRT
<213> ORGANISM: Homo sapiens

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Gly Asn Thr Leu Pro Trp
                85                  90                  95

Thr Phe Gly Gln Gly
            100

<210> SEQ ID NO 25
<211> LENGTH: 101
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
            100

<210> SEQ ID NO 26
<211> LENGTH: 108
<212> TYPE: PRT
<213> ORGANISM: Homo sapiens

<400> SEQUENCE: 26

Asp Ile Gln Met Thr Gln Thr Thr Ser Ser Leu Ser Ala Ser Leu Gly

```
              1               5                  10                 15
Asp Arg Val Thr Ile Ser Cys Arg Ala Ser Gln Asp Ile Ser Phe Phe
                20                  25                  30

Leu Asn Trp Tyr Gln Gln Lys Pro Asp Gly Thr Val Lys Leu Leu Ile
            35                  40                  45

Tyr Tyr Thr Ser Arg Tyr His Ser Gly Val Pro Ser Arg Phe Ser Gly
        50                  55                  60

Ser Gly Ser Gly Thr Asp Phe Ser Leu Thr Ile Asn Asn Leu Glu Gln
65                  70                  75                  80

Glu Asp Phe Ala Thr Tyr Phe Cys Gln His Gly Asn Thr Leu Pro Trp
                85                  90                  95

Thr Phe Gly Gly Gly Thr Lys Leu Glu Ile Lys Arg
                100                 105
```

<210> SEQ ID NO 27
<211> LENGTH: 101
<212> TYPE: PRT
<213> ORGANISM: Homo sapiens

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Gly Asn Thr Leu Pro Trp
                85                  90                  95

Thr Phe Gly Gln Gly
                100
```

<210> SEQ ID NO 28
<211> LENGTH: 101
<212> TYPE: PRT
<213> ORGANISM: Homo sapiens

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Leu Gln Lys Pro Gly Gln Ser Pro Gln Leu Leu Ile
            35                  40                  45

Tyr Tyr Thr Ser Arg Tyr His Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Gly Asn Thr Leu Pro Trp
                85                  90                  95

Thr Phe Gly Gln Gly
                100
```

```
<210> SEQ ID NO 29
<211> LENGTH: 101
<212> TYPE: PRT
<213> ORGANISM: Homo sapiens

<400> SEQUENCE: 29

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Gly Asn Thr Leu Pro Trp
                85                  90                  95

Thr Phe Gly Gln Gly
            100

<210> SEQ ID NO 30
<211> LENGTH: 101
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Ile Pro Pro Arg Phe Ser Gly
50                  55                  60

Ser Gly Tyr Gly Thr Glu Phe Thr Phe Thr Ile Ser Ser Leu Glu Ala
65                  70                  75                  80

Glu Asp Ala Ala Thr Tyr Tyr Cys Gln His Gly Asn Thr Leu Pro Trp
                85                  90                  95

Thr Phe Gly Gln Gly
            100

<210> SEQ ID NO 31
<211> LENGTH: 108
<212> TYPE: PRT
<213> ORGANISM: Homo sapiens

<400> SEQUENCE: 31

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Phe Cys Gln His Gly Asn Thr Leu Pro Trp
            85                  90                  95

Thr Phe Gly Gln Gly Thr Lys Leu Glu Ile Lys Arg
            100                 105

<210> SEQ ID NO 32
<211> LENGTH: 108
<212> TYPE: PRT
<213> ORGANISM: Homo sapiens

<400> SEQUENCE: 32

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
            85                  90                  95

Thr Phe Gly Gln Gly Thr Lys Leu Glu Ile Lys Arg
            100                 105

<210> SEQ ID NO 33
<211> LENGTH: 156
<212> TYPE: PRT
<213> ORGANISM: Mus musculus

<400> SEQUENCE: 33

Lys Glu Ile His Gln Ala Gly Lys Gly Ile Lys Met Lys Ser Gln Thr
1               5                   10                  15

Gln Val Phe Val Phe Leu Leu Leu Cys Val Ser Gly Ala His Gly Ser
            20                  25                  30

Ile Val Met Thr Gln Thr Pro Lys Phe Leu Leu Val Ser Ala Gly Asp
            35                  40                  45

Arg Ile Thr Ile Thr Cys Lys Ala Ser Gln Ser Val Asn Asn Asp Val
    50                  55                  60

Ala Trp Tyr Gln Gln Lys Pro Gly Gln Ser Pro Lys Leu Leu Ile Tyr
65                  70                  75                  80

Tyr Ala Ser Asn Arg Tyr Thr Gly Val Pro Asp Arg Phe Thr Gly Ser
            85                  90                  95

Gly Tyr Gly Thr Asp Phe Thr Phe Thr Ile Thr Thr Val Lys Ala Glu
            100                 105                 110

Asp Leu Ala Val Tyr Phe Cys Gln Gln Asp Tyr Ser Ser Pro Leu Thr
            115                 120                 125

Phe Gly Ala Gly Thr Lys Leu Glu Leu Lys Arg Ala Asp Ala Ala Pro
            130                 135                 140

Thr Val Ser Ala Cys Thr Lys Gly Glu Phe Ala Ala
145                 150                 155

<210> SEQ ID NO 34
<211> LENGTH: 101
<212> TYPE: PRT
<213> ORGANISM: Mus musculus

```
<400> SEQUENCE: 34

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Phe Phe
                20                  25                  30

Leu Asn Trp Tyr Gln Gln Lys Pro Asp Gly Thr Val Lys Leu Leu Ile
            35                  40                  45

Tyr Tyr Thr Ser Arg Tyr His Ser Gly Val Pro Ser Arg Phe Ser Gly
50                  55                  60

Ser Gly Ser Gly Thr Asp Phe Ser Leu Thr Ile Asn Asn Leu Glu Gln
65                  70                  75                  80

Glu Asp Phe Ala Thr Tyr Phe Cys Gln His Gly Asn Thr Leu Pro Trp
                85                  90                  95

Thr Phe Gly Gly Gly
            100

<210> SEQ ID NO 35
<211> LENGTH: 108
<212> TYPE: PRT
<213> ORGANISM: Mus musculus

<400> SEQUENCE: 35

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Asp Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asp Glu Tyr Pro Trp
                85                  90                  95

Thr Phe Gly Gly Gly Thr Lys Leu Glu Ile Lys Arg
            100                 105

<210> SEQ ID NO 36
<211> LENGTH: 108
<212> TYPE: PRT
<213> ORGANISM: Homo sapiens

<400> SEQUENCE: 36

Asp Val Gln Ile Thr Gln Ser Pro Ser Thr Leu Ser Ala Ser Pro Gly
1               5                   10                  15

Asp Arg Ile Thr Ile Thr Cys Arg Ala Ser Lys Ser Ile Ser Lys Tyr
                20                  25                  30

Leu Ala Trp Tyr Gln Asp Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Met Tyr Tyr Cys Gln Gln His Asp Glu Tyr Pro Trp
                85                  90                  95
```

```
Thr Phe Gly Gln Gly Thr Lys Leu Glu Ile Lys Arg
            100                 105
```

<210> SEQ ID NO 37
<211> LENGTH: 108
<212> TYPE: PRT
<213> ORGANISM: Homo sapiens

<400> SEQUENCE: 37

```
Asp Val Gln Ile Thr Gln Ser Pro Ser Tyr Leu Ser Ala Ser Pro Gly
1               5                   10                  15

Asp Thr Ile Thr Ile Thr Cys Arg Ala Ser Lys Ser Ile Ser Lys Tyr
            20                  25                  30

Leu Ala Trp Tyr Gln Asp Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Met Tyr Tyr Cys Gln Gln His Asp Glu Tyr Pro Trp
                85                  90                  95

Thr Phe Gly Gln Gly Thr Lys Leu Glu Ile Lys Arg
            100                 105
```

<210> SEQ ID NO 38
<211> LENGTH: 107
<212> TYPE: PRT
<213> ORGANISM: Mus musculus

<400> SEQUENCE: 38

```
Gln Ile Val Leu Thr Gln Ser Pro Ala Ile Leu Ser Ala Ser Pro Gly
1               5                   10                  15

Glu Lys Val Thr Met Thr Cys Ser Ala Thr Ser Ser Ile Thr Tyr Ile
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Thr Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys Arg
            100                 105
```

<210> SEQ ID NO 39
<211> LENGTH: 106
<212> TYPE: PRT
<213> ORGANISM: Homo sapiens

<400> SEQUENCE: 39

```
Glu Ile Val Leu Thr Gln Ser Pro Ala Thr Leu Ser Ala Ser Pro Gly
1               5                   10                  15

Glu Lys Val Thr Met Thr Cys Ser Ala Thr Ser Ser Ile Thr Tyr Ile
            20                  25                  30

His Trp Tyr Gln Gln Lys Ser Gly Gln Ser Pro Lys Arg Trp Ile Tyr
        35                  40                  45

Asp Thr Ser Arg Leu Ala Ser Gly Val Pro Ser Arg Phe Ser Gly Ser
```

```
                50                  55                  60
Gly Ser Gly Thr Ser Tyr Ser Leu Thr Ile Ser Thr Met Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Gly Gly Thr Lys Leu Glu Ile Lys
            100                 105
```

<210> SEQ ID NO 40
<211> LENGTH: 106
<212> TYPE: PRT
<213> ORGANISM: Homo sapiens

<400> SEQUENCE: 40

```
Glu Ile Val Leu Thr Gln Ser Pro Ala Thr Leu Ser Ala Ser Pro Gly
 1               5                  10                  15

Glu Lys Val Thr Met Thr Cys Ser Ala Thr Ser Ser Ile Thr Tyr Ile
                 20                  25                  30

His Trp Tyr Gln Gln Lys Ser Gly Thr Ser Pro Lys Arg Trp Ile Tyr
                 35                  40                  45

Asp Thr Ser Arg Leu Ala Ser Gly Val Pro Ala Arg Phe Ser Gly Ser
             50                  55                  60

Gly Ser Gly Thr Ser Tyr Ser Leu Thr Ile Ser Thr Met Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Gly Gly Thr Lys Leu Glu Ile Lys
            100                 105
```

<210> SEQ ID NO 41
<211> LENGTH: 106
<212> TYPE: PRT
<213> ORGANISM: Homo sapiens

<400> SEQUENCE: 41

```
Glu Ile Val Leu Thr Gln Ser Pro Ala Thr Leu Ser Ala Ser Pro Gly
 1               5                  10                  15

Glu Lys Val Thr Met Thr Cys Ser Ala Thr Ser Ser Ile Thr Tyr Ile
                 20                  25                  30

His Trp Tyr Gln Gln Lys Pro Gly Gln Ala Pro Lys Arg Trp Ile Tyr
                 35                  40                  45

Asp Thr Ser Arg Leu Ala Ser Gly Val Pro Ala Arg Phe Ser Gly Ser
             50                  55                  60

Gly Ser Gly Thr Ser Tyr Ser Leu Thr Ile Ser Thr Met Glu Pro Glu
 65                  70                  75                  80

Asp Phe Ala Thr Tyr Tyr Cys Gln Gln Trp Ser Ser Asn Pro Pro Thr
                 85                  90                  95

Phe Gly Gly Gly Thr Lys Leu Glu Ile Lys
            100                 105
```

<210> SEQ ID NO 42
<211> LENGTH: 108
<212> TYPE: PRT
<213> ORGANISM: Homo sapiens

<400> SEQUENCE: 42

```
Asp Ile Gln Met Thr Gln Ser Pro Ser Ser Leu Ser Ala Ser Val Gly
 1               5                  10                  15
```

```
Asp Arg Val Thr Ser Thr Cys Arg Ala Ser Gln Asp Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys Arg
            100                 105

<210> SEQ ID NO 43
<211> LENGTH: 108
<212> TYPE: PRT
<213> ORGANISM: Homo sapiens

<400> SEQUENCE: 43

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ala Asp Ser Phe Pro Arg
                85                  90                  95

Thr Phe Gly Gln Gly Thr Lys Val Glu Ile Lys Arg
            100                 105

<210> SEQ ID NO 44
<211> LENGTH: 118
<212> TYPE: PRT
<213> ORGANISM: Oryctolagus cuniculus

<400> SEQUENCE: 44

Gln Ser Leu Glu Glu Ser Gly Gly Arg Leu Val Thr Pro Gly Thr Pro
1               5                   10                  15

Leu Thr Leu Thr Cys Thr Val Ser Gly Phe Asp Leu Ser Thr Tyr Ala
            20                  25                  30

Met Ser Trp Val Arg Gln Ala Pro Gly Lys Gly Leu Glu Trp Ile Gly
        35                  40                  45

Ala Val Ser Ala Thr Thr Gly Asn Thr Tyr Tyr Ala Thr Trp Ala Lys
    50                  55                  60

Gly Arg Phe Thr Met Ser Lys Ala Ser Thr Thr Val Asp Leu Lys Ile
65                  70                  75                  80

Thr Ser Pro Thr Thr Glu Asp Thr Ala Thr Tyr Phe Cys Val Arg Tyr
                85                  90                  95

Ala Ser Ser Gly Val Gly Thr Tyr Phe Asp Leu Trp Gly Gln Gly Thr
            100                 105                 110

Leu Val Thr Val Ser Ser
            115
```

```
<210> SEQ ID NO 45
<211> LENGTH: 123
<212> TYPE: PRT
<213> ORGANISM: Oryctolagus cuniculus

<400> SEQUENCE: 45

Gln Ser Leu Glu Glu Ser Gly Gly Leu Val Lys Pro Gly Ala Ser
1               5                   10                  15

Leu Thr Leu Thr Cys Thr Ala Ser Gly Phe Ser Phe Ser Gly Tyr
                20                  25                  30

Trp Ile Phe Trp Val Arg Gln Ala Pro Gly Lys Gly Leu Glu Leu Val
            35                  40                  45

Gly Gly Ile Tyr Ser Gly Ser Ser Gly Thr Thr Tyr Tyr Ala Asn Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Val Asp Gly Ile Asp Ser Tyr Asp Ala Ala Phe Asn Leu
                100                 105                 110

Trp Gly Pro Gly Thr Leu Val Thr Val Ser Ser
            115                 120

<210> SEQ ID NO 46
<211> LENGTH: 123
<212> TYPE: PRT
<213> ORGANISM: Oryctolagus cuniculus

<400> SEQUENCE: 46

Gln Ser Leu Glu Glu Ser Gly Gly Leu Val Lys Pro Gly Ala Ser
1               5                   10                  15

Leu Thr Leu Thr Cys Thr Ala Ser Gly Phe Ser Phe Ser Gly Tyr
                20                  25                  30

Trp Ile Phe Trp Val Arg Gln Ala Pro Gly Lys Gly Leu Glu Leu Val
            35                  40                  45

Gly Gly Ile Tyr Ser Gly Ser Ser Gly Thr Thr Tyr Tyr Ala Asn Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Val Asp Gly Ile Asp Ser Tyr Asp Ala Ala Phe Asn Leu
                100                 105                 110

Trp Gly Pro Gly Thr Leu Val Thr Val Ser Ser
            115                 120

<210> SEQ ID NO 47
<211> LENGTH: 122
<212> TYPE: PRT
<213> ORGANISM: Oryctolagus cuniculus

<400> SEQUENCE: 47

Gln Ser Leu Glu Glu Ser Gly Gly Asp Leu Ala Lys Pro Gly Ala Ser
1               5                   10                  15

Leu Thr Ile Thr Cys Thr Ala Ser Gly Phe Ser Phe Ser Ser Tyr
                20                  25                  30
```

```
Trp Ile Phe Trp Val Arg Gln Ala Pro Gly Lys Gly Leu Glu Leu Ile
         35                  40                  45
Gly Gly Ile Tyr Ser Ser Gly Arg Met Tyr Tyr Ala Ser Trp Ala
 50                  55                  60
Lys Gly Arg Phe Thr Ile Ser Lys Thr Ser Ser Thr Thr Met Thr Leu
65                  70                  75                  80
Gln Met Thr Ser Leu Thr Ala Ala Asp Thr Ala Thr Tyr Phe Cys Ala
                 85                  90                  95
Arg Ser Ala Asp Gly Ser Asp Ser Tyr Asp Ala Tyr Phe Thr Leu Trp
                100                 105                 110
Gly Pro Gly Thr Leu Val Thr Val Ser Ser
                115                 120
```

<210> SEQ ID NO 48
<211> LENGTH: 115
<212> TYPE: PRT
<213> ORGANISM: Oryctolagus cuniculus

<400> SEQUENCE: 48

```
Gln Ser Leu Glu Glu Ser Gly Gly Arg Leu Val Thr Pro Gly Gly Ser
1               5                   10                  15
Leu Thr Leu Thr Cys Thr Val Ser Gly Phe Ser Leu Ser Asn Tyr His
                 20                  25                  30
Leu Gly Trp Val Arg Arg Ala Pro Gly Lys Gly Leu Glu Trp Ile Gly
             35                  40                  45
Val Ile Thr Tyr Gly Gly Ser Thr Tyr Tyr Ala Ser Trp Val Lys Gly
 50                  55                  60
Arg Phe Thr Ile Ser Lys Thr Ser Thr Thr Val Asp Leu Lys Met Thr
65                  70                  75                  80
Ser Leu Thr Thr Glu Asp Thr Ala Thr Tyr Phe Cys Ala Arg Arg Asp
                 85                  90                  95
Ser Gly Gly Tyr His Leu Asp Leu Trp Gly Gln Gly Thr Leu Val Thr
                100                 105                 110
Ile Ser Ser
        115
```

<210> SEQ ID NO 49
<211> LENGTH: 109
<212> TYPE: PRT
<213> ORGANISM: Oryctolagus cuniculus

<400> SEQUENCE: 49

```
Gln Ser Val Glu Glu Ser Gly Gly Arg Leu Val Thr Pro Gly Gly Ser
1               5                   10                  15
Leu Thr Leu Thr Cys Thr Val Ser Gly Phe Ser Leu Ser Ser Asn Ala
                 20                  25                  30
Ile Asn Trp Val Arg Gln Ala Pro Gly Glu Gly Leu Asp Trp Ile Gly
             35                  40                  45
Thr Ile His Thr Asn Thr Lys Thr Tyr Tyr Ala Thr Trp Ala Arg Gly
 50                  55                  60
Arg Phe Thr Ile Ser Arg Thr Ser Ser Thr Thr Val Asp Leu Lys Val
65                  70                  75                  80
Thr Ser Leu Thr Ala Ala Asp Thr Ala Thr Tyr Phe Cys Gly Arg Ala
                 85                  90                  95
Asp Leu Trp Gly Gln Gly Thr Leu Val Thr Val Ser Ser
                100                 105
```

<210> SEQ ID NO 50
<211> LENGTH: 120
<212> TYPE: PRT
<213> ORGANISM: Mus musculus

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Val Lys Ser Tyr Asn Pro Ala
    50                  55                  60

Leu Lys Ser Arg Leu Thr Ile Ser Lys Asp Thr Ser Ser Ser Gln Val
65                  70                  75                  80

Phe Leu Arg Ile Ala Ser Val Asp Thr Ala Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Leu Thr Val Ser Ser
        115                 120

<210> SEQ ID NO 51
<211> LENGTH: 120
<212> TYPE: PRT
<213> ORGANISM: Homo sapiens

<400> SEQUENCE: 51

Gln Val Thr Leu Lys Glu Ser Gly Pro Thr Ile Leu Gln Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Ser Gly Lys Ala Leu Glu
        35                  40                  45

Trp Ile Ala His Ile Trp Trp Asp Asp Val Lys Ser Tyr Asn Pro Ala
    50                  55                  60

Leu Lys Ser Arg Leu Thr Ile Thr Lys Asp Thr Ser Lys Ser Gln Val
65                  70                  75                  80

Val Leu Arg Ile Ala Ser Val Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Leu Thr Val Ser Ser
        115                 120

<210> SEQ ID NO 52
<211> LENGTH: 120
<212> TYPE: PRT
<213> ORGANISM: Homo sapiens

<400> SEQUENCE: 52

Gln Val Thr Leu Lys Glu Ser Gly Pro Thr Ile Leu Gln Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Ser Gly Lys Gly Leu Glu

```
            35                  40                  45
Trp Ile Ala His Ile Trp Trp Asp Asp Val Lys Ser Tyr Asn Pro Ala
     50                  55                  60
Leu Lys Ser Arg Leu Thr Ile Thr Lys Asp Thr Ser Lys Ser Gln Val
 65                  70                  75                  80
Val Leu Arg Ile Ala Ser Val Asp Thr Ala Asp Thr Ala Thr Tyr Tyr
                 85                  90                  95
Cys Ala Arg Ile Gly Asp Gly Tyr Tyr Ser Phe Asp Tyr Trp Gly Gln
                100                 105                 110
Gly Thr Thr Leu Thr Val Ser Ser
                115                 120

<210> SEQ ID NO 53
<211> LENGTH: 120
<212> TYPE: PRT
<213> ORGANISM: Homo sapiens

<400> SEQUENCE: 53

Gln Val Thr Leu Lys Glu Ser Gly Pro Thr Leu Val Lys Pro Thr Gln
 1               5                   10                  15
Thr Leu Thr Leu Thr Cys Thr Phe Ser Gly Phe Ser Leu Ser Thr Ser
                 20                  25                  30
Gly Met Gly Val Gly Trp Ile Arg Gln Pro Pro Gly Lys Ala Leu Glu
             35                  40                  45
Trp Ile Ala His Ile Trp Trp Asp Asp Val Lys Ser Tyr Asn Pro Ala
     50                  55                  60
Leu Lys Ser Arg Leu Thr Ile Thr Lys Asp Thr Ser Lys Asn Gln Val
 65                  70                  75                  80
Val Leu Arg Ile Ala Ser Val Asp Pro Val Asp Thr Ala Thr Tyr Tyr
                 85                  90                  95
Cys Ala Arg Ile Gly Asp Gly Tyr Tyr Ser Phe Asp Tyr Trp Gly Gln
                100                 105                 110
Gly Thr Thr Leu Thr Val Ser Ser
                115                 120

<210> SEQ ID NO 54
<211> LENGTH: 116
<212> TYPE: PRT
<213> ORGANISM: Homo sapiens

<400> SEQUENCE: 54

Gln Val Gln Leu Val Glu Ser Gly Gly Gly Val Val Gln Pro Gly Arg
 1               5                   10                  15
Ser Leu Arg Leu Ser Cys Ala Ala Ser Gly Phe Thr Phe Ser Cys Tyr
                 20                  25                  30
Gly Met His Trp Val Arg Gln Ala Pro Gly Lys Gly Leu Glu Trp Val
             35                  40                  45
Ala Val Ile Trp Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Gly Gly Ala Thr Ala Met Asp Val Trp Gly Gln Gly Thr Thr Val
                100                 105                 110
Thr Val Ser Ser
```

<210> SEQ ID NO 55
<211> LENGTH: 126
<212> TYPE: PRT
<213> ORGANISM: Homo sapiens

<400> SEQUENCE: 55

Gln Glu Gln Ser Gly Gly Gly Val Val Gln Pro Gly Arg Ser Leu Arg
1               5                   10                  15

Leu Ser Cys Ala Ala Ser Gly Phe Thr Phe Ser Asn Tyr Gly Ile His
            20                  25                  30

Trp Val Arg Gln Ala Pro Gly Lys Gly Leu Glu Trp Val Ala Val Ile
        35                  40                  45

Trp Tyr Asp Gly Asn Asn Lys Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Arg Gly
                85                  90                  95

Gly Tyr Tyr Asp Ser Arg Gly Tyr Tyr Thr Pro Tyr Tyr Tyr Tyr Gly
            100                 105                 110

Met Asp Val Trp Gly Gln Gly Thr Thr Val Thr Val Ser Ser
        115                 120                 125

<210> SEQ ID NO 56
<211> LENGTH: 117
<212> TYPE: PRT
<213> ORGANISM: Homo sapiens

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Val Trp Asn Tyr Gly Asp Ala Phe Asp Ile Trp Gly Gln Gly Thr Met
            100                 105                 110

Val Thr Val Ser Ser
        115

<210> SEQ ID NO 57
<211> LENGTH: 111
<212> TYPE: PRT
<213> ORGANISM: Homo sapiens

<400> SEQUENCE: 57

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
 50                  55                  60

Arg Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 58
<211> LENGTH: 111
<212> TYPE: PRT
<213> ORGANISM: Homo sapiens

<400> SEQUENCE: 58

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
 50                  55                  60

Arg Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 59
<211> LENGTH: 111
<212> TYPE: PRT
<213> ORGANISM: Homo sapiens

<400> SEQUENCE: 59

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
 50                  55                  60

Arg Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 60
<211> LENGTH: 111
<212> TYPE: PRT
<213> ORGANISM: Homo sapiens

<400> SEQUENCE: 60

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Pro Pro Gly Lys Gly Leu Glu Trp Ile
        35                  40                  45

Gly Phe Ile Asp Pro Gly Gly Gly Tyr Asp Glu Pro Asp Glu Arg Phe
    50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 61
<211> LENGTH: 111
<212> TYPE: PRT
<213> ORGANISM: Homo sapiens

<400> SEQUENCE: 61

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Pro Pro Gly Lys Gly Leu Glu Trp Ile
        35                  40                  45

Gly Phe Ile Asp Pro Gly Gly Gly Tyr Asp Glu Pro Asp Glu Arg Phe
    50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Gly Tyr Tyr Leu Asp Tyr Trp Gly Gln Gly
            100                 105                 110

<210> SEQ ID NO 62
<211> LENGTH: 111
<212> TYPE: PRT
<213> ORGANISM: Homo sapiens

<400> SEQUENCE: 62

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Pro Pro Gly Lys Gly Leu Glu Trp Ile
        35                  40                  45

Gly Phe Ile Asp Pro Gly Gly Gly Tyr Asp Glu Pro Asp Glu Arg Phe
    50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Tyr Tyr Leu Asp Tyr Trp Gly Gln Gly
            100                 105                 110

<210> SEQ ID NO 63
<211> LENGTH: 111
<212> TYPE: PRT
<213> ORGANISM: Homo sapiens

<400> SEQUENCE: 63

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Pro Pro Gly Lys Gly Leu Glu Trp Ile
        35                  40                  45

Gly Phe Ile Asp Pro Gly Gly Gly Tyr Asp Glu Pro Asp Glu Arg Phe
    50                  55                  60

Arg Asp Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Arg Gly Gly Tyr Tyr Leu Asp Tyr Trp Gly Gln Gly
            100                 105                 110

<210> SEQ ID NO 64
<211> LENGTH: 111
<212> TYPE: PRT
<213> ORGANISM: Homo sapiens

<400> SEQUENCE: 64

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Ile Arg Gln Ser Pro Ser Arg Gly Leu Glu Trp Leu
        35                  40                  45

Gly Phe Ile Asp Pro Gly Gly Gly Tyr Asp Glu Pro Asp Glu Arg Phe
    50                  55                  60

Arg Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Gly Tyr Tyr Leu Asp Tyr Trp Gly Gln Gly
            100                 105                 110

<210> SEQ ID NO 65
<211> LENGTH: 111
<212> TYPE: PRT
<213> ORGANISM: Homo sapiens

<400> SEQUENCE: 65

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe

```
                    50                  55                  60
Arg Asp Arg Leu Thr Ile Ser Lys Asp Thr Ser Lys Asn Gln Val Val
 65                  70                  75                  80

Leu Thr Met Thr Asn Met Asp Pro Val Asp Thr Ala Thr Tyr Tyr Cys
                     85                  90                  95

Ala Arg Arg Gly Gly Gly Tyr Tyr Leu Asp Tyr Trp Gly Gln Gly
                100                 105                 110

<210> SEQ ID NO 66
<211> LENGTH: 111
<212> TYPE: PRT
<213> ORGANISM: Homo sapiens

<400> SEQUENCE: 66

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ile Phe Thr Asn Tyr
                 20                  25                  30

Pro Ile His Trp Val Arg Gln Ala Pro Gly Lys Gly Leu Glu Trp Val
                 35                  40                  45

Ser Phe Ile Asp Pro Gly Gly Tyr Asp Glu Pro Asp Glu Arg Phe
                 50                  55                  60

Arg Asp Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                     85                  90                  95

Ala Arg Arg Gly Gly Gly Tyr Tyr Leu Asp Tyr Trp Gly Gln Gly
                100                 105                 110

<210> SEQ ID NO 67
<211> LENGTH: 111
<212> TYPE: PRT
<213> ORGANISM: Homo sapiens

<400> SEQUENCE: 67

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ile Phe Thr Asn Tyr
                 20                  25                  30

Pro Ile His Trp Val Arg Gln Ala Pro Gly Gln Gly Leu Glu Trp Met
                 35                  40                  45

Gly Phe Ile Asp Pro Gly Gly Tyr Asp Glu Pro Asp Glu Arg Phe
                 50                  55                  60

Arg Asp Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                     85                  90                  95

Ala Arg Arg Gly Gly Gly Tyr Tyr Leu Asp Tyr Trp Gly Gln Gly
                100                 105                 110

<210> SEQ ID NO 68
<211> LENGTH: 111
<212> TYPE: PRT
<213> ORGANISM: Homo sapiens

<400> SEQUENCE: 68

Glu Val Gln Leu Val Gln Ser Gly Ala Glu Val Lys Lys Pro Gly Glu
 1               5                  10                  15
```

Ser Leu Arg Ile Ser Cys Lys Gly Ser Gly Tyr Ile Phe Thr Asn Tyr
            20                  25                  30

Pro Ile His Trp Val Arg Gln Ala Thr Gly Gln Gly Leu Glu Trp Met
            35                  40                  45

Gly Phe Ile Asp Pro Gly Gly Tyr Asp Glu Pro Asp Glu Arg Phe
    50                  55                  60

Arg Asp Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Thr Arg Gly Gly Gly Tyr Tyr Leu Asp Tyr Trp Gly Gln Gly
        100                 105                 110

<210> SEQ ID NO 69
<211> LENGTH: 118
<212> TYPE: PRT
<213> ORGANISM: Mus musculus

<400> SEQUENCE: 69

Gln Val Leu Leu Gln Gln Ser Ala Pro Glu Leu Ala Arg Pro Gly Ala
1               5                   10                  15

Ser Val Lys Met Ser Cys Thr Ala Ser Gly Tyr Ile Phe Thr Asn Tyr
            20                  25                  30

Pro Ile His Trp Val Lys Gln Arg Pro Gly Gln Gly Leu Glu Trp Ile
            35                  40                  45

Gly Phe Ile Asp Pro Gly Gly Tyr Asp Glu Pro Asp Glu Arg Phe
    50                  55                  60

Arg Asp Arg Ala Thr Leu Thr Ala Asp Lys Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Gly Gly Gly Tyr Tyr Leu Asp Tyr Trp Gly Gln Gly Thr
        100                 105                 110

Thr Leu Thr Val Ser Ser
        115

<210> SEQ ID NO 70
<211> LENGTH: 111
<212> TYPE: PRT
<213> ORGANISM: Homo sapiens

<400> SEQUENCE: 70

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
            35                  40                  45

Ser Phe Ile Asp Pro Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
        100                 105                 110

<210> SEQ ID NO 71
<211> LENGTH: 111
<212> TYPE: PRT
<213> ORGANISM: Homo sapiens

<400> SEQUENCE: 71

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110
```

<210> SEQ ID NO 72
<211> LENGTH: 111
<212> TYPE: PRT
<213> ORGANISM: Homo sapiens

<400> SEQUENCE: 72

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Pro Gly Lys Gly Leu Glu Trp Val
        35                  40                  45

Ser Phe Ile Asp Pro Gly Gly Gly Tyr Asp Glu Pro Asp Glu Arg Phe
    50                  55                  60

Arg Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Arg Gly Gly Gly Tyr Tyr Leu Asp Tyr Trp Gly Gln Gly
            100                 105                 110
```

<210> SEQ ID NO 73
<211> LENGTH: 111
<212> TYPE: PRT
<213> ORGANISM: Homo sapiens

<400> SEQUENCE: 73

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Thr Gly Gln Gly Leu Glu Trp Met
        35                  40                  45

Gly Phe Ile Asp Pro Gly Gly Gly Tyr Asp Glu Pro Asp Glu Arg Phe
    50                  55                  60
```

```
Arg Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Gly Gly Tyr Tyr Leu Asp Tyr Trp Gly Gln Gly
            100                 105                 110

<210> SEQ ID NO 74
<211> LENGTH: 118
<212> TYPE: PRT
<213> ORGANISM: Homo sapiens

<400> SEQUENCE: 74

Gln Val Gln Leu Val Gln Ser Ala Pro Glu Val Ala Lys Pro Gly Thr
  1               5                  10                  15

Ser Val Lys Met Ser Cys Lys Ala Ser Gly Tyr Ile Phe Thr Asn Tyr
                 20                  25                  30

Pro Ile His Trp Val Lys Gln Ala Pro Gly Gln Gly Leu Glu Trp Ile
             35                  40                  45

Gly Phe Ile Asp Pro Gly Gly Gly Tyr Asp Glu Pro Asp Glu Arg Phe
 50                  55                  60

Arg Asp Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Ile Tyr Tyr Cys
                 85                  90                  95

Ala Arg Arg Gly Gly Gly Tyr Tyr Leu Asp Tyr Trp Gly Gln Gly Thr
            100                 105                 110

Leu Val Thr Val Ser Ser
        115

<210> SEQ ID NO 75
<211> LENGTH: 118
<212> TYPE: PRT
<213> ORGANISM: Homo sapiens

<400> SEQUENCE: 75

Gln Val Gln Leu Val Gln Ser Gly Pro Glu Val Ala Lys Pro Gly Ser
  1               5                  10                  15

Ser Val Lys Val Ser Cys Lys Ala Ser Gly Tyr Ile Phe Thr Asn Tyr
                 20                  25                  30

Pro Ile His Trp Val Arg Gln Ala Pro Gly Gln Gly Leu Glu Trp Ile
             35                  40                  45

Gly Phe Ile Asp Pro Gly Gly Gly Tyr Asp Glu Pro Asp Glu Arg Phe
 50                  55                  60

Arg Asp Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Gly Gly Tyr Tyr Leu Asp Tyr Trp Gly Gln Gly Thr
            100                 105                 110

Leu Val Thr Val Ser Ser
        115

<210> SEQ ID NO 76
<211> LENGTH: 232
<212> TYPE: PRT
<213> ORGANISM: Mus musculus
```

<400> SEQUENCE: 76

Leu Asn Met Glu Arg His Trp Ile Phe Leu Phe Leu Leu Ser Val Thr
1               5                   10                  15

Ala Gly Val His Ser Gln Val Leu Leu Gln Gln Ser Ala Pro Glu Leu
            20                  25                  30

Ala Arg Pro Gly Ala Ser Val Lys Met Ser Cys Thr Ala Ser Gly Tyr
        35                  40                  45

Ile Phe Thr Asn Tyr Pro Ile His Trp Val Lys Gln Arg Pro Gly Gln
    50                  55                  60

Gly Leu Glu Trp Ile Gly Phe Ile Asp Pro Gly Gly Tyr Asp Glu
65                  70                  75                  80

Pro Asp Glu Arg Phe Arg Asp Arg Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Ile Tyr Tyr Cys Ala Arg Arg Gly Gly Gly Tyr Tyr Leu Asp Tyr
        115                 120                 125

Trp Gly Gln Asp Thr Thr Leu Thr Val Ser Ala Ala Ser Thr Thr Pro
130                 135                 140

Pro Ser Val Lys Gly Glu Phe Phe Ile Asp Pro Gly Gly Gly Tyr Asp
145                 150                 155                 160

Glu Pro Asp Glu Arg Phe Arg Asp Arg Ala Thr Leu Thr Ala Asp Lys
                165                 170                 175

Ser Ser Ser Thr Ala Tyr Met Gln Leu Ser Ser Leu Thr Ser Glu Asp
            180                 185                 190

Ser Ala Ile Tyr Tyr Cys Ala Arg Arg Gly Gly Tyr Tyr Leu Asp
        195                 200                 205

Tyr Trp Gly Gln Asp Thr Thr Leu Thr Val Ser Ala Ala Ser Thr Thr
210                 215                 220

Pro Pro Ser Val Lys Gly Glu Phe
225                 230

<210> SEQ ID NO 77
<211> LENGTH: 98
<212> TYPE: PRT
<213> ORGANISM: Mus musculus

<400> SEQUENCE: 77

Glu Val Gln Leu Gln Gln Ser Val Pro Glu Leu Ala Arg Pro Gly Ala
1               5                   10                  15

Ser Val Lys Met Ser Cys Thr Ala Ser Gly Tyr Ile Phe Thr Thr Tyr
            20                  25                  30

Pro Ile His Trp Val Lys Gln Arg Pro Gly Gln Gly Leu Glu Trp Ile
        35                  40                  45

Gly Phe Ile Asp Pro Gly Gly Gly Tyr Asp Glu Pro Asp Asp Lys Phe
    50                  55                  60

Arg Asp Arg Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 78
<211> LENGTH: 121
<212> TYPE: PRT

<213> ORGANISM: Mus musculus

<400> SEQUENCE: 78

Gln Val Gln Leu Gln Gln Ser Gly Ala Glu Leu Ala Lys Pro Gly Ala
1               5                   10                  15

Ser Val Arg Met Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Tyr Ile Asn Pro Asn Thr Gly Tyr Asn Asp Tyr Asn Gln Lys Phe
    50                  55                  60

Lys Asp Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
            85                  90                  95

Ala Arg Gly Gly Gln Leu Gly Leu Arg Arg Ala Met Asp Tyr Trp Gly
        100                 105                 110

Gln Gly Thr Ser Val Thr Val Ser Ser
    115                 120

<210> SEQ ID NO 79
<211> LENGTH: 121
<212> TYPE: PRT
<213> ORGANISM: Homo sapiens

<400> SEQUENCE: 79

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Tyr Ile Asn Pro Asn Thr Gly Tyr Asn Asp Tyr Asn Gln Lys Phe
    50                  55                  60

Lys Asp Arg Ala Thr Leu Thr Ala Asp Lys Ser Ser Ser Thr Val Tyr
65                  70                  75                  80

Met Gln Leu Ser Ser Leu Arg Ser Glu Asp Thr Ala Val Tyr Tyr Cys
            85                  90                  95

Ala Arg Gly Gly Gln Leu Gly Leu Arg Arg Ala Met Asp Tyr Trp Gly
        100                 105                 110

Gln Gly Thr Leu Val Thr Val Ser Ser
    115                 120

<210> SEQ ID NO 80
<211> LENGTH: 121
<212> TYPE: PRT
<213> ORGANISM: Homo sapiens

<400> SEQUENCE: 80

Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Tyr Ile Asn Pro Asn Thr Gly Tyr Asn Asp Tyr Asn Gln Lys Phe
    50                  55                  60

Lys Asp Lys Ala Thr Leu Thr Ala Asp Lys Ser Ser Thr Val Tyr
65                  70                  75                  80

Met Gln Leu Ser Ser Leu Thr Ser Glu Asp Thr Ala Val Tyr Tyr Cys
                85                  90                  95

Ala Arg Gly Gly Gln Leu Gly Leu Arg Arg Ala Met Asp Tyr Trp Gly
            100                 105                 110

Gln Gly Thr Leu Val Thr Val Ser Ser
        115                 120

<210> SEQ ID NO 81
<211> LENGTH: 120
<212> TYPE: PRT
<213> ORGANISM: Mus musculus

<400> SEQUENCE: 81

Gln Val Gln Leu Gln Gln Ser Gly Ala Glu Ile Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Lys Met Ile Pro Asp Thr Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Ser Val Thr Val Ser Ser
        115                 120

<210> SEQ ID NO 82
<211> LENGTH: 120
<212> TYPE: PRT
<213> ORGANISM: Homo sapiens

<400> SEQUENCE: 82

Gln Val Gln Leu Val Gln Ser Gly Ala Glu Ile Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Lys Gln Ala Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Thr Met Ile Pro Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Met Val Thr Val Ser Ser
        115                 120

<210> SEQ ID NO 83

```
<211> LENGTH: 120
<212> TYPE: PRT
<213> ORGANISM: Homo sapiens

<400> SEQUENCE: 83

Gln Val Gln Leu Val Gln Ser Gly Ala Glu Ile Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Lys Met Ile Pro Asp Thr Ser Thr Ser Thr Val Tyr
65                  70                  75                  80

Met Gln Leu Ser Ser Leu Thr Ser Glu Asp Thr Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Met Val Thr Val Ser Ser
        115                 120

<210> SEQ ID NO 84
<211> LENGTH: 120
<212> TYPE: PRT
<213> ORGANISM: Homo sapiens

<400> SEQUENCE: 84

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Thr Met Ile Pro Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Met Val Thr Val Ser Ser
        115                 120

<210> SEQ ID NO 85
<211> LENGTH: 128
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1               5                   10                  15

Ser Val Lys Val Ser Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45
```

```
Gly Gly Phe Asp Pro Glu Asp Gly Glu Thr Ile Tyr Ala Gln Met Phe
    50                  55                  60
Gln Gly Arg Val Thr Met Thr Glu Asp Thr Ser Thr Asp Thr Ala Tyr
65                  70                  75                  80
Met Asp Leu Ser Ser Leu Arg Ser Glu Asp Thr Ala Val Tyr Tyr Cys
                85                  90                  95
Ala Thr Gly Thr Tyr Tyr Asp Ile Leu Thr Gly Pro Ser Tyr Tyr Tyr
                100                 105                 110
Tyr Gly Leu Gly Val Trp Gly Gln Gly Thr Thr Val Thr Val Ser Ser
                115                 120                 125
```

<210> SEQ ID NO 86
<211> LENGTH: 117
<212> TYPE: PRT
<213> ORGANISM: Homo sapiens

<400> SEQUENCE: 86

```
Gln Val Gln Leu Glu Gln Ser Gly Pro Gly Leu Val Lys Pro Ser Gln
1               5                   10                  15
Thr Leu Ser Leu Thr Cys Thr Val Ser Gly Asp Ser Ile Ser Ser Gly
                20                  25                  30
Gly His Tyr Trp Ser Trp Ile Arg Gln His Pro Gly Lys Gly Leu Glu
                35                  40                  45
Trp Ile Gly Tyr Ile Tyr Tyr Ser Gly Ser Ser Tyr Tyr Asn Pro Ser
    50                  55                  60
Leu Lys Ser Arg Phe Thr Ile Ser Val Asp Thr Ser Lys Asn Gln Phe
65                  70                  75                  80
Ser Leu Lys Leu Thr Ser Val Thr Ala Ala Asp Thr Ala Val Tyr Tyr
                85                  90                  95
Cys Ala Arg Thr Gly Asp Tyr Phe Asp Tyr Trp Gly Leu Gly Thr Leu
                100                 105                 110
Val Thr Val Ser Ser
            115
```

<210> SEQ ID NO 87
<211> LENGTH: 448
<212> TYPE: PRT
<213> ORGANISM: Homo sapiens

<400> SEQUENCE: 87

```
Glu Val Gln Leu Val Gln Ser Gly Ala Glu Val Lys Lys Pro Gly Glu
1               5                   10                  15
Ser Leu Arg Ile Ser Cys Lys Gly Ser Gly Tyr Ile Phe Thr Asn Tyr
                20                  25                  30
Pro Ile His Trp Ile Arg Gln Ser Pro Ser Arg Gly Leu Glu Trp Leu
                35                  40                  45
Gly Phe Ile Asp Pro Gly Gly Gly Tyr Asp Glu Pro Asp Glu Arg Phe
    50                  55                  60
Arg Asp Arg Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Arg Gly Gly Gly Tyr Tyr Leu Asp Tyr Trp Gly Gln Gly Thr
                100                 105                 110
Leu Val Thr Val Ser Ser Ala Ser Thr Lys Gly Pro Ser Val Phe Pro
                115                 120                 125
```

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 88
<211> LENGTH: 214
<212> TYPE: PRT
<213> ORGANISM: Homo sapiens

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Gly Asn Thr Leu Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 89
<211> LENGTH: 448
<212> TYPE: PRT
<213> ORGANISM: Homo sapiens

<400> SEQUENCE: 89

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ile Phe Thr Asn Tyr
            20                  25                  30

Pro Ile His Trp Val Arg Gln Ala Thr Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr

```
                210                 215                 220
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 90
<211> LENGTH: 214
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Ile Pro Pro Arg Phe Ser Gly
        50                  55                  60

Ser Gly Tyr Gly Thr Glu Phe Thr Phe Thr Ile Ser Ser Leu Glu Ala
65                  70                  75                  80

Glu Asp Ala Ala Thr Tyr Tyr Cys Gln His Gly Asn Thr Leu Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 448
<212> TYPE: PRT
<213> ORGANISM: Homo sapiens

<400> SEQUENCE: 91

Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
            20                  25                  30

Pro Ile His Trp Val Lys Gln Ala Pro Gly Gln Gly Leu Glu Trp Ile
        35                  40                  45

Gly Phe Ile Asp Pro Gly Gly Tyr Asp Pro Asp Glu Arg Phe
    50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 92
<211> LENGTH: 214
<212> TYPE: PRT
<213> ORGANISM: Homo sapiens

<400> SEQUENCE: 92

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

```
<210> SEQ ID NO 93
<211> LENGTH: 448
<212> TYPE: PRT
<213> ORGANISM: Homo sapiens

<400> SEQUENCE: 93

Gln Val Gln Leu Val Gln Ser Gly Pro Glu Val Ala Lys Pro Gly Ser
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Ile
        35                  40                  45

Gly Phe Ile Asp Pro Gly Gly Tyr Asp Glu Pro Asp Glu Arg Phe
    50                  55                  60

Arg Asp Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
        435                 440                 445

<210> SEQ ID NO 94
<211> LENGTH: 214
<212> TYPE: PRT
<213> ORGANISM: Homo sapiens

<400> SEQUENCE: 94

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 95
<211> LENGTH: 448
<212> TYPE: PRT
<213> ORGANISM: Homo sapiens

<400> SEQUENCE: 95

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Ile
        35                  40                  45

Gly Phe Ile Asp Pro Gly Gly Gly Tyr Asp Glu Pro Asp Glu Arg Phe
 50                  55                  60

Arg Asp Arg Ala Thr Leu Thr Ala Asp Lys Ser Ser Thr Ala Tyr
 65                  70                  75                  80

Met Gln Leu Ser Ser Leu Thr Ser Glu Asp Ser Ala Ile Tyr Tyr Cys
                 85                  90                  95

Ala Arg Arg Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 96
<211> LENGTH: 214
<212> TYPE: PRT

<213> ORGANISM: Homo sapiens

<400> SEQUENCE: 96

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 448
<212> TYPE: PRT
<213> ORGANISM: Homo sapiens

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Lys Gly Leu Glu Trp Ile
        35                  40                  45

Gly Phe Ile Asp Pro Gly Gly Tyr Asp Glu Pro Asp Glu Arg Phe
50                  55                  60

Arg Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
            130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 98
<211> LENGTH: 214
<212> TYPE: PRT
<213> ORGANISM: Homo sapiens

<400> SEQUENCE: 98

Asp Ile Gln Met Thr Gln Ser Thr Ser Ser Leu Ser Ala Ser Leu Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
                35                  40                  45

Tyr Tyr Thr Ser Arg Tyr His Ser Gly Val Pro Ser Arg Phe Ser Gly
            50                  55                  60
```

-continued

```
Ser Gly Ser Gly Thr Asp Phe Thr Leu Thr Ile Ser Asn Leu Gln Pro
 65                  70                  75                  80

Glu Asp Phe Ala Thr Tyr Phe Cys Gln His Gly Asn Thr Leu Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 99
<211> LENGTH: 450
<212> TYPE: PRT
<213> ORGANISM: Homo sapiens

<400> SEQUENCE: 99

Gln Val Thr Leu Lys Glu Ser Gly Pro Thr Ile Leu Gln Pro Thr Gln
  1               5                  10                  15

Thr Leu Thr Leu Thr Cys Thr Phe Ser Gly Phe Ser Leu Ser Thr Ser
                 20                  25                  30

Gly Met Gly Val Gly Trp Ile Arg Gln Pro Ser Gly Lys Ala Leu Glu
             35                  40                  45

Trp Ile Ala His Ile Trp Trp Asp Asp Val Lys Ser Tyr Asn Pro Ala
         50                  55                  60

Leu Lys Ser Arg Leu Thr Ile Thr Lys Asp Thr Ser Lys Ser Gln Val
 65                  70                  75                  80

Val Leu Arg Ile Ala Ser Val Asp Pro Val Asp Thr Ala Thr Tyr Tyr
                 85                  90                  95

Cys Ala Arg Ile Gly Asp Gly Tyr Tyr Ser Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 100
<211> LENGTH: 214
<212> TYPE: PRT
<213> ORGANISM: Homo sapiens

<400> SEQUENCE: 100

Asp Ile Gln Met Thr Gln Ser His Lys Phe Met Ser Thr Ser Val Gly
1               5                   10                  15

Asp Arg Val Thr Ile Thr Cys Lys Ala Ser Gln Asp Val Ser Asp Ala
            20                  25                  30

Val Ala Trp Phe Gln Gln Lys Pro Gly Lys Ser Pro Lys Leu Leu Ile
        35                  40                  45

Tyr Ser Pro Ser Tyr Arg Tyr Thr Gly Val Pro Ser Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
            85                  90                  95

Thr Phe Gly Gln Gly Thr Lys Leu Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 101
<211> LENGTH: 450
<212> TYPE: PRT
<213> ORGANISM: Homo sapiens

<400> SEQUENCE: 101

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Ile Ala His Ile Trp Trp Asp Asp Val Lys Ser Tyr Asn Pro Ala
        50                  55                  60

Leu Lys Ser Arg Leu Thr Ile Thr Lys Asp Thr Ser Lys Asn Gln Val
65                  70                  75                  80

Val Leu Arg Ile Ala Ser Val Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
                100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285
```

-continued

```
Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 102
<211> LENGTH: 214
<212> TYPE: PRT
<213> ORGANISM: Homo sapiens

<400> SEQUENCE: 102

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys
    210

<210> SEQ ID NO 103
<211> LENGTH: 230
<212> TYPE: PRT
<213> ORGANISM: Homo sapiens

<400> SEQUENCE: 103

Gln Ser Leu Glu Glu Ser Gly Gly Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Trp Ile Phe Trp Val Arg Gln Ala Pro Gly Lys Gly Leu Glu Leu Val
        35                  40                  45

Gly Gly Ile Tyr Ser Gly Ser Ser Gly Thr Thr Tyr Tyr Ala Asn Trp
    50                  55                  60

Ala Lys Gly Arg Phe Thr Ile Ser Lys Thr Ser Thr Thr Val
65                  70                  75                  80

Leu Gln Met Thr Ser Leu Thr Ala Ala Asp Thr Ala Thr Tyr Phe Cys
                85                  90                  95

Ala Arg Ser Val Asp Gly Ile Asp Ser Tyr Asp Ala Ala Phe Asn Leu
            100                 105                 110

Trp Gly Pro Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His
225                 230

<210> SEQ ID NO 104
<211> LENGTH: 217
<212> TYPE: PRT
<213> ORGANISM: Homo sapiens

<400> SEQUENCE: 104

Ala Tyr Asp Leu Thr Gln Thr Pro Ala Ser Val Glu Ala Ala Val Gly
1               5                   10                  15

Gly Thr Val Thr Ile Asn Cys Gln Ala Ser Asp Asn Ile Tyr Ser Leu
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80
```

Ala Asp Ala Ala Thr Tyr Tyr Cys Gln Gln His Tyr Asp Tyr Asn Tyr
                85                  90                  95

Leu Asp Val Ala Phe Gly Gly Gly Thr Glu Val Val Lys Gly Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 105
<211> LENGTH: 448
<212> TYPE: PRT
<213> ORGANISM: Homo sapiens

<400> SEQUENCE: 105

Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
            20                  25                  30

Pro Ile His Trp Val Lys Gln Ala Pro Gly Gln Gly Leu Glu Trp Ile
        35                  40                  45

Gly Phe Ile Asp Pro Gly Gly Gly Tyr Asp Pro Asp Glu Arg Phe
    50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser 225                 230                 235                 240
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 106
<211> LENGTH: 214
<212> TYPE: PRT
<213> ORGANISM: Homo sapiens

<400> SEQUENCE: 106

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 107
<211> LENGTH: 225
<212> TYPE: PRT
<213> ORGANISM: Homo sapiens

<400> SEQUENCE: 107

Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
            20                  25                  30

Pro Ile His Trp Val Lys Gln Ala Pro Gly Gln Gly Leu Glu Trp Ile
        35                  40                  45

Gly Phe Ile Asp Pro Gly Gly Tyr Asp Glu Pro Asp Glu Arg Phe
    50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His
225

<210> SEQ ID NO 108
<211> LENGTH: 214
<212> TYPE: PRT
<213> ORGANISM: Homo sapiens

<400> SEQUENCE: 108

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

```
Leu Asn Trp Tyr Gln Gln Lys Pro Asp Gly Thr Val Lys Leu Leu Ile
             35                  40                  45

Tyr Tyr Thr Ser Arg Tyr His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln His Gly Asn Thr Leu Pro Trp
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 109
<211> LENGTH: 448
<212> TYPE: PRT
<213> ORGANISM: Homo sapiens

<400> SEQUENCE: 109

Gln Val Gln Leu Val Gln Ser Ala Pro Glu Val Ala Lys Pro Gly Thr
  1               5                  10                  15

Ser Val Lys Met Ser Cys Lys Ala Ser Gly Tyr Ile Phe Thr Asn Tyr
             20                  25                  30

Pro Ile His Trp Val Lys Gln Ala Pro Gly Gln Gly Leu Glu Trp Ile
         35                  40                  45

Gly Phe Ile Asp Pro Gly Gly Tyr Asp Glu Pro Asp Glu Arg Phe
     50                  55                  60

Arg Asp Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Ile Tyr Tyr Cys
                 85                  90                  95

Ala Arg Arg Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205

Asn Thr Lys Val Gly Gly Gly Ser Gly Gly Gly Ser Gly Gly
        210                 215                 220

Gly Gly Ser Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 110
<211> LENGTH: 450
<212> TYPE: PRT
<213> ORGANISM: Homo sapiens

<400> SEQUENCE: 110

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 111
<211> LENGTH: 448
<212> TYPE: PRT
<213> ORGANISM: Homo sapiens

<400> SEQUENCE: 111

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Ile Phe Thr Asn Tyr
            20                  25                  30
```

```
Pro Ile His Trp Val Arg Gln Ala Pro Gly Gln Gly Leu Glu Trp Ile
         35                  40                  45
Gly Phe Ile Asp Pro Gly Gly Tyr Asp Glu Pro Asp Glu Arg Phe
 50                  55                  60
Arg Asp Arg Ala Thr Leu Thr Ala Asp Lys Ser Ser Thr Ala Tyr
 65                  70                  75                  80
Met Gln Leu Ser Ser Leu Thr Ser Glu Asp Ser Ala Ile Tyr Tyr Cys
                 85                  90                  95
Ala Arg Arg Gly Gly Tyr Tyr Leu Asp Tyr Trp Gly Gln Gly Thr
                100                 105                 110
Leu Val Thr Val Ser Ser Ala Ser Thr Lys Gly Pro Ser Val Phe Pro
             115                 120                 125
Leu Ala Pro Ser Ser Lys Ser Thr Ser Gly Gly Thr Ala Ala Leu Gly
 130                 135                 140
Cys Leu Val Lys Asp Tyr Phe Pro Glu Pro Val Thr Val Ser Trp Asn
 145                 150                 155                 160
Ser Gly Ala Leu Thr Ser Gly Val His Thr Phe Pro Ala Val Leu Gln
                 165                 170                 175
Ser Ser Gly Leu Tyr Ser Leu Ser Ser Val Val Thr Val Pro Ser Ser
             180                 185                 190
Ser Leu Gly Thr Gln Thr Tyr Ile Cys Asn Val Asn His Lys Pro Ser
         195                 200                 205
Asn Thr Lys Val Gly Gly Gly Ser Gly Gly Gly Ser Gly Gly
 210                 215                 220
Gly Gly Ser Pro Pro Cys Pro Ala Pro Glu Leu Leu Gly Gly Pro Ser
 225                 230                 235                 240
Val Phe Leu Phe Pro Pro Lys Pro Lys Asp Thr Leu Met Ile Ser Arg
                 245                 250                 255
Thr Pro Glu Val Thr Cys Val Val Asp Val Ser His Glu Asp Pro
             260                 265                 270
Glu Val Lys Phe Asn Trp Tyr Val Asp Gly Val Glu Val His Asn Ala
                 275                 280                 285
Lys Thr Lys Pro Arg Glu Glu Gln Tyr Ala Ser Thr Tyr Arg Val Val
 290                 295                 300
Ser Val Leu Thr Val Leu His Gln Asp Trp Leu Asn Gly Lys Glu Tyr
 305                 310                 315                 320
Lys Cys Lys Val Ser Asn Lys Ala Leu Pro Ala Pro Ile Glu Lys Thr
                 325                 330                 335
Ile Ser Lys Ala Lys Gly Gln Pro Arg Glu Pro Gln Val Tyr Thr Leu
             340                 345                 350
Pro Pro Ser Arg Asp Glu Leu Thr Lys Asn Gln Val Ser Leu Thr Cys
         355                 360                 365
Leu Val Lys Gly Phe Tyr Pro Ser Asp Ile Ala Val Glu Trp Glu Ser
     370                 375                 380
Asn Gly Gln Pro Glu Asn Asn Tyr Lys Thr Thr Pro Pro Val Leu Asp
 385                 390                 395                 400
Ser Asp Gly Ser Phe Phe Leu Tyr Ser Lys Leu Thr Val Asp Lys Ser
                 405                 410                 415
Arg Trp Gln Gln Gly Asn Val Phe Ser Cys Ser Val Met His Glu Ala
                 420                 425                 430
Leu His Asn His Tyr Thr Gln Lys Ser Leu Ser Leu Ser Pro Gly Lys
             435                 440                 445
```

-continued

```
<210> SEQ ID NO 112
<211> LENGTH: 450
<212> TYPE: PRT
<213> ORGANISM: Homo sapiens

<400> SEQUENCE: 112

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Ser
    210                 215                 220

Gly Gly Gly Gly Ser Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
    450

<210> SEQ ID NO 113
<211> LENGTH: 450
<212> TYPE: PRT
<213> ORGANISM: Homo sapiens

<400> SEQUENCE: 113

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Ile Ala His Ile Trp Trp Asp Asp Val Lys Ser Tyr Asn Pro Ala
    50                  55                  60

Leu Lys Ser Arg Leu Thr Ile Thr Lys Asp Thr Ser Lys Asn Gln Val
65                  70                  75                  80

Val Leu Arg Ile Ala Ser Val Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Gly Gly Gly Ser Gly Gly Gly Gly Gly Ser
    210                 215                 220

Gly Gly Gly Gly Ser Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 114
<211> LENGTH: 450
<212> TYPE: PRT
<213> ORGANISM: Homo sapiens

<400> SEQUENCE: 114

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asp Val Ser Asp Ala
                20                  25                  30

Val Ala Trp Phe Gln Gln Lys Pro Gly Lys Ala Pro Lys Leu Leu Ile
            35                  40                  45

Tyr Ser Pro Ser Tyr Arg Tyr Thr Gly Val Pro Ser Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
```

Gly Gly Gly Gly Ser Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 115
<211> LENGTH: 450
<212> TYPE: PRT
<213> ORGANISM: Homo sapiens

<400> SEQUENCE: 115

Gln Val Gln Leu Gln Gln Ser Gly Ala Glu Ile Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Lys Met Ile Pro Asp Thr Ser Ser Thr Val Tyr
65                  70                  75                  80

Met Gln Leu Ser Ser Leu Thr Ser Glu Asp Ser Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Ser Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 116
<211> LENGTH: 213
<212> TYPE: PRT
<213> ORGANISM: Homo sapiens

<400> SEQUENCE: 116

Gln Ile Val Leu Thr Gln Ser Pro Ala Ile Leu Ser Ala Ser Pro Gly
1               5                   10                  15

Glu Lys Val Thr Met Thr Cys Ser Ala Thr Ser Ser Ile Thr Tyr Ile
                20                  25                  30

His Trp Tyr Gln Gln Lys Ser Gly Thr Ser Pro Lys Arg Trp Ile Tyr
            35                  40                  45
```

```
Asp Thr Ser Arg Leu Ala Ser Gly Val Pro Thr Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ser Ser Asn Pro Pro Thr
                    85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 117
<211> LENGTH: 450
<212> TYPE: PRT
<213> ORGANISM: Homo sapiens

<400> SEQUENCE: 117

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Thr Met Ile Pro Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Gly Asn Phe Gly Asn Phe Asp Ala Met Asp Tyr Trp Gly Gln
                100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
```

```
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                    245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Ala Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                    325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                    405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys
    450

<210> SEQ ID NO 118
<211> LENGTH: 213
<212> TYPE: PRT
<213> ORGANISM: Homo sapiens

<400> SEQUENCE: 118

Glu Ile Val Leu Thr Gln Ser Pro Ala Thr Leu Ser Ala Ser Pro Gly
1               5                   10                  15
Glu Lys Val Thr Met Thr Cys Ser Ala Thr Ser Ser Ile Thr Tyr Ile
                20                  25                  30
His Trp Tyr Gln Gln Lys Pro Gly Gln Ala Pro Lys Arg Trp Ile Tyr
            35                  40                  45
Asp Thr Ser Arg Leu Ala Ser Gly Val Pro Ala Arg Phe Ser Gly Ser
        50                  55                  60
Gly Ser Gly Thr Ser Tyr Ser Leu Thr Ile Ser Thr Met Glu Pro Glu
65                  70                  75                  80
Asp Phe Ala Thr Tyr Tyr Cys Gln Gln Trp Ser Ser Asn Pro Pro Thr
                85                  90                  95
Phe Gly Gly Gly Thr Lys Leu Glu Ile Lys Arg Thr Val Ala Ala Pro
                100                 105                 110
```

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 119
<211> LENGTH: 451
<212> TYPE: PRT
<213> ORGANISM: Homo sapiens

<400> SEQUENCE: 119

Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Tyr Ile Asn Pro Asn Thr Gly Tyr Asn Asp Tyr Asn Gln Lys Phe
    50                  55                  60

Lys Asp Lys Ala Thr Leu Thr Ala Asp Lys Ser Ser Ser Thr Val Tyr
65                  70                  75                  80

Met Gln Leu Ser Ser Leu Thr Ser Glu Asp Thr Ala Val Tyr Tyr Cys
                85                  90                  95

Ala Arg Gly Gly Gln Leu Gly Leu Arg Arg Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

-continued

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
435                 440                 445

Pro Gly Lys
450

<210> SEQ ID NO 120
<211> LENGTH: 214
<212> TYPE: PRT
<213> ORGANISM: Homo sapiens

<400> SEQUENCE: 120

Asp Val Gln Ile Thr Gln Ser Pro Ser Tyr Leu Ala Ser Pro Gly
1               5                   10                  15

Asp Thr Ile Thr Ile Thr Cys Arg Ala Ser Lys Ser Ile Ser Lys Tyr
                20                  25                  30

Leu Ala Trp Tyr Gln Asp Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Met Tyr Tyr Cys Gln Gln His Asp Glu Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
             180                 185                 190
Ala Cys Glu Val Thr His Gln Gly Leu Ser Ser Pro Val Thr Lys Ser
         195                 200                 205

Phe Asn Arg Gly Glu Cys
    210
```